United States Patent
Hinman et al.

(10) Patent No.: US 10,703,701 B2
(45) Date of Patent: Jul. 7, 2020

(54) FLUOROALKYL, FLUOROALKOXY, PHENOXY, HETEROARYLOXY, ALKOXY, AND AMINE 1,4-BENZOQUINONE DERIVATIVES FOR TREATMENT OF OXIDATIVE STRESS DISORDERS

(71) Applicant: PTC Therapeutics, Inc., South Plainfield, NJ (US)

(72) Inventors: Andrew W. Hinman, South San Francisco, CA (US); Steven J. Richards, Brisbane, CA (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 16/063,201

(22) PCT Filed: Dec. 17, 2016

(86) PCT No.: PCT/US2016/067404
§ 371 (c)(1),
(2) Date: Jun. 15, 2018

(87) PCT Pub. No.: WO2017/106803
PCT Pub. Date: Jun. 22, 2017

(65) Prior Publication Data
US 2018/0370892 A1 Dec. 27, 2018

Related U.S. Application Data

(60) Provisional application No. 62/269,016, filed on Dec. 17, 2015.

(51) Int. Cl.
| | |
|---|---|
| *C07C 50/28* | (2006.01) |
| *C07C 50/24* | (2006.01) |
| *A61P 39/06* | (2006.01) |
| *C07C 225/24* | (2006.01) |
| *C07C 317/04* | (2006.01) |
| *C07D 213/65* | (2006.01) |
| *C07D 295/108* | (2006.01) |

(52) U.S. Cl.
CPC .............. *C07C 50/28* (2013.01); *A61P 39/06* (2018.01); *C07C 50/24* (2013.01); *C07C 225/24* (2013.01); *C07C 317/04* (2013.01); *C07D 213/65* (2013.01); *C07D 295/108* (2013.01)

(58) Field of Classification Search
CPC .................................. C07C 50/28; A61P 39/06
See application file for complete search history.

(56) References Cited

U.S. PATENT DOCUMENTS

| | | |
|---|---|---|
| 2,398,418 A | 4/1946 | Fieser |
| 2,856,414 A | 10/1958 | Robeson et al. |
| 3,071,512 A | 1/1963 | Feldmann |
| 3,406,188 A | 10/1968 | Fletcher |
| 3,705,239 A | 12/1972 | Gregory |
| T917,001 I4 | 12/1973 | Anderson, Jr. et al. |
| 3,849,453 A | 11/1974 | Morrimoto et al. |
| 3,896,153 A | 7/1975 | Sato et al. |
| 3,909,376 A | 9/1975 | Degner |
| 3,957,836 A | 5/1976 | Morimoto et al. |
| 4,127,608 A | 11/1978 | Olson et al. |
| 4,153,614 A | 5/1979 | Barner et al. |
| 4,185,154 A | 1/1980 | Olson et al. |
| 4,201,726 A | 5/1980 | Olson et al. |
| 4,201,879 A | 5/1980 | Barner et al. |
| 4,234,490 A | 11/1980 | Barner et al. |
| 4,243,598 A | 1/1981 | Olson et al. |
| 4,310,465 A | 1/1982 | Olson et al. |
| 4,388,312 A | 6/1983 | Terao et al. |
| 4,393,075 A | 7/1983 | Terao et al. |
| 4,436,753 A | 3/1984 | Imada et al. |
| 4,491,594 A | 1/1985 | Ogawa et al. |
| 4,495,104 A | 1/1985 | Imada et al. |
| 4,559,177 A | 12/1985 | Okutani et al. |
| 4,559,407 A | 12/1985 | Barner et al. |
| 4,592,867 A | 6/1986 | Yu et al. |
| 4,599,232 A | 7/1986 | Bertelli |

(Continued)

FOREIGN PATENT DOCUMENTS

| | | |
|---|---|---|
| CA | 2430415 | 6/2002 |
| CN | 1441793 | 9/2003 |

(Continued)

OTHER PUBLICATIONS

Alexander, C. et al. (Oct. 2000). "OPA1, Encoding a Dynamin-Related GTPase, is Mutated in Autosomal Dominant Optic Atrophy Linked to Chromosome 3q28," Nature Genetics 26(2):211-215.

Balci, M. et al., "Product subclass 7: benzo-1,4-quinones substituted with carbon with one bond to heteroatom", Science of Synthesis, 2006, vol. 28, No. 1, pp. 115-130.

Borovkov, V. V. et al., "Synthesis of deuteroporphyrin IX diquinone derivatives for studies of primary photosynthetic stages", Khimiya Geterotsiklicheskikh Soedinenii, 1992, vol. 2, pp. 176-182; with an English abstract.

Compound with CAS Registry No. 939125-87-8, published Jun. 26, 2007, 1 page.

Crozet, M. P. et al., "Fluoride as Leaving Group in SRN1 reactions of a tetrasubstituted-1,4-benzoquinone", Tetrahedron Letters, 1992, vol. 33, No. 8, pp. 1063-1064.

(Continued)

*Primary Examiner* — Golam M Shameem
(74) *Attorney, Agent, or Firm* — Squire Patton Boggs (US) LLP

(57) ABSTRACT

Disclosed herein are compounds and methods of using such compounds for treating or suppressing oxidative stress disorders, including mitochondrial disorders, impaired energy processing disorders, neurodegenerative diseases and diseases of aging, or for modulating one or more energy biomarkers, normalizing one or more energy biomarkers, or enhancing one or more energy biomarkers, wherein the compounds are tocopherol quinone derivatives. Further disclosed are compounds, compositions, and methods for treatment of, or prophylaxis against, radiation exposure.

23 Claims, No Drawings

(56) References Cited

U.S. PATENT DOCUMENTS

| | | | |
|---|---|---|---|
| 4,617,317 A | 10/1986 | Bennet | |
| 4,694,090 A | 9/1987 | Shiono et al. | |
| 4,804,539 A | 2/1989 | Guo et al. | |
| 4,814,346 A | 3/1989 | Albert et al. | |
| 4,818,441 A | 4/1989 | Imada et al. | |
| 4,831,265 A | 5/1989 | Watanabe et al. | |
| 4,883,658 A | 11/1989 | Holly | |
| 4,914,088 A | 4/1990 | Glonek et al. | |
| 5,057,514 A | 10/1991 | Tatsuoka et al. | |
| 5,059,627 A | 10/1991 | Goto et al. | |
| 5,075,104 A | 12/1991 | Gressel et al. | |
| 5,157,132 A | 10/1992 | Tan et al. | |
| 5,179,092 A | 1/1993 | Tatsuoaka et al. | |
| 5,180,742 A | 1/1993 | Terao et al. | |
| 5,190,618 A | 3/1993 | Top et al. | |
| 5,210,239 A | 5/1993 | Abe et al. | |
| 5,229,385 A | 7/1993 | Terao et al. | |
| 5,278,151 A | 1/1994 | Korb et al. | |
| 5,288,752 A | 2/1994 | Tatsuoka et al. | |
| 5,292,768 A | 3/1994 | Tatsuoka et al. | |
| 5,294,607 A | 3/1994 | Glonek et al. | |
| 5,304,658 A | 4/1994 | Terao et al. | |
| 5,371,108 A | 12/1994 | Korb et al. | |
| 5,547,827 A | 8/1996 | Chen et al. | |
| 5,563,129 A | 10/1996 | Masuya et al. | |
| 5,600,029 A | 2/1997 | Kaneko et al. | |
| 5,801,159 A | 9/1998 | Miller et al. | |
| 5,846,988 A | 12/1998 | Hellberg | |
| 5,872,108 A | 2/1999 | Sandage, Jr. et al. | |
| 5,874,461 A | 2/1999 | De Chaffoy De Courcelles et al. | |
| 5,886,030 A | 3/1999 | Maniar | |
| 5,969,133 A | 10/1999 | Ono et al. | |
| 5,981,601 A | 11/1999 | Nagley et al. | |
| 6,011,046 A | 1/2000 | Ohkawa et al. | |
| 6,045,826 A | 4/2000 | Borowy-Borowski et al. | |
| 6,083,982 A | 7/2000 | Wechter et al. | |
| 6,133,278 A | 10/2000 | Terao et al. | |
| 6,133,322 A | 10/2000 | Rustin et al. | |
| 6,136,859 A | 10/2000 | Henrikesen | |
| 6,150,402 A | 11/2000 | Wechter et al. | |
| 6,187,811 B1 | 2/2001 | Lane | |
| 6,232,060 B1 | 5/2001 | Miller et al. | |
| 6,239,171 B1 | 5/2001 | Lane et al. | |
| 6,271,266 B1 | 8/2001 | Miyamoto et al. | |
| 6,297,281 B1 | 10/2001 | Chabier De Lassauniere et al. | |
| 6,300,377 B1 | 10/2001 | Chopra | |
| 6,331,532 B1 | 12/2001 | Muprhy et al. | |
| 6,342,516 B1 | 1/2002 | Umeda et al. | |
| 6,395,915 B1 | 5/2002 | Bellafiore et al. | |
| 6,417,233 B1 | 7/2002 | Sears et al. | |
| 6,426,362 B1 | 7/2002 | Miller et al. | |
| 6,433,199 B1 | 8/2002 | Ono et al. | |
| 6,454,184 B1 | 9/2002 | Merkel et al. | |
| 6,472,378 B2 | 10/2002 | Von Borstel | |
| 6,528,042 B1 | 3/2003 | Brown et al. | |
| 6,545,184 B1 | 4/2003 | Lipshutz | |
| 6,562,372 B1 | 5/2003 | Yokoi et al. | |
| 6,608,196 B2 | 8/2003 | Wang et al. | |
| 6,653,346 B1 | 11/2003 | Wang et al. | |
| 6,656,358 B2 | 12/2003 | May et al. | |
| 6,740,338 B1 | 5/2004 | Chopra | |
| 6,764,768 B2 | 7/2004 | Mrksich et al. | |
| 6,838,104 B2 | 1/2005 | Jacobs | |
| 6,852,895 B2 | 2/2005 | Lipshutz et al. | |
| 6,977,270 B2 | 12/2005 | Baldenius et al. | |
| 7,034,054 B2 | 4/2006 | Miller et al. | |
| 7,038,067 B2 | 5/2006 | Couladouros et al. | |
| 7,078,541 B2 | 7/2006 | Boddupalli et al. | |
| 7,118,688 B2 | 10/2006 | Mora-Gutierrez et al. | |
| 7,119,117 B2 | 10/2006 | Beinlich et al. | |
| 7,393,662 B2 | 7/2008 | Heavner et al. | |
| 7,470,798 B2 | 12/2008 | Wang et al. | |
| 7,491,312 B2 | 2/2009 | Gilat et al. | |
| 7,514,461 B2 | 4/2009 | Wang et al. | |
| 7,718,176 B2 | 5/2010 | Heavner et al. | |
| 7,875,607 B2 | 1/2011 | Wang et al. | |
| 7,968,746 B2 | 6/2011 | Jankowski et al. | |
| 8,044,097 B2 | 10/2011 | Wang et al. | |
| 8,106,223 B2 | 1/2012 | Wesson et al. | |
| 8,182,990 B2 | 5/2012 | Mashima et al. | |
| 8,314,153 B2 | 11/2012 | Miller et al. | |
| 8,394,392 B2 | 3/2013 | Imahashi et al. | |
| 8,575,369 B2 | 11/2013 | Wesson et al. | |
| 8,653,144 B2 | 2/2014 | Miller et al. | |
| 8,716,486 B2 | 5/2014 | Hinman et al. | |
| 8,716,527 B2 | 5/2014 | Hinman et al. | |
| 8,791,155 B2 | 7/2014 | Wang et al. | |
| 9,061,962 B2 * | 6/2015 | Ronsin | C07C 203/04 |
| 9,073,873 B2 * | 7/2015 | Hinman | C07D 213/74 |
| 9,090,576 B2 * | 7/2015 | Hinman | C07C 45/00 |
| 9,629,815 B2 * | 4/2017 | Shrader | A61K 31/05 |
| 2001/0044462 A1 | 11/2001 | Hensley et al. | |
| 2002/0032171 A1 | 3/2002 | Chen et al. | |
| 2002/0132845 A1 | 9/2002 | Miller et al. | |
| 2002/0143049 A1 | 10/2002 | Miller et al. | |
| 2002/0182196 A1 | 12/2002 | McCleary | |
| 2003/0022818 A1 | 1/2003 | Miller et al. | |
| 2003/0119054 A1 | 6/2003 | Mrksich et al. | |
| 2003/0134028 A1 | 7/2003 | Lievense | |
| 2003/0144219 A1 | 7/2003 | Phinney et al. | |
| 2003/0158237 A1 | 8/2003 | Saragovi et al. | |
| 2004/0043013 A1 | 4/2004 | McCleary et al. | |
| 2004/0063661 A1 | 4/2004 | Linnane | |
| 2004/0105817 A1 | 6/2004 | Gilat et al. | |
| 2004/0156871 A1 | 8/2004 | Borowy-Borowski et al. | |
| 2004/0241628 A1 | 12/2004 | Thomas et al. | |
| 2005/0043553 A1 | 2/2005 | Smith et al. | |
| 2005/0049227 A1 | 3/2005 | Old et al. | |
| 2005/0065099 A1 | 3/2005 | Walkinshaw et al. | |
| 2005/0065149 A1 | 3/2005 | Wang et al. | |
| 2005/0065150 A1 | 3/2005 | Wang et al. | |
| 2005/0186518 A1 | 8/2005 | Masskasky et al. | |
| 2005/0203066 A1 | 9/2005 | Von Borstel | |
| 2005/0222218 A1 | 10/2005 | Meier et al. | |
| 2005/0234248 A1 | 10/2005 | Kossler et al. | |
| 2005/0256186 A1 | 11/2005 | Morishige | |
| 2006/0002885 A1 | 1/2006 | Mielke et al. | |
| 2006/0051844 A1 | 3/2006 | Heavner et al. | |
| 2006/0241174 A1 | 10/2006 | Mueller et al. | |
| 2006/0281809 A1 | 12/2006 | Miller et al. | |
| 2007/0066541 A1 | 3/2007 | Hughes et al. | |
| 2007/0072943 A1 | 3/2007 | Miller et al. | |
| 2007/0135335 A1 | 6/2007 | Collier et al. | |
| 2007/0180544 A1 | 8/2007 | Palmer et al. | |
| 2007/0225261 A1 | 9/2007 | Miller et al. | |
| 2007/0248590 A1 | 10/2007 | Milne et al. | |
| 2008/0093985 A1 | 4/2008 | Morishita et al. | |
| 2008/0132568 A1 | 6/2008 | Thompson et al. | |
| 2008/0213239 A1 | 9/2008 | Morris | |
| 2008/0221050 A1 | 9/2008 | Mashima | |
| 2009/0036542 A1 | 2/2009 | Luu et al. | |
| 2009/0042980 A1 | 2/2009 | Lipton et al. | |
| 2009/0060981 A1 | 3/2009 | Chauhan | |
| 2009/0162890 A1 | 6/2009 | Gilat et al. | |
| 2009/0163529 A1 | 6/2009 | Gilat et al. | |
| 2009/0192179 A1 | 7/2009 | Wang et al. | |
| 2009/0291092 A1 | 11/2009 | Miller et al. | |
| 2010/0010100 A1 | 1/2010 | Hinman et al. | |
| 2010/0029706 A1 | 2/2010 | Miller et al. | |
| 2010/0029784 A1 | 2/2010 | Hinman et al. | |
| 2010/0056429 A1 | 3/2010 | Miller et al. | |
| 2010/0063161 A1 | 3/2010 | Miller et al. | |
| 2010/0093845 A1 | 4/2010 | Wong et al. | |
| 2010/0105930 A1 | 4/2010 | Wesson et al. | |
| 2010/0222436 A1 | 9/2010 | Miller et al. | |
| 2010/0227879 A1 | 9/2010 | Mudumba et al. | |
| 2010/0249032 A1 | 9/2010 | Heavner et al. | |
| 2010/0266591 A1 | 10/2010 | Bugelski et al. | |
| 2010/0273892 A1 | 10/2010 | Miller et al. | |
| 2010/0273894 A1 | 10/2010 | Miller | |
| 2011/0027397 A1 | 2/2011 | Theoharides | |
| 2011/0046156 A1 | 2/2011 | Miller | |
| 2011/0046219 A1 | 2/2011 | Hinman et al. | |
| 2011/0124679 A1 | 5/2011 | Hinman et al. | |

(56) References Cited

U.S. PATENT DOCUMENTS

| | | |
|---|---|---|
| 2011/0142834 A1 | 6/2011 | Miller |
| 2011/0172312 A1 | 7/2011 | Miller et al. |
| 2011/0183019 A1 | 7/2011 | Theoharides |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0088783 A1 | 4/2012 | Wang et al. |
| 2012/0101169 A1 | 4/2012 | Hawi |
| 2012/0122934 A1 | 5/2012 | Jankowski et al. |
| 2012/0122969 A1 | 5/2012 | Miller et al. |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0189343 A1 | 7/2013 | Krumme et al. |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0039065 A1 | 2/2014 | Miller |
| 2014/0206772 A1 | 7/2014 | Miller et al. |
| 2014/0206905 A1 | 7/2014 | Schiefer et al. |
| 2014/0221674 A1 | 8/2014 | Wesson et al. |
| 2014/0243424 A1 | 8/2014 | Mollard et al. |
| 2014/0249332 A1 | 9/2014 | Mollard |
| 2014/0275045 A1 | 9/2014 | Hinman et al. |
| 2014/0275054 A1 | 9/2014 | Hinman et al. |
| 2015/0057363 A1 | 2/2015 | Miller et al. |
| 2015/0125526 A1 | 5/2015 | Rioux et al. |
| 2015/0209430 A1 | 7/2015 | Suzanne et al. |
| 2015/0216820 A1 | 8/2015 | Miller et al. |
| 2015/0218079 A1 | 8/2015 | Shrader et al. |
| 2015/0297551 A1 | 10/2015 | Hinman et al. |
| 2016/0022607 A1 | 1/2016 | Krause et al. |
| 2016/0024085 A1 | 1/2016 | Hinman et al. |
| 2016/0039775 A1 | 2/2016 | Hinman et al. |
| 2016/0039776 A1 | 2/2016 | Hinman et al. |
| 2016/0115141 A1 | 4/2016 | Hinman et al. |
| 2016/0186264 A1 | 6/2016 | McKernan et al. |
| 2017/0247674 A1 | 8/2017 | Boisvert et al. |
| 2018/0000749 A1 | 1/2018 | Mollard et al. |
| 2018/0002247 A1 | 1/2018 | Mollard et al. |
| 2018/0117026 A1 | 5/2018 | DeWitt et al. |
| 2018/0250208 A1 | 9/2018 | Boice et al. |
| 2018/0305328 A1 | 10/2018 | Beyrath et al. |
| 2019/0062272 A1 | 2/2019 | Chimmanamada et al. |

FOREIGN PATENT DOCUMENTS

| | | |
|---|---|---|
| DE | 38 18 696 | 3/1989 |
| EP | 0025692 A1 | 3/1981 |
| EP | 0065368 A1 | 11/1982 |
| EP | 0107806 A1 | 5/1984 |
| EP | 0107806 B1 | 5/1984 |
| EP | 0 134 198 | 3/1985 |
| EP | 0326987 A2 | 8/1989 |
| EP | 0326987 A3 | 8/1989 |
| EP | 0 619 313 | 10/1994 |
| EP | 0629400 A1 | 12/1994 |
| EP | 0 719 552 | 12/1995 |
| EP | 1 378 753 | 1/2004 |
| EP | 1611879 A1 | 1/2006 |
| FR | 1 201 200 | 12/1959 |
| FR | 75631 | 7/1961 |
| FR | 5531 | 11/1967 |
| FR | 1 536 576 | 8/1968 |
| JP | 40-9029 | 5/1965 |
| JP | 48-75564 A | 10/1973 |
| JP | 49-88862 A | 8/1974 |
| JP | 52-111576 A | 9/1977 |
| JP | 52-130922 | 11/1977 |
| JP | 56-140943 | 11/1981 |
| JP | 57-050935 | 3/1982 |
| JP | 58-018374 | 2/1983 |
| JP | 58-083698 | 5/1983 |
| JP | 58-193689 | 11/1983 |
| JP | 60-28919 A | 2/1985 |
| JP | 60-056902 A | 4/1985 |
| JP | 60-197621 | 10/1985 |
| JP | 61-040236 A | 2/1986 |
| JP | 63-063674 A | 3/1988 |
| JP | 1 093 554 | 4/1989 |
| JP | 1 209 445 | 8/1989 |
| JP | 1 233 278 A | 9/1989 |
| JP | 5-11467 | 1/1993 |
| JP | 8092151 | 4/1996 |
| JP | 2000-202297 | 7/2000 |
| JP | 2003-64017 | 3/2003 |
| JP | 2003-137716 | 5/2003 |
| WO | WO 1993/24650 | 12/1993 |
| WO | WO 1998/34646 | 8/1998 |
| WO | WO 99/25336 | 5/1999 |
| WO | WO 1999/38860 A1 | 8/1999 |
| WO | WO 2000/35444 A1 | 6/2000 |
| WO | WO 2000/50043 | 8/2000 |
| WO | WO 2000/78296 A2 | 12/2000 |
| WO | WO 2000/78296 A3 | 12/2000 |
| WO | WO 2001/52822 | 7/2001 |
| WO | WO 2001/92215 | 12/2001 |
| WO | WO 2002/006261 A1 | 12/2001 |
| WO | WO 2002/30419 A1 | 4/2002 |
| WO | WO 2002/34259 | 5/2002 |
| WO | WO 02/43507 A2 | 6/2002 |
| WO | WO 02/43507 A3 | 6/2002 |
| WO | WO 02/47680 A2 | 6/2002 |
| WO | WO 02/47680 A3 | 6/2002 |
| WO | WO 02/47680 A9 | 6/2002 |
| WO | WO 2002/50054 A2 | 6/2002 |
| WO | WO 2002/50054 A3 | 6/2002 |
| WO | WO 2002/067864 | 9/2002 |
| WO | WO 03/064403 | 8/2003 |
| WO | WO 2003064403 A1 | 8/2003 |
| WO | WO 2004/003565 | 1/2004 |
| WO | WO 2004/042353 | 5/2004 |
| WO | WO 2005/000357 | 1/2005 |
| WO | WO 2005/013911 A2 | 2/2005 |
| WO | WO 2005/013911 A3 | 2/2005 |
| WO | WO 2005/019232 | 3/2005 |
| WO | WO 2005/032544 | 4/2005 |
| WO | WO 2005/033092 | 4/2005 |
| WO | WO 2005/033093 | 4/2005 |
| WO | WO 2005090602 A2 | 9/2005 |
| WO | WO 2005/105159 | 11/2005 |
| WO | WO 2007/035496 A1 | 3/2007 |
| WO | WO 2007/095630 | 8/2007 |
| WO | WO 2008/086025 | 7/2008 |
| WO | WO 2008/142433 A1 | 11/2008 |
| WO | WO 2008/157747 A1 | 12/2008 |
| WO | WO 2010/128038 A1 | 11/2010 |
| WO | WO 2011/041452 A2 | 4/2011 |
| WO | WO 2011/113018 A1 | 9/2011 |
| WO | WO 2012/019029 A2 | 2/2012 |
| WO | WO 2012/019029 A3 | 2/2012 |
| WO | WO 2012/019032 A1 | 2/2012 |
| WO | WO 2012/154613 A1 | 11/2012 |
| WO | WO 2012/170773 A1 | 12/2012 |
| WO | WO 2013/006736 A1 | 1/2013 |
| WO | WO 2013/110442 A1 | 8/2013 |
| WO | WO 2015/183963 A2 | 12/2015 |
| WO | WO 2015/183984 A2 | 12/2015 |
| WO | WO 2016/114860 | 7/2016 |
| WO | WO 2017/087795 A1 | 5/2017 |
| WO | WO 2017/106803 | 6/2017 |
| WO | WO 2017/123823 | 7/2017 |
| WO | WO 2018/081644 A1 | 5/2018 |

(56) References Cited

FOREIGN PATENT DOCUMENTS

| | | |
|---|---|---|
| WO | WO 2018/093957 A1 | 5/2018 |
| WO | WO 2018/129411 A1 | 7/2018 |

OTHER PUBLICATIONS

Crozet, M. P. et al., "$S_{RN}1$ Reactions of a Tetrasubstituted-1,4-Benzoquinone", Tetrahedron Letters, 1991, vol. 32, No. 33, pp. 4125-4128.
Giraud, A. et al., "Stereoselective hetero-Diels—Alder reactions: structure determination of new xanthenedione derivatives by NMR spectroscopy and x-ray crystallography", Magnetic Resonance in Chemistry, 1999, vol. 37, No. 1, pp. 77-81.
Giraud, L. et al., "Diels—Alder Trapping of ortho-Quinone Methides. A New Entry to Substituted Xanthene-1,4-diones", Synthesis, Aug. 1998, vol. 8, pp. 1153-1160.
Kajiwara, M. et al., "Studies on Tocopherols II.sup.1 . Convenient Synthesis of Tocopherols," Heterocycles, 1980, vol. 14, No. 12, pp. 1995-1998.
Lewis, J.S. et al. (Apr. 2001). "Tumor Uptake of Copper-Diacetyl-Bis(N4-Methylthiosemicarbazone): Effect of Changes in Tissue Oxygenation," The Journal of Nuclear Medicine 42(4):655-661.
Novak, L. et al., "Rearrangement of Allyl Aryl Ethers I. Reaction of Hydroquinone with Conjugated Dien-ols and Trien-ol", Tetrahedron, 1995, vol. 51, No. 34, pp. 9367-9374.
Novak, L. et al., "Rearrangement of Allyl Aryl Ethers Ii; Reaction of Hydroquinone with Cycloalkenediols", Synthesis, Aug. 1997, vol. 8, pp. 909-916.
Rasool, N. et al., "A Benzoquinone and a Coumestan From Psoralea Plicata", Phytochemistry, 1991, vol. 30, No. 8, pp. 2800-2803.
Rathore, R. et al., "Acid Catalysis vs. Electron-Transfer Catalysis via Organic Cations or Cation-Radicals as the Reactive Intermediate. Are These Distinctive Mechanisms?", 1998, Acta Chemica Scandinavica, vol. 52, pp. 114-130.
Rathore, R. et al., "Radical-Cation Catalysis in the Synthesis of Diphenylmethanes via the Dealkylative Coupling of Benzylic Ethers", J. Org. Chem., 1995, vol. 60, pp. 7479-7490.
Rathore, R. et al., "Selective Nitration versus Oxidative Dealkylation of Hydroquinone Ethers with Nitrogen Dioxide", Tetrahedron, 1994, vol. 50, No. 23, pp. 6727-6758.
Van Haaften, R. I. M. et al., "Inhibition of human glutathione S-transferase P1-1 by tocopherols and α-tocopherol derivatives", Biochimica et Biophysica Acta, 2001, vol. 1548, pp. 23-28.
1957:81330 CAPLUS, Weichet et al., "Studies in the vitamin K and E series, III, Analogs of a-tocopherol with unbranched sidechains", 1 page.
202843-61-6 Registry, Mar. 19, 1998, 2,5-Cyclohexadiene-1,4-dione, 2,3,5-trimethyl-6-[(2E)-3-methyl-2-nonen-1-yl], 1 page.
82925-41-5 Registry, Nov. 16, 1984, 1,4-Benzenediol, 2,3,5-trimethyl-6-(3-methyl-2-nonadeceri-1-yl), 1 page.
Adelwohrer, C. et al. (2005, e-pub. Aug. 2, 2005). "Novel Tocopheryl Compounds XX. 1,3,8-Trioxaphenanthrenes Derived from y-Tocopherol," Tetrahedron 61:9070-9074.
Al-Gadani, Y. et al. (2009, e-pub. Mar. 21, 2009). "Metabolic Biomarkers Related to Oxidative Stress and Antioxidant Status in Saudi Autistic Children," Clinical Biochemistry 42(1011):1032-1040.
Altaweel, Best Disease: Treatment & Medication, www.emedicine.com, Feb. 11, 2010, printed from http://emedicine.medscape.com/article/1227128-treatment, 2 pages.
Anderson et al. "No evidence for altered muscle mitochondrial function in Parkinson's disease," Journal of Neurology, Neurosurgery, and Psychiatry, 1993, vol. 56, pp. 477-480.
Angley, M. et al. (Sep. 2007). "Children and Autism. Part 1—Recognition and Pharmacological Management," Australian Family Physician 36(9):741-744.
Anonymous (1976), "028 CGI Clinical Global Impressions," in Early Clinical Drug Evaluation Unit (ECDEU) Assessment Manual for Psychopharmacology, U.S. Department of Health, Education, and Welfare, pp. 217-222.
Anonymous (2006), "Mitochondrial Dysfunction Contribution to Bipolar Disorder Confirmed Using Model Mice," Press Release from Riken Brain Science Institute located at http://web.archive.org/web/2012030316199/htto://www.riken.ip/enon/r-world/infor/pressrelease/press/2006/060418/index.html, last visited Feb. 10, 2015, 5 pages.
Anonymous (Feb. 2010). "List of Publications Noting Mitochondrial Involvement in Diseases," 3 Pages.
Anonymous, "Leigh Syndrome", NORD, located at http://rarediseases.org/rare-diseases/leigh-syndrome, the site was last visited on May 12, 2016, 14 pages.
Anonymous, ICD-10 Version: 2015, "Other specified degenerative diseases of nervous system" located at http://apps.who.int/classifications/icd10/browse/2015/en#/G31.8, the site was last visited on May 12, 2016, 1 page.
Anonymous, Leigh syndrome—Genetics Home Reference, "Other Names for This Condition" located at https://ghr.nlm.nih.gov/condition/leigh-syndrome, the site was last visited on May 12, 2016, 8 pages.
Anonymous. (2011). "Mitochondrial Myopathy," located at http://www.ninds.nih.gov/disorders/mitochondrial_myopathy/mitochondrial_myopathy.html, last visited Feb. 10, 2015, 2 pages.
Ansell et al. "The Pharmacology and Management of the Vitamin K Antagonists," Chest, 126(3), Supplement p. 204S-233S, 2004.
Antalis, C.J. et al. (2006). "High Dietary Alpha Tocopherol Improves Attention Deficit/Hyperactivity (ADHD)-Like Behavior in Juvenile Spontaneously Hypertensive Rats (SHR)," FASEB Journal 20(5): A1002-A1003, Abstract.
Armstrong, J.S. et al. (Dec. 5, 2003). "The Coenzyme Clio Analog Decylubiquinone Inhibits the Redox-Actived Mitochondrial Permeability Transition," The Journal of Biological Chemistry 278(49):49079-49084.
Asgill, J.O. et al. (Jan. 4, 1978). "Chromenylation of 2-Napthol and Alkylhydroquinones: Short Synthesis of (2RS,4'R, 8'R)-alpha-Tocopherol (Vitamin E) and (2RS,4'R, 8TR)-(3 Tocopherol," The Journal of the Chemical Society Chemical Communications 1:59-60.
Asin-Cayuela, J. et al. (Jul. 30, 2004). "Fine-Tuning the Hydrophobicity of a Mitochondria-Targeted Antioxidant," FEBS Letters 571(1-3):9-16.
Barbiroli, B. et al. (Jul. 1995). "Lipoic (Thioctic) Acid Increases Brain Energy Availability and Skeletal Muscle Performance as Shown by In Vivo 31 P-MRS in a Patient with Mitochondrial Cytopathy," Journal of Neurology 242(7):472-477.
Beers, M.H. ed. etal. (1999). "Cerebrovascular Disease," Chapter 174 in The Merck Manual of Diagnosis and Therapy, 17th Edition, Merck Research Laboratories, Whitehouse Station, NJ, pp. 1417-1424.
Bentinger, M. et al. (2008). "Stimulation of Coenzyme Q Synthesis," BioFactors 32, pp. 99-111.
Bentinger, M. et al. (May 23, 2008). "Polyisoprenoid Epoxides Stimulate the Biosynthesis of Coenzyme Q and Inhibit Cholesterol Synthesis," The Journal of Biological Chemistry, vol. 283, No. 21, pp. 14645-14653.
Bernas T. et al. (2002). "Mitochondrial and Nonmitochondrial Reduction of MTT: Interaction of MTT With TMRE, JC-1, and NAO Mitochondrial Fluorescent Probes," Cytometry 47:236-242.
Berridge M. et al. (2005). "Tetrazolium dyes as tools in cell biology: New insights into their cellular reduction," Biotechnology Annual Review 11:127-152.
Bertalan L. et al. (2000). "Recovery of fatty oil from the Transylvanian black current by means of supercritical and conventional extraction," Olaf, szappn Kozmetika 49(Kulonszam), pp. 40-45.
Bertamini, M. et al. (2002). "Mitochondrial Oxidative Metabolism in Motor Neuron Degeneration (mnd) Mouse Central Nervous System," European Journal of Neuroscience 16(12):2291-2296.
Bilenko, M.V. et al. (Sep. 1983). "Use of Antioxidants to Prevent Damage During Acute Ischemia and Reperfusion of the Kidneys," Byulleten'Eksperimental'noi Biologii i Meditsiny 96(9):8-11. (Abstract only).
Biousse et al. (Feb. 2003). "Neuro-Ophthalmology of Mitochondrial Diseases," Current Opinion in Neurology, 16(1):35-43.

(56) References Cited

OTHER PUBLICATIONS

Blankenberg et al., "Brain uptake of Tc99m-HMPAO correlates with clinical response to the novel redox modulating agent EPI-743 in patients with mitochondrial disease," Molecular Genetics and Metabolism, 2012, vol. 107, pp. 690-699.
Boyer, P.D. (Feb. 19, 1951). "The Preparation of Reversible Oxidation Product of a-Tocopherol, a-Tocopheroxide and of Related Oxides," *Journal of the American Chemical Society* 73(2):733-740.
Bremner, F.D. (2004). "Pupil Assessment in Optic Nerve Disorders," Eye 18:1175-1181.
Brigelius-Flohe, R. et al. (Jul. 1999). "Vitamin E: Function and Metabolism," The FASEB Journal, vol. 13, No. 10, pp. 1145-1155.
Briere, J-J. et al. (Apr. 16, 2004). "Quinone Analogues Regulate Mitochondrial Substrate Competitive Oxidation," *Biochemical and Biophysical Research Communications* 316(4):11381142.
Brown, M.D. et al. (Jul. 1992). "Leber's Hereditary Optic Neuropathy: A Model for Mitochondrial Neurodegenerative Diseases," The FASEB Journal 6:2791-2799.
Buranrat et al. (2012). "NQO1 Expression Correlates with Cholangiocarcinoma Prognosis," Asian Pacific J. Cancer Prev. 13:131-136.
Butterfield, D.A. et al. (2002). "Vitamin E and Neurodegenerative Disorders Associated with Oxidative Stress," Nutritional Neuroscience 5(4):229-239.
Calabresi P. and Chabner BA, "Section IX Chemotherapy of Neoplastic—Introduction," Goodman Gillman's the Pharmacological Basis of Therapeutics 10th ed., 2001, Hardman JG, Limbird LE, and Gilman AG, Eds., McGraw-Hill, New York 2001, pp. 1381-1388 (pp. 1-3 and 1381-1388 provided).
Calviello, G. et al. (2003). "γ Tocopheryl Quinone Inducs Apoptosis in Cancer Cells Via Caspase-9 Activation and Cytochrome c Release" *Carcinogenesis* 24(3):427-433.
Canter, J.A. et al. (May 2008). "Mitochondrial DNA Polymorphism A4917G Is Independently Associated with Age-Related Macular Degeneration," PloS One 3(5):e2091, 4 pages.
Caplus Accession No. 169:524242, created May 12, 1984, 3 pages.
Caplus Accession No. 1967:18647, created May 12, 1984, 9 pages.
Caplus Accession No. 1969:433438, created May 12, 1984, 1 page.
Caplus Accession No. 1989:553350, created Oct. 28, 1999, 4 pages.
Caplus Accession No. 2003:166979, created Mar. 5, 2003, 5 pages.
Caplus Accession No. 2003:487787, created Jun. 27, 2003, 8 pages.
Carelli, V. (2002). "Optic Nerve Degeneration and Mitochondrial Dysfunction: Genetic and Acquired Optic Neuropathies," Neurochemistry International 40:573-584.
Carelli, V. et al. (2009, e-pub. Mar. 5, 2009). "Retinal Ganglion Cell Neurodegeneration in Mitochondrial Inherited Disorders," Biochimica et Biophysica Acta 1787:518-528.
Cassels, C. (Apr. 15, 2008, updated Apr. 25, 2008). "Mitochondrial Dysfunction May Play a Role in Autism Spectrum Disorders Etiology," Medscape Press Release, located at http://www.medscape.com/viewarticle/573004, 2 pages.
Catlin Joseph C et al: "New Hydroquinones, Apparent Inhibitors of Coenzyme Q Enzyme Systems", Journal of the American Chemical Society, Jun. 19, 1968 (Jun. 19, 1968), pp. 3572-3574, XP55065560, Retrieved from the Internet: URL: httpgil_pubs.acs.oratdoilpal 0.1021lia01015a054 [retrieved on Jun. 6, 2013].
Chariot, P. et al. (Apr. 1994). "Determination of the Blood Lactase: Pyruvate Ratio as a Noninvasive Test for the Diagnosis of Zidovudine Myopathy," *Arthritis & Rheumatism* 37(4):583-586.
Chariot, P. et al. (Jul. 1994). "Optimal Handling of Blood Samples for Routine Measurement of Lactate and Pyruvate," *Archives of Pathology & Laboratory Medicine* 118(7):695-697.
Chauhan, A. et al. (Aug. 1, 2006). "Oxidative Stress in Autism," *Pathophysiolog* 13(3):171-181.
Chez et al., "Double-Blind, Placebo-Controlled Study of L-Carnosine Supplementation in Children With Autistic Spectrum Disorders", *Journal of Child Neurology*, vol. 17, No. 11, Nov. 2002, pp. 833-837.
Choi, D.W. (Oct. 1988). "Glutamate Neurotoxicity and Diseases of the Nervous System," Neuron. 1(8):623-634.
Chow, C.K. et al. (Sep. 1967). "The Metabolism of C14-alpha-Tocopheryl Quinone and C14-alpha-Tocopheryl Hydroquinone," Lipids 2(5):390-396.
Christen et al. (Apr. 1997). "γ-Tocopherol Traps Mutagenic Electrophiles Such as NOX and Complements α-Tocopherol: Physiological Implications," Proc. Natl. Acad. Sci. USA 94(7):3217-3222.
Chugani, D.C. et al. (May 1999). "Evidence of Altered Energy Metabolism in Autistic Children," *Progress in Neuro-Psychopharmacology & Biological Psychiatry* 23(4):635-641.
Cichewicz, R.H. et al. (2004, e-pub. Oct. 23, 2004). "Redox Inactivation of Human 15-Liopsygenase by Marine-Derived Meroditerpenes and Synthetic Chromanes: Archetypes for a Unique Class of Selective and Recyclable Inhibitors," Journal of the American Chemical Society 126(45):14910-14920.
Cohen, N. et al. (1981). "Studies on the Total Synthesis of (2R,4'R,8'R)-alpha-Tocopherol (Vitamin E). Stereospecific Cyclizations Leading to Optically Active Chromans," *The Journal of Organic Chemistry* 46(12):2445-2450.
Coleman, M. et al. (Mar. 1985). "Autism and Lactic Acidosis," *Journal of Autism and Developmental Disorders* 15(1):1-8.
Cornwell, D.G. et al. (1998). "Cytotoxicity of Tocopherols and Their Quinones in Drug-Sensitive and Multidrug-Resistant Leukemia Cells," Lipids 33(3):295-301.
Cressman et al. "One-Step Synthesis of Polyalkyl-2-iodo-p-benzoquinones", *Journal of Organic Chemistry*, 1966, 31 (4), pp. 1279-1281.
Csaky, K.G. (Mar./Apr. 2007). "New Developments in the Transscleral Delivery of Ophthalmic Agents," Retina Today, pp. 32-35.
Dearling et al. (Mar. 2002, e-pub. Sep. 8, 2001). "Copper Bis(Thiosemicarbazone) Complexes as Hypoxia Imaging Agents: Structure-Activity Relationships," J. Biol. Inorg. Chem. 7(3):249-259.
Delettre, C. et al. (Oct. 2000). "Nuclear Gene OPA1, Encoding a Mitochondrial Dynamin-Related Protein, is Mutated in Dominant Optic Atrophy," Nature Genetics 26(2):207-210.
Delettre, C. et al. "OPA1 (Kjer Type) Dominant Optic Atrophy: A Novel Mitochondrial Disease," *Molecular Genetics and Metabolism*, vol. 75, pp. 97-107 (2001).
Diener, H.C. et al. (Jan. 1996). "Lubeluzole in Acute Ischemic Stroke. A Double-Blind, Placebo-Controlled Phase II Trial," Stroke 27(1):76-81.
Dolske et al., "A Preliminary Trial of Ascorbic Acid as Supplemental Therapy for Autism", *Prog. Neum-Psychopharmacol. & DioL Psychtat*. 1993, vol. 17, pp. 765-774.
Donato, S.D. et al. (2001). "The Complex Clinical and Genetic Classification of Inherited Ataxias. II. Autosomal Recessive Ataxias," Neurol. Sci. 22:219-228.
Dowd, P. et al. (Aug. 1995). "On the Mechanism of the Anticlotting Action of Vitamin E Quinone," *Proceedings of the National Academy of Science USA* 92:8171-8175.
Duong, T.Q. (Jul. 2004). "Applications of Diffusion/Perfusion Magnetic Resonance Imaging in Experimental and Clinical Aspects of Stroke," Curr. Atheroscler Rep. 6(4):267-273.
Durckheimer, W. et al. (Oct. 20, 1964). "The Chemistry of 9-Hydroxy-alpha-Tocopherone, A Quinone Hemiacetal", *Journal of the American Chemical Society* 86(20):4388-4393.
Duveau D. Y. et al., "Synthesis and characterization of mitoQ and idebenone analogues as mediators of oxygen consumption in mitochondria", Bioorganic & Medicinal Chemistry, Pergamon, GB, vol. 18, No. 17, Sep. 1, 2010, pp. 6429-6441, XP027218831.
Echtay, K.S. et al. (Nov. 30, 2000). "Coenzyme Q is an Obligatory Cofactor for Uncoupling Protein Function," Nature 408:609-613.
Erhola, M. et al. (Jun. 9, 1997). "Biomaker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.
Fabrizi, G.M. et al. (Apr. 1996). "Autosomal Dominant Limb Girdle Myopathy with Ragged-Red Fibers and Cardiomyopathy: A Pedigree Study by In Vivo 31P-MR Spectroscopy Indicating a Multisystem Mitochondrial Defect," *Jornal of the Neurological Sciences* 137(1):20-27.
Fahey et al., (2004). "The "Prochaska" Microtiter Plate Bioassay for Inducers of NQO1," Chapter 14 in Methods in Enzymology, Quinones

(56) References Cited

OTHER PUBLICATIONS and Quinone Enzymes, Part B, Sies H, ed., Elsevier Academic Press, San Diego, CA, pp. 243-258.
Fieser, L.F. et al. (Sep. 1942). "Alkylation of Para Quinones with Acyl Peroxides," Journal of the American Chemical Society 64(9):2060-2065.
Filipek, P.A. et al. (Dec. 2004). "Relative Carnitine Deficiency in Autism," *Journal of Autism and Developmental Disorders* 34(6):615-623.
Finsterer, "Leigh and Leigh-Like Syndrome in Children and Adults", *Pediatric Neurology*, 2008, vol. 39, No. 4, pp. 223-235.
Flynn, C.J. et al. (1989). "Ischemia and Hypoxia," Chapter 40 in Basic Neurochemistry, 4th Edition, Siegel, G.J. ed. et al., Raven Press, New York, NY, pp. 783-795.
Fryer, M.J. (1998). "Vitamin E Status and Neurodegenerative Disease," Nutritional Neuroscience 1(5):327-351.
Fujibayashi, Y. et al. (Jul. 1997). "Copper-62-ATSM: A New Hypoxia Imaging Agent with High Membrane Permeability and Low Redox Potential," The Journal of Nuclear Medicine 38(7):1155-1160.
Fujishima, T. et al. (1996, e-pub. Sep. 23, 2006). "Synthesis of Vitamin E Analogues: Possible Active Forms of Vitamin E," *Arch. Pharm. Pharma. Med. Chem.* 329(1):27-34.
Fukunaga, K. et al. (1998). "A Simple, Rapid, Highly Sensitive and Reproducible Quantification Method for Plasma Malondialdehyde by High-Performance Liquid Chromatography," *Biomedical Chromatography* 12:300-303.
Fukuzawa, K. et al. (Jul. 1982). "Antioxidant Activities of Tocopherols on Fe2+-ascorbate-Induced Lipid Peroxidation in Lecithin Liposomes," Lipids 17(7):511-513.
Garn, H. et al. (1994). "An improved MTT assay using the electron-coupling agent menadione," Journal of Immunological Methods 168:253-256.
Gellerich, F.N. et al. (e-pub. Jul. 7, 2008). "Impaired Regulation of Brain Mitochondria by Extramitochondrial Ca2+ in Transgenic Huntington Disease Rats," Journal of Biological Chemistry located at http://www.jbc.org.cgi/doi/10.1074/jbc.M709555200, last visited Feb. 10, 2015, 23 pages.
Gerbitz, K-D. et al. (Feb. 1996); "Mitochondria and Diabetes: Genetic, Biochemical, and Clinical Implications of the Cellular Energy Circuit," Diabetes 45(2):113-136.
Ghate, D. et al. (May 2007). "Pharmacokinetics of Intraocular Drug Delivery by Periocular Injections Using Ocular Fluorophotometry," Investigative Ophthalmology and Visual Science 48(5):2230-2237.
Gille, L. et al. (2001). "Effects of Tocopheryl Quinone on the Heart: Model Experiments with Xanthine Oxidase, Heart Mitochondria, and Isolted Perfused Rat Hearts," *Free Radical Biology and Medicine* 30(8):865-876.
Gille, L. et al. (2004). "Oxidized Vitamin E and Ubiquinone: Competition for Binding Sites of the Mitochondrial Cytochrome Complex?" *Annals of the New York Academy of Sciences* 1031:341-343.
Gille, L. et al. (2004). "Redox-Interaction of a a-Tocopheryl Quinone with Isolated Mitochondrial Cytochrome Complex," *Biochemical Pharmacolgy* 68:373-381.
Gille, L. et al. (2010); "Tocopheryl Quinones and Mitochondria," Mol. Nutr. Food Res. 54:1-15.
Goldberg, M.P. et al. (Nov. 1990). Intracellular Free Calcium Increases in Cultured Cortical Neurons Deprived of Oxygen and Glucose, Stroke 21(11-Supp) III):III-75-III-77.
Goldstein, S. et al. (Jun. 2004). "The Comorbidity of Pervasive Developmental Disorder and Attention Deficit Hyperactivity Disorder: Results of a Retrospective Chart Review," *Journal of Autism and Developmental Disorders* 34(3):329-339.
Gonzalez, (1990). "Serum Concentrations and Cellular Uptake of Vitamin E," Medical Hypotheses 32:107-110.
Goodhue, C.T. et al. (May 1965). "Reactions of Vitamin E with Peroxides. II. Reaction of Benzoyl Peroxide with aTocopherol in Alcohols," *Biochemistry* 4(5):854-858.

Gouw, L.G. et al. (May 1995), "Retinal Degeneration Characterizes a Spinocerebellar Ataxia Mapping to Chromosome 3p," Nature Genetics 10:89-93.
Grau, A. et al. (1998); "Dissimilar Protection of Tocopherol Isomers Against Membrane Hydrolysis by Phospholipase A2," Chemistry and Physics of Lipids 91:109-118.
Green, J. et al. (1966) "Bond Stabilisation in Tocopherols. Part I. The Claisen Rearrangement of Allyl Tocopheryl Ethers," *Journal of the Chemical Society C*, pp. 1422-1427.
Gronlund, M.A. et al. (2010); "Ophthalmological Findings in Children and Young Adults with Genetically Verified Mitochondrial Disease," Br. J. Ophthalmol. 94:121-127.
Grotta, J.C. et al. (1988). "Efficacy and Mechanism of Action of a Calcium Channel Blocker After Global Cerebral Ischemia in Rats," Stroke 19:447-454.
Gu et al. "Synthesis, Oxidation-Reduction Potentials and Biological Activity of 1, 4-Benzoquinone Derivatives," *Youji Huaxue*, 1991, 11(5):481-487.
Gu et al. "Synthesis and Inhibitory Activity of Bromoquinone Derivatives", *Tetrahedron*, 1990, 46 (9), pp. 3199-3210.
Gu, L-Q. et al. (1990). "Effect of Substituents of the Benzoquinone Ring on Electron-Transfer Activities of Ubiquinone Derivatives," *Biochimica et Biophysica Acta* 1015(3):482-492.
Gubskii et al. (2008). "Antioxidant and Membranotropic Effects of Monochromanes and Trimethylphenol Derivatives in Vitro," Ukrains'kii Biokhimichnii Zhurnal 80(6):79-85, Chemical Abstract Only, CAPLUS Abstract No. 2009:267923.
Gupta et al. (Jan. 15, 2008, e-pub. Aug. 27, 2007). "Spinocerebellar Ataxia Type 7 Mimicking Kearns-Sayre Syndrome: A Clinical Diagnosis is Desirable," Journal of Neurological Sciences 264:173-176.
Haas et al. (May 2008); "The In-Depth Evaluation of Suspected Mitochondrial Disease: The Mitochondrial Medicine Society's Committee on Diagnosis," Mol. Genet. Metab. 94(1):1637, 32 pages.
Hagio, K. et al. (Apr. 1974). "Synthesis and Reactions of 4-Dimethylsulfuranylidene-2,3,-Dioxotetrahydrofuran Derivatives," *Bulletin of the Chemical Society of Japan* 47(4):909-916.
Han, J. (2006); "Advances in Characterization of Pharmaceutical Hydrates," Trends in Bio/Pharmaceutical Industry 3:25-29.
Hattori, J. et al. (2006). "Are Pervasive Developmental Disorders and Attention Deficit/Hyperactivity Disorder Distinct Disorders?" *Brain & Development* 28:371-374.
Hauptmann, S. et al. (2009, e-pub. Mar. 4, 2008). "Mitochondrial Dysfunction: An Early Event in Alzheimer Pathology Accumulates With Age in AD Transgenic Mice," Neurobiology of Aging 30:1574-1586.
Hawkins, R.D. et al. (1993). "Learning to Modulate Transmitter Release: Themes and Variations in Synaptic Plasticity," Annual Review of Neuroscience 16:625-665.
Hendlin, D. et al. (Apr. 1960) "The Activity of Coenzyme Qlo and Its Analogues in the Succinoxidase System of Electron Transport Particles," Journal of Biological Chemistry, 235(4):1187-1191.
Hodgkiss et al. (May 1989). "The Effect of α-tocopherol and α-tocopheryl quinone on the Radiosensitivity of Thiol-Depleted Mammalian Cells," International Journal of Radiation Oncology, Biology, Physics 16(5), pp. 1297-1300.
Honda, M. et al. (Jun. 2000). "Correlation of Urinary 8-Hydroxy-2'-Deoxyguanosine (8-OHdG), a Biomaker of Oxidative DNA Damage, and Clinical Features of Hematological Disorders: A Pilot Study," *Leukemia Research* 24(6):461-468.
Huang, C.-C. et al. (Mar. 2002); "Rapid Visual Recovery After Coenzyme Q10 Treatment of Leber Hereditary Optic Neuropathy," The Journal of Neuro-Opthalmology22(1):66-67.
Hubscher, J.V. et al. (1990). "Total Synthesis of Naturally Occurring alpha-Tocopherol. Asymmetric Alkylation and Asymmetric Epoxidation as Means to Introduce (R)-Configuration at C(2) of the Chroman Moiety," *Helvetica Chimica Acta* 73(4-6):1068-1086 (English Translation of Abstracts Only).
Hudson, G. et al. (Jul. 2008); "Leber Hereditary Optic Neuropathy," Expert Opinion on Medical Diagnostics 2(7):789-799.
Iizuka et al. (2005); "Pathogenesis of Stroke-Like Episodes in MELAS: Analysis of Neurovascular Cellular Mechanisms," Current Neurovascular Research 2(1):29-45.

(56) References Cited

OTHER PUBLICATIONS

Ikawa, M. et al. (2009, e-pub. Jan. 30, 2009). "PET Imaging of Redox and Energy States in Stroke-Like Episodes of MELAS," Mitochondrion 9:144-148.

Infante, J.P. (1999). "A Function for the Vitamin E Metabolite alpha-Tocopherol Quinone as an Essential Enzyme Cofactor for the Mitochondrial Fatty Acid Desatures," *The FEBS Letters* 446:1-5.

Inoue, S. et al. (1987). "Improved General Method of Ortho Alkylation of Phenols Using Alkyl Isopropyl Sulfide, Sulfryl Chloride, and Triethylamine. An Expedient Synthesis of Representative Oxygen Heterocycles and (2R,4'R, 8'R)-alpha-Tocopherol," *Journal of Organic Chemistry* 52:5495-5497.

Ishizaki et al., "Usefulness of melatonin for developmental sleep and emotional/behavior disorders—studies of melatonin trial on 50 patients", *No To Hattatsu*, Sep. 1999, vol. 31, No. 5, pp. 428-437, with English abstract.

Ito, H. et al. (2008). "Serial Brain Imaging Analysis of Stroke-Like Episodes in MELAS," Brain & Development 30:483-488.

Jaiswal, A.K. (2000). "Characterization and Partial Purification of Microsomal NAD(P)H:Quinone Oxidoreductases," Archives of Biochemistry and Biophysics 375(1):62-68.

James, A.M. et al. (Jun. 3, 2005). "Interactions of Mitochondria-Targeted and Untargeted Ubiquinones with the Mitochondrial Respiratory Chain and Reactive Oxygen Species," *The Journal of Biological Chemistry* 280(22):21295-21312.

Jarrett, S.G. et al. (2008). "Mitochondrial DNA Damage and Its Potential Role in Retinal Degeneration," Progress in Retinal and Eye Research 27:596-607.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (Oct. 23, e-pub. Aug. 15, 2003). "Mitochondria-Targeted Antioxidents Protect Friedrich Ataxia Fibroblasts from Endogenous Oxidative Stress more Effectively than Untargeted Antioxidants," *The FASEB Jornal* 17(13):1972-1974.

Jiang, Q. et al. (Oct. 10, 2000). κ-Tocopherol and its Major Metabolite, in Contrast to α-Tocopherol, Inhibit Cyclooxygenase Activity in Macrophages and Epithelial Cells, Proceedings of the National Academy of Sciences 97(21):11494-11499.

Jones, J.W. et al. (1977). "10% Soybean Oil Emulsion As a Myocardial Energy Substrate After Ischemic Arrest," Surgical Forum 28:284-285.

Jung, M E et al: "First Enantioselective Total Synthesis of the Endogenous Natriuretic Agent LLU-Alpha", Tetrahedron Letters, Elsevier, Amsterdam, NL, vol. 40, No. 25, Aug. 27, 1999 (Aug. 27, 1999), pp. 6339-6342, XP004173857, ISSN: 0040-4039, DOI: 10.1016/S00404039(99)01204-6.

Jung, M.Y. et al. (Sep. 1, 1990). "Effects of α-, γ-, and σ-Tocopherols on Oxidative Stability of Soybean Oil," Journal of Food Science 55(5), pp. 1464-1465.

Kabbe, H.J. et al. (1978). "Eine Neue Synthese von 3,4-Dehydro-alpha-Tocotrienol and Vitamin-E," *Synthesis* 888-889. (Translation of Abstract only: Chemical Abstract CAPLUS Abstract No. 1979:168774, two pages).

Kamat, J.P. et al. (1995). "Tocotrienols from Palm Oil as Potent Inhibitors of Lipid Preoxidation and Protein Oxidation in Rat Brain Mitochondria," Neurosci. Lett. 195, pp. 179-182.

Kanno, T. et al. (1996). "Inhibition of Neutrophil-Superoxide Generation by α-Tocopherol and Coenzyme Q," Free Radical Research 24(4), pp. 281-289.

Kapinya K. et al. (2003). "Role of NAD(P)H:quinone oxidoresuctase in the progression of neuronal cell death in vitro and following cerebral ischaemia in vivo," Journal of Neurochemistry 84, pp. 1028-1039.

Kariya, S. et al. (2005, e-pub. Mar. 10, 2005). "Humanin Detected in Skeletal Muscles of MELAS Patients: A Possible New Therapeutic Agent," Acta Neuropathol. 109, pp. 367-372.

Karry, R. et al. (2004). "Mitochondria49 Complex I Subunits Expression Is Altered in Schizophrenia: A Postmortem Study," Biological Psychiatry 55(7), pp. 676-684.

Kaufman, P. et al. (Apr. 27, 2004). "Cerebral Lactic Acidosis Correlates with Neurological Impairment in MELAS," Neurology 62(8):1297-1302.

Keeney et al. (May 10, 2006). "Parkinson's Disease Brain Mitochondrial Complex I Has Oxidatively Damaged Subunits and Is Functionally Impaired and Misassembled," The Journal of Neuroscience 26(19), pp. 5256-5264.

Kelso, G.F. et al. (Feb. 16, 2001). "Selective Targeting of a Redox-active Ubiquinone to Mitochondria within Cells", The Journal of Biological Chmistry, vol. 276, No. 7, pp. 4588-4596.

Khan, S.Z. (2006). "Mitochondrial Complex-1 in Parkinson's Disease," Neurology India located at http://www.neurologyindia.com/article.asp?issn=0028-3886;year=2006;volume=54;is . . . , last visited Feb. 10, 2015.

Khanna, S. et al. (2005, e-published Sep. 15, 2005). "Neuroprotective Properties of the Natural Vitamin E α-Tocotrienol," Stroke 36:e144-e152.

Kim, J.Y. et al. (May 2004). "Urinary 8-Hydroxy-2'-Deoxyguanosine as a Biomaker of Oxidative DNA Damage in Workers Exposed to Fine Particulates," Environmental Health Perspectives 112(6):666-671.

Kim, S-O. et al. (Mar. 8, 2004). "KR-31378 Protects Neurons from Ischemia-Reperfusion Brain Injury by Attenuating Lipid Peroxidation and Glutathione Loss," European Journal of Pharmacology 487(1-3):81-91.

Kinouchi, H. et al. (Dec. 1991). "Attenuation of Focal Cerebral Ischemic Injury in Transgenic Mice Overexpressing CuZn Superoxide Dismutase," Proc. Natl. Acad. Sci. USA 88, pp. 11158-11162.

Kirkman, M.A. (Jul. 2009). "Quality of Life in Patients with Leber Hereditary Optic Neuropathy," Investigative Ophthalmology & Visual Science 50(7), pp. 3112-3115.

Kleijnen et al., "Niacin and Vitamin B6 in Mental Functioning: A Review of Controlled Trials in Humans", *Biol. Psychiatry*, 1991, vol. 29, pp. 931-941.

Klivenyi et al. "Alpha-Tocopherol/lipd ratio in blood is decreased in patients with Leber's hereditary optic neuropathy and asymptomatic carriers of the 11778 mtDNA mutation"; J. Neurol Neurosurg Psychiatry Mar. 2001;70(3), pp. 359-362.

Kobayashi, M.S. et al. (2000). "Antioxidants and Herbal Extracts Protech HT-4 Neuronal Cells Against Glutamate-Induced Cytotoxicity," Free Radical Research 32(2), pp. 115-124.

Korizis, K.N. et al. (2001). "Determination of Malondialdehyde by Capillary Electrophoresis, Application to Human Plasma and Relation of its Levels with Prematurity," *Biomedical Chromatography* 15:287-291.

Kosmorsky, G. et al. (Feb. 1991). "Neuro-Ophthalmologic Manifestations of Mitochondrial DNA Disorders: Chronic Progressive External Ophthalmoplegia, Kearns-Sayre Syndrome, and Leber's Hereditary Optic Neuropathy," Neurologic Clinics 9(1), pp. 147-161.

Kovalenko, V.N. et al. (1979); "Vitamin E Activity of Vitamin E Derivatives in Experimental Encephalomalacia in Chicks," Ukrainskii Biokhimicheskii Zhumal 51(6):665-668, Chemical Abstract Only, CAPLUS Abstract No. 1980:74772, 1 page.

Krajcovicova-Kudlackova, M. et al. (2009). "Plasma Concentrations of Selected Antioxidants in Autistic Children and Adolescents," *Bratisl lek listy* 110(4)247-250.

Kumadaki, I. et al. (1989). "Trifluoromethylation of Tocopherols," *Synthetic Communications* 19(1&2):173-177.

Kunitsa et al. (Nov. 1993); "Effects of Tocopherol and its Analogs on in vivo Lipid Peroxidation and Electron Transport in Rat Liver Mitochondria," Biochemistry (Moscow) An International Journal 58(11), pp. 1256-1259.

Kunz, W.S. et al. (2004); "The Role of Mitochondria in Epilepsy: Implications for Neurodegenerative Diseases," Toxicology Mechanisms and Methods 14, pp. 19-23.

Kunz, W.S. et al. (Nov. 2000); "Mitochondrial Complex I Deficiency in the Epileptic Focus of Patients with Temporal Lobe Epilepsy," Annals of Neurology 48(5), pp. 766-773.

(56) References Cited

OTHER PUBLICATIONS

Kwong, J.Q. et al. (2006). "The Role of Mitochondria in Inherited Neurodegenerative Diseases," Journal of Neurochemistry 97, pp. 1659-1675.
Lamson, D.W. (2002); "Mitochondrial Factors in the Pathogenesis of Diabetes: A Hypothesis for Treatment—Mitochondial Factors/ Diabetes," Alternative Medicine Review 7(2):94-111.
Larisch, B. et al. (Jul. 1996). "Reactions of Dehydroascorbic Acid with Primary Aliphatic Amines Including NaAcetyllysine," *Journal of Agricultural and Food Chemistry* 44(7):1630-1634.
Laszlo, A. et al. (1994). "Serum Serotonin, Lactate and Pyruvate Levels in Infantile Autistic Children", *Chnica Chimica Acta* 229:205-207.
Lee, P.I. (1992). "Diffusion-Controlled Matrix Systems," Chapter 3 in Treatise on Controlled Dug Delivery, *Kydonieus, A. ed., Marcel Dekker, Inc.*, New York, NY, pp. 155-197.
Lenaz, G. et al. (2000). "Mitochondrial Bioenergetics in Aging," *Biochimica et Biophysica Acta* 1459:397-404.
Li, H. et al., "CoQ10 fails to protect brain against focal and global ischemia in rats." Brain Res. Sep. 15, 2000; 877(1), pp. 7-11.
Liepkalns et al. "Regulation of Cell Division in a Human Glioma Cell Clone by Arachidonic Acid and a-Tocopherolquinone," *Cancer Letters*, 15 (1982) 173-178.
Lipshutz, B.H. et al. (Feb. 12, 1998). "An Expeditious Route to CoQn, Vitamins $K_1$ and $K_2$, and Related Allytated para-Quinones Utilizing Ni(0) Catalysis," *Tetrahedron* 54(7):1241-1253.
Liu et al. "Design, Synthesis, and Structure-Activity Relationship of Podocarpic acid Amides as Liver X Receptor Agonists for Potential Treatment of Atherosclerosis," *Bioorganic & Medicinal Chemistry Letters* 15 (2005), pp. 4574-4578.
Lodi, R. et al. (2001). "Antioxidant Treatment Improves In Vivo Cardiac and Skeletal Muscle Bioenergetics in Patients with Friedreich's Ataxia," Annals of Neurology 49, pp. 590-596.
Lord C. et al. "Autism spectrum disorder", *Neuron* 2000 28 (2): 355-63.
Lowell, B. (Jan. 21, 2005). "Mitochondrial Dysfunction and Type 2 Diabetes," Science 307(5708), pp. 384-387.
Lustbader, J.W. et al. (Apr. 16, 2004). "ABAD Directly Links A( to Mitochondrial Toxicity in Alzheimer's Disease," Science 304(5669):448-452.
Lynch, D.R. et al. (Jul. 2012; e-pub. Jun. 28, 2012). "A0001 in Friedreich Ataxia: Biochemical Characterization and Effects in a Clinical Trial," Mov. Disord. 27(8):1026-1033.
Lynch, D.R. et al. (May 2002). "Near Infrared Muscle Spectroscopy in Patients with Friedreich's Ataxia," *Muscle & Nerve* 25(5):664-673.
MacKenzie, J.B. et al. (1950). "The Biological Activity of alpha-Tocopherylhydroquinone and alpha-Tocopherylquinone," *Journal of Biological Chemistry* 183(2):655-662.
MacManus, J.P. et al. (1993). "Global Ischemia Can Cause DNA Fragmentation Indicative of Apoptosis in Rat Brain," Neuroscience Letters 164:89-92.
Makovetskii, V.P. et al. (1987). "Synthesis, Properties, and Detoxication Activity of a-tocopherol Analogs and Derivatives," Khimiko-Farmatsevticheskii Zhumal21(12):1441-1446, Chemical Abstract Only, CAPLUS Abstract No. 1988:142850, 2 pages.
Maloney, D.J. et al. (2005, e-pub. Aug. 20, 2005). "A Stereocontrolled Synthesis of delta-trans-Tocotrienoloic Acid,", *Acid Letters* 7(19):4297-4300.
Man, P.Y.W. et al. (2002). "Leber Hereditary Optic Neuropathy," J. Med. Genet. 39, pp. 162-169.
Mann, V.M. et al. (1992). "Brain, Skeletal Muscle and Platelet Homogenate Mitochondrial Function in Parkinson's Disease," *Brain* 115:333-342.
Marpat Accession No. 138:187513, 2 pages.
Matthews, P.M. et al. (Apr. 1991). "In Vivo Magnetics Resonance Spectroscopy on Brain and Muscle in a Type of Mitochondrial Encephalomyopathy (MERRF)," *Annals of Neurology* 29(4):435-438.

Mayer, H. et al. (1967). "Uber die Chemie des Vitamins E. 8. Mitteilung [1]. Die Stereochemie von Naturlichem y-Tocotrienol (Plastochromanol-3), Plastochromanol-8 and Plastochromanol-8)," *Helvetica Chimica Acta* 50(5):1376-1393, No. 139. (English Summary on pp. 1392-1393 and Chemical Abstract CAPLUS Abstract No. 1967:473698 is also included.).
Mazzini, F. et al. (2005, e-pub. Nov. 30, 2004). "Easy Route to Labeled and Unlabeled R, R, R-к-Tocopherol by Aryl Demethylation of a-Homologues," *Tetrahedron* 61:813-817.
McGinnis, "Oxidative Stress in Autism", *Integrative Medicine*, vol. 3, No. 6, Dec. 2004/Jan. 2005, pp. 42-57.
Medline Plus, Adrenoleukodystrophy, U.S. National Library of Medicine, Nov. 1, 2016, printed from https://medlineplus.gov/ency/article/001182.htm, 4 pages.
Merck Manuals, Retinitis Pigmentosa, 2005, http://www.merck.com/mmpe/print/sec09/ch106/ch106h.html, printed May 27, 2008, 2 pages.
Milone, M. et al. "Mitochondrial disorder with OPA1 mutation lacking optic atrophy," Mitochondrion, vol. 9, pp. 279-281 (2009).
Mishima, Tanaka T. et al. (2003) "Vitamin E isoforms alpha-tocotrienol and gamma-tocopherol prevent cerebral infarction in mice" Neurosci Lett; 337 (1) 56-60 DOI: http://www.ncbi.nlm.nih.gov/pubmed/12524170.
Molinari, G.F. (1986). "Experimental Models of Ischemic Stroke," Chapter 5 in Stroke, Pathophysiology, Diagnosis, and Management, vol. 1, Barnett, H.J.M. ed. et al., Churchill Livingstone Inc., pp. 57-73.
Monte, W. T. et al. (May/Jun. 2001). "An Efficient Process for the Synthesis of y-Arylbutanals via Copper-Mediated Grignard Coupling," *Organic Process Research & Development* 5(3):267-269.
Moore, A.N.J. et al. (1997). "α-Tocopheryl Quinone is Converted into Vitamin E in Man," Free Radical Biology & Medicine 22(5):931-934.
Moss, Leber's Congenital Amaurosis, http://www.tsbvi.edu/Outreach/seehear/spring01/lebers.htm, printed Apr. 27, 2008, 3 pages.
Mukai et al, "Stopped-flow kinetic study of vitamin E regeneration reaction with biological hydroquinones (reduced forms of ubiquinone, vitamin K, and tocopherolquinone) in solution", J Biol Chem, Nov. 5, 1992, vol. 267, No. 31, pp. 22277-22281.
Mukai, K. et al. (1989). "Synthesis and Kinetic Study of Antioxidant Activity of New Tocopherol (Vitamin E) Compounds," *The Journal of Organic Chemistry*, 54(3):552-556.
Mukai, K. et al. (1989). "Synthesis and Stopped-Flow Investigation of Antioxidant Activity of Tocopherols. Finding of New Tocopherol Derivatives Having the Highest Antioxidant Activity Among Phenolic Antioxidants," *The Journal of Organic Chemistry* 54(3):557-560.
Mukai, K. et al. (1991). "Structure-Activity Relationship in the Quenching Reaction of Singlet Oxygen by Tocopherol (Vitamin E) Derivatives and Related Phenols. Finding of Linear Correlation Between the Rates of Quenching of Singlet Oxygen and Scavenging of Peroxyl and Phenoxyl Radicals in Solution," *The Journal of Organic Chemistry* 56(13):4188-4192.
Munnich, A. et al. (1992). "Clinical Aspects of Mitochondrial Disorders," *Journal of Inherited Metabolic Disease* 15(4):448-455.
Myagkov, V. "Monomolecular Films of Octadecyl-Substituted Quinone and Hydroquinone and their Charge Transfer Complexes," *Colloid Journal of the USSR, Russian Original*, 1985, vol. 47, No. 5, pp. 833-836.
Myers, S.M. et al. (Nov. 2007, e-pub. Oct. 29, 2007). "Management of Children with Autism Spectrum Disorders," *Pediatrics* 120(5):1162-1182.
Neuzil, J. et al. (Oct. 1998). "α-Tocopherol in Atherogenesis: Do We Know Its Real Role?" Cardiovascular Drugs and Therapy 12(5):421-423.
Newman et al., Nerve fibre layer loss in diseases of the outer retinal layer, Br J Ophthalmol. Jan. 1987;71(1):21-6, printed from https://www.ncbi.nlm.nih.gov/pubmed/3814566, 1 page, abstract only.
Niaudet et al. (1996). "Renal Involvement in Mitochondrial Cytopathies," Pediatric Nephrol. 10(3):368-373.
Nishigaki, Y. et al. (2003). "A Novel Mitochondrial tRNALeu(UUR) Mutation in a Patient with Features of MERRF and Kearns-Sayre Syndrome," *Neuromuscular Disorders* 13:334-340.

(56) References Cited

OTHER PUBLICATIONS

Noens, I. et al. (Sep. 2006). "The ComFor: an Instrument for the Indication of Augmentative Communication in People with Autism and Intellectual Disability," *Journal of Intellectual Disability Research* 50(Part 9):621-632.

Obata, A. et al. (2001). "Retention Mechanism of Hypoxia Selective Nuclear Imaging/Radiotherapeutic Agent Cu-diacetyl-bis(N4-Methylthiosemicarbazone) (Cu-ATSM) in Tumor Cells," Annals of Nuclear Medicine 15(6):499-504.

Obón J. et al. (1999). "Enzymatic cycling assay for D-carnitine determination," Anal Biochem. 274(1):34-9.

Ogawa et al. (Jul. 2008). "γ-Tocopheryl quinone, not alpha-tocopheryl quinone, induces adaptive response through up-regulation of cellular glutathione and cysteine availability via activation of ATF4", Free Radical Research, 42(7), pp. 674-687.

Olichon, A. et al. (2006, e-pub. Apr. 20, 2006). "Mitochondrial Dynamics and Disease, OPA1," Biochimica et Biophysica Acta 1763:500-509.

Oliveira, G. et al. (2005). "Mitochondrial Dysfunction in Autism Spectrum Disorders: a Population-Based Study," *Developmental Medicine & Child Neurology* 47:185-189.

Oliveira ,J.M.A. et al. (2007). "Mitochondrial Dysfunction in Huntington's Disease: The Bioenergetics of Isolated and in situ Mitochondria from Transgenic Mice," Journal of Neurochemistry 101(1):241-249.

Omura, K. (Apr. 14, 1989). "Iodine Oxidation of alpha-Tocopherol and Its Model Compound in Alkaline Methanol: Unexpected Isomerization of the Product Quinone Monoketals," *The Journal of Organic Chemistry* 54(8):1987-1990.

Orbis, (2003). "Chronic Progressive External Opthalmoplegia," located at http://telemedicine.orbis.orgibins/volume_page.asp?cid=1-2896-5258-5381&print=true, last visited on Jun. 10, 2014, 1 page.

Oswald, D.P. et al. (2007). "Medication Use Among Children with Autism-Spectrum Disorders", *Journal of Child Adolescent Psychopharmacology* 17(3):348-355.

Packer, L. et al. (2001). "Symposium: Molecular Mechanisms of Protective Effects of Vitamin E in Atherosclerosis, Molecular Aspects of a-Tocotrienol Antioxidant Action and Cell Signalling," The Journal of Nutrition 131:369S-373S.

Pagliacci, M.C. et al. (1993). "Genistein Inhibits Tumor Cell Growth in vitro but Enhances Mitochondrial Reduction of Tetrazolium Salts: A Further Pitfall in the Use of the MTT Assay for Evaluating Cell Growth and Survival," Eur J. Cancer 29A(11): 1573-1577.

Paranich, A.V. et al. (1991). "Age-Related Tocopherol Content of Normal and Ischemic Heart and Liver of Rats," Fiziologicheskii Zhurnal (Kiev, 1978-1993) 37(5):16-19. (English Abstract only).

Park, L.C.H. et al. (2000). "Metabolic Impairment Elicits Brain Cell Type-Selective Changes in Oxidative Stress and Cell Death in Culture," Journal of Neurochemistry 74(1):114-124.

Patani et al, "Bioisosterism: A Rational Approach in Drug Design," Chemical Reviews, Dec. 1996, vol. 19, No. 8, pp. 3147-3176.

Pearce, B.C. et al. (1992). "Hypocholesterolemic Activity of Synthetic and Natural Tocotrienols," *Journal of Medicinal Chemistry* 35(20):3595-3606.

Pearce, B.C. et al. (1994). "Inhibitors of Cholesterol Biosynthesis. 2. Hypocholesterolemic and Antioxidant Activities of Benzopyran and Tetrahydronaphthalene Analogues of the Tocotrienols," *Journal of Medicinal Chemistry* 37(4):526-541.

Pelak, V.S. et al. (Sep. 2004). "Neuro-Ophthalmic Manifestations of Neurodegenerative Disease," Ophthalmology Clinics of North America 17(3):311-320.

Pelter, A. et al. (1993). "Phenolic Oxidations with Phenyliodonium Diacetate," *Journal of the Chemical Society, Perkins Transactions* 1 16:1891-1896.

Pelter, A. et al. (1997). "The Synthesis of 8a-Methoxy-2H, 6H-Chromen-6-ones and Corresponding 2H-Chromenes by a Unique Process Utilising Phenolic Oxidation," *Tetrahedron* (53(11):3879-3916.

Pileni MP, et al. (Apr. 15, 1980). "Zinc-Porphyrin Sensitized Reduction of Simple and Functional Quinones in Vesicle Systems," *Chemical Physics Letters*, vol. 71, No. 2, pp. 317-321.

Pileni, M.P. et al. (1980). "Zinc Porphyrin Sensitized Reduction of Simple and Functional Quinones in Micellar Systems," *Journal of Physical Chemistry* 84(14):1822-1825.

Pilger, A. et al. (Sep. 2001). "Longitudinal Study of Urinary 8-Hydroxy-2'-Deoxyguanosine Excretion in Healthy Adults," *Free Radical Research* 35(3):273-280.

Pilz, J. et al. (2000). "Measurement of Free and Bound Malondialdehyde in Plasma by High Performance Liquid Chromatography as the 2,4-Dinitrophenylhydrazine Derivative," *Journal of Chromatography B* 742:315-325.

Pina, I.L. et al. (Mar. 4, 2003). "Exercise and Heart Failure: A Statement From the American Heart ASsociation Committee on Exercise, Rehabilitation, and Prevention," *Circulation* 107(8):1210-1225.

Prochaska H.J. et al. (1988). "Direct measurement of NAD(P)H:quinone reductase from cells cultured in microtiter wells: a screening assay for anticarcinogenic enzyme inducers," Anal. Biochem. 169, pp. 328-336.

Pulsinelli, W.A. (2000). "Ischemic Cerebrovascular Disease," Chapter 470 and "Hemorrhagic Cerebrovascular Disease," Chapter 471 in Cecil Textbook of Medicine, 21st Edition, Goldman, L. ed. et al., W.B. Saunders Company: Philadelphia, PA, pp. 2099-2115.

Qureshi, A.A. et al. (2001). "Novel Tocotrienols of Rice Bran Inhibit Atherosclerotic Lesions in C57BL/6 ApoE-Deficient Mice," Journal of Nutrition 131:2606-2618.

Raghava et al. (2004) "Periocular Routes for Retinal Drug Delivery," Expert Opin. Drug Deliv. 1(1):99-114.

Ricciarelli, R. et al. (1998). "α-Tocopherol Specifically Inactivates Cellular Protein Kinase C α by Changing Its Phosphorylation State," Biochem. J. 334, pp. 243-249.

Richards, R.M.E. (2004). "Ophthalmic Products," Chapter 26 in Pharmaceutical Practice, Third Edition, Winfield, A.J. et al. eds., Churchill Livingstone, pp. 264-279.

Rimland, et al., The Effect of High Doses of Vitamin B6 on Autistic Children: A Double-Blind Crossover Study, IIAm. J. Psychiatry, Apr. 1978, vol. 135, No. 4, pp. 472-475.

Riss T. et al (2013). "Cell viability Assays," Assays Guidance Manual, 28 pages.

Rogers, S.J. et al.(Jan. 2008). "Evidence-Based Comprehensive Treatments for Early Autism," *J. Clin. Child. Adolesc. Psychol.* 37(1):8-38, thirty-eight pages.

Rolfe, P. (2000). "In Vivo Near-Infrared Spectroscopy," *Annual Review of Biomedical. Engineering* 2:715-754.

Rossignol, D.A. et al. (2008). "Evidence of Mitochondrial Dysfunction in Autism and Implications for Treatment," *American Journal of Biochemistry and Biotechnology* 4(2):208-217.

Russo, R. et al. (2008). "Rational Basis for the Development of Coenzyme Q10 as a Neurotherapeutic Agent for Retinal Protection," Progress in Brain Research 173:575-582.

Sadun et al., "Effect of EPI-743 on the Clinical Course of the Mitochondrial Disease Leber Hereditary Optic Neuropathy," Archives of Neurology, Mar. 2012, vol. 69, No. 3, pp. 331-338.

Sakamoto et al. "Role of the Isoprenyl Tail of Ubiquinone in Reaction with Respiratory Enzymes: Studies with Bovine Heart Mitochondrial Complex I and *Escherichia coli* bo-Type Ubiquinol Oxidase", *Biochemistry*, 1998, vol. 37, pp. 15106-15113.

Saldeen, T. et al. (Oct. 1999). "Differential Effects of α- and γ-Tocopherol on Low-Density Lipoprotein Oxidation, Superoxide Activity, Platelet Aggregation and Arterial Thrombogenesis," Journal of the American College of Cardiology 34(4):1208-1215.

Schudel, P. et al. (1963). Uber die Chemie des Vitamins E. 5. Mitteilung. Die Synthese von rac. all-trans-.zeta..sub.1-und-.epsilon.-Tocopherol, *Helvetica Chimica Acta* 46(7):2517-2526, English summary on p. 2526.

Scott, J.W. et al. (1976). "Syntheses of (2R,4'R,8'R)-alpha-Tocopherol and (2 R,3'E,7'E)-alpha-Tocotrienol," *Helvetica Chimica Acta* 59:290-306, Nr. 34.

Sen, C.K. et al. (2007). "Tocotrienols in Health and Disease: The Other Half of the Natural Vitamin E Family," Mol. Aspects Med. 28(5-6):692-728.

Sen, C.K. et al. (Apr. 28, 2000); "Molecular Basis of Vitamin E Action. Tocotrienol Potently Inhibits Glutamate-Induced pp60c-Src

(56) References Cited

OTHER PUBLICATIONS

Kinase Activation and Death of HT4 Neuronal Cells," The Journal of Biological Chemistry 275(17):13049-13055.
Shi, et al. "Hydrophobic Acceleration of Electron Transfer Processes", *Journal of Organic Chemistry*, 1996, vol. 61, pp. 4698-4702.
Shiraishi, M. et al. (Sep. 1989). "Quinones. 4. Novel Eicosanoid Antagonists: Synthesis and Pharmacological Evaluation," *Journal of Medicinal Chemistry* 32(9):2214-2221.
Siegel, D. et al. (1997). "The Reduction of a-Tocopherolquinone by Human NAD(P)H: Quinone Oxidoreductase: The Role of aTocopherolhydroquinone as a Cellular Antioxidant," *Molecular Pharmacology* 53:300-305.
Siesjö, B.K. (1981). "Cell Damage in the Brain: A Speculative Synthesis," Journal of Cerebral Blood Flow and Metabolism 1(2):155-185.
Sigman, M. et al. (2004). "Early Detection of Core Deficits in Autism," *Mental Retardation and Developmental Disabilities Research Reviews*, vol. 10, pp. 221-233.
Silbert et al. (1996); "The "S" in MELAS," Journal of Stroke and Cerebrovascular Diseases 6(2):67-71.
Silbert, L.S. et al. (Jun. 2, 1959). "Peroxides. VI. Preparation of t-Butyl Peresters and Diacyl Peroxides of Aliphatic Monobasic Acids," *Journal of the American Chemical Society* 81(10): 2364-2367.
Singh S. B. et al. "Discovery and development of dimeric podocarpic acid leads as potent agonists of liver X receptor with HDL cholesterol raising activbity in mice and hamsters," *Bioorganic & Medicinal Chemistry Letters* 15 (2005), 2824-2828.
Soll, et al. (Aug. 1-6, 1983). Inhibitor Binding and Displacement in Plastoquinone Depleted Chloroplasts, *Advances in Photosynthesis Research, Proceedings of the International Congress of Photsynthesis*, Brussels, Belgium IV.1:5-8.
Spoyalov, Andrei P. et al. "Endor and Eseem studies of Ion Radicals of Artificial Dimethoxy-or Halogen-1,4—benzoquionones with an Alkyl Side Chain of Differing Length," *J. Chem. Soc. Perkins Trans.*, 1992, pp. 1519-1524.
Staniek, K. et al. (Nov. 1, 2005). "The Protection of Bioenergetic Functions in Mitochondria by New Synthetic Chromanols," *Biochemical Pharmacology* 70(9):1361-1370.
Steghens, J.-P. et al. (2001). "Diaminonaphtalene, a New Highly Specific Reagent for HPLC-UV Measurement of Total and Free Malondialdehyde in Human Plasma or Serum," *Free Radical Biology & Medicine* 31(2):242-249.
Stella, V.J. et al. (2007). "Prodrugs: Challenges and Rewards, Part I," Biotechnology: Pharmaceutical Aspects 1(1):24.
STN Accession No. 1985:621368, last visited Jan. 23, 2007, 1 page.
STN Accession No. 1992:58878, last visited Jan. 23, 2007, 1 page.
STN Accession No. 1993;21870, last visited Jan. 23, 2007, 2 pags.
Strangman, G. et al. (Oct. 1, 2002). "Non-Invasive Neuroimaging Using Near-infrared Light," *Biological Psychiatry* 52(7):679-693.
Strohschein, S. et al., (Jan. 1, 1998). "Shape Selectivity of C30 Phases for RP-HPLC Separation of Tocopherol Isomers and Correlation with MAS NMR Data from Suspended Stationary Phases," Analytical Chemistry 70(1):13-18.
Sue et al. "Mitochondria Respiratory Chain Diseases and Mutations in Nuclear DNA: A promising Start?" *Brain Pathalogy*, 2000, vol. 10, pp. 442-450.
Tabrizi, S.J. et al. (Jul. 1998). "Primary and Secondary Deficiencies of the Mitochondrial Respiratory Chain," The Neurologist 4(4):169-179.
Taivassalo, T. et al. (Feb. 2003). "The Spectrum of Exercise Tolerance in Mitochondrial Myopathies: A Study of 40 Patients," *Brain* 126(Pt2), pp. 413-423.
Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Annals of Neurology*, 51(1):38-44.

Tanito, M. et al. (May 2004). "Distribution of Tocopherols and Tocotrienols to Rat Ocular Tissues After Topical Ophthalmic Administration," Lipids 39(5):469-474.
Testai, F.D. et al. (2010). "Inherited Metabolic Disorders and Stroke Part 1," Arch. Neurol. 67(1):19-24.
Theriault, A. et al. (Jul. 1999). "Tocotrienol: A Review of Its Therapeutic Potential," Clinical Biochemistry 32(5):309-319.
Thom S.M. et al. (1993). "Factors affecting the selection and use of tetrazolium salts as cytochemical indicators of microbial viability and activity," J. Appl. Bacteriol 74(4):433-43.
Thomas, A.D. et al. (Aug. 8, 1986). "Repetitive Diels-Alder Reactions for the Growth of Linear Polyacenequinoid Derivatives," *Journal of Organic Chemistry* 51(22):4160-4169.
Tietjen, G.E. (1996). "Stroke in MELAS," Journal of Stroke and Cerebrovascular Diseases 6(2):59-60.
Timochko, M.F. et al. (1998). "Metabolic Aspects of Oxygen Homeostasis Formation Under Extreme Conditions," with English translation of paragraph 5 on p. 7, L'vov, located at <http://posrednik.ru/tren/tim_sv.htm>, last visited on Sep. 29, 2008, 52 pages.
Tiranti et al. "Mutations of SURF-1 in Leigh Disease Associated with Cytochrome c Oxidase Deficiency," Am J. Hum. Genet., 1998, vol. 63, pp. 1609-1621.
Trumpower, B.L. (Jul. 15, 1990). "The Protonmotive Q Cycle. Energy Transduction by Coupling of Proton Translocation to Electron Transfer by Cytochrome $bc_1$ Complex," *The Journal of Biological Chemistry* 265(20):11409-11412.
Tsuchiya, K. et al. (1999). "MELAS with Prominent White Matter Gliosis and Atrophy of the Cerebellar Granular Layer: A Clinical, Genetic, and Pathological Study," Acta Neuropathol. 97:520-524.
Ueda, K. et al. (Feb. 1997). "Evaluation of Changes in Hepatic Energy Metabolism during Exercise by Ketone Body Ration in Humans," *Journal of Cardiology* 29(2):95-102; English abstract.
Urano, et al. (1983). "Synthesis of dl-a-Tocopherol and dl-a-Tocotrienol," Chem. Pharm. Bull. 31(12):4341-4345.
Van Beekvelt, M.C.P. et al. (Oct. 1999). "Quantivative Near-Infared Spectroscopy Discriminates Between Mitochondrial Myopathies and Normal Muscle," *Annals of Neurology* 46(4):667-670.
Van Haaften, R.I.M. et al. (Mar. 15, 2001). "No Reduction of a-Tocopherol Quinone by Glutathione in Rat Liver Microsomes," Biochemical Pharmacology 61(6):715-719.
Vatassery, G. et al. (Apr. 5, 2004). "Iron Uncouples Oxidative Phosphorylation in Brain Mitochondria Isolated From Vitamin E-Deficient Rats," *Biochimica et Biophysica Acta* 1688(3):265-273.
Vippagunta, S.R. et al. (2001). "Crystalline Solids," Advanced Drug Delivery Reviews 48:3--26.
Volkmar, F. et al. (2005, e-pub. Sep. 14, 2004). "Autism in Infancy and Early Childhood," *Annu. Rev. Psychol.* 56:315-336.
Wakakura, M. et al. (2009). "Initial Temporal Field Defect in Leber Hereditary Optic Neuropathy," Jpn. J. Ophthalmol. 53:603-607.
Walter, et al. "Three Classes of Ubiquinone Analogs Regulate the Mitochondrial Permeability Transition Pore through a Common Site," *The Journal of Biological Chemistry*, 2000, vol. 275, No. 38, pp. 29521-29527.
Wang, J.-F. (Dec. 2007). "Defects of Mitochondrial Electron Transport Chain in Bipolar Disorder: Implications for Mood-Stabilizing Treatment," The Canadian Journal of Psychiatry 52(12):753-762.
Warner, S.A. et al. (May 1, 1983). "Synthesis and Metabolism of a-Tocopherol Quinone in Normal and Diabetic Mouse Liver," Federation Proceedings, American Society of Biological Chemists, 74th Annual Meeting, San Francisco, CA, Jun. 5-9, 1983, 42(7):1919, Abstract No. 944.
Watson, B.D. et al. (1989). "Ischemic Injury in the Brain. Role of Oxygen Radical-Mediated Processes," Annals. New York Academy of Sciences 559:269-281.
Wechter, W.J. et al. (Jun. 1996). "A New Endogenous Natriuretic Factor: LLU-α," Proc. Natl. Acad. Sci. USA 93:6002-6007.
Weichet et al. "Collection of Czechoslovak Chemical Communications", (1966), vol. 31, No. 12, pp. 4598-609.
Weichet J. et al. "New Substituted Benzohydroquinones", Chemical Abstracts Service, Columbus, Ohio, US; Database CA, XP002698443, retrieved from STN Database accession No. 1968:95542; 1 page.

(56) References Cited

OTHER PUBLICATIONS

Williard, D. et al. Identification of a fatty acid Δ 6-desaturase deficiency in human skin fibroblasts, *The Journal of Lipid Research*, 2001, vol. 42, pp. 501-508.

Witting P K et al.: "A Rapid and Simple Screeing Test for Potential Inhibitors of Tocopherol-Mediated Peroxidation of LDL Lipids", Journal of Lipid Research, *American Society for Biochemistry and Molecular Biology, Inc, US*, vol. 27, No. 4, Jan. 1, 1996, pp. 853-867, XP001095707, ISSN: 0022-2275.

Woodward et al., The inflow and outflow of anti-glaucoma drugs, May 2004, *rends in Pharmacological Sciences*, vol. 25, issue 5, 238-241.

Wray, S. et al. "Adrenoleukodystrophy with disease of the eye and optic nerve," Am. J. Ophthalmol. 1976, vol. 82, No. 3, pp. 480-485, Abstract only, 1 page.

Wrobel, S. (Apr. 7, 2008). "Mitochondria Play Role in Pathogenesis of Alzheimer's Disease and Estrogen-Induced Neuroprotection," Experimental Biology located at http://www.medicalnewstoday.com/releases/102971.php, last visited Feb. 10, 2015, two pages.

www.washington.edu, Diabetic Retinopathy, University of Washington, Sep. 1, 2006, printed from http://web.archive.org/web/20060901072856/http://faculty.washington.edu/chudler/diabr.html, 2 pages.

Yamauchi, R. et al. (1990). "Reaction of δ-Tocopherol with an Alkylperoxyl Radical," Agricultural and Biological Chemistry 54(11):2993-2999.

Yamauchi, R. et al. (1990). "Reaction Products of y-Tochopherol with an Alkylperoxyl Radical in Benzene," Agricultural and Biological Chemistry 54(10):2703-2709.

Yamauchi, R. et al. (1996). "Oxidation of alpha-Tocopherol during the Peroxidation of Dilinoleoylphosphatidylcholine in Liposomes," Bioscience, Biotechnology, and Biochemistry 60(4):616-620.

Yang, S.-G. et al. (Dec. 2010, e-pub. Oct. 7, 2010). "Alpha-Tocopherol Quinone Inhibits Beta-Amyloid Aggregation and Cytotoxicity, Disaggregates Preformed Fibrils and Decreases the Production of Reactive Oxygen Species, NO and Inflammatory Cytokines," Neurochemistry International 57(8):914-922.

Yarosh, et al., "The Molecular Mechanisms of OPA1-Mediated Optic Atrophy in *Drosophila* Model and Prospects for Antioxidant Treatment," *PLoS Genet*, vol. 4, No. 1, e6, Jan. 2008, pp. 62-71.

Yen, M-Y. et al. (2006); "Leber's Hereditary Optic Neuropathy: A Multifactorial Disease," Progress in Retinal and Eye Research 25:381-396.

Yim, S. et al. (2005); "A Continuous Spectrophotometric Assay for NADPH-cytochrome P450 Reductase Activity Using 3-(4,5-Dimethylthiazol-2-yl)-2,5-diphenyltetrazolium Bromide," Journal of Biochemistry and Molecular Biology 38(3):366-369.

Yu-Wai-Man, P. et al. (2009, e-pub. Nov. 17, 2008). "Inherited Mitochondrial Optic Neuropathies", *J. Med. Genet.* 46:145-158.

Yvon et al., Using Stem Cells to Model Diseases of the Outer Retina, *Comput Struct Biotechnol J*. May 6, 2015;13:382-9, printed from https://www.ncbi.nlm.nih.gov/pubmed/26106463, 2 pages, abstract only.

Zanna, C. et al. (2008). "OPA1 Mutations Associated with Dominant Optic Atrophy Impair Oxidative Phosphorylation and Mitochondrial Fusion," Brain 131(2):352-367.

Zheng, A. et al. (1999). "A Redox-Sensitive Resin Linker for the Solid Phase Synthesis of C-Terminal Modified Peptides," *Journal of Organic Chemistry* 64:156-161.

Zwaiyed, F.R. et al. (2003). "Vitamin E and its Derivative Antihypoxic Effectivity in Rats Under Modeling of Hypoxic Conditions of Different Origin," *Ukrainskii Biokhimicheskii Zhurnal* 75(2):67-71.

International Search Report and Written Opinion of PCT/US2016/067404 dated Apr. 28, 2017, 17 pages.

Duveau et al., "Synthesis and characterization of mitoQ and idebenone analogues as mediators of oxygen consumption in mitochondria", *Bioorganic & Medicinal Chemistry*, Pergamon, GB, Sep. 1, 2010, vol. 18, No. 17, pp. 6429-6441, XP027218831.

Hargreaves et al., "Glutathione deficiency in patients with mitochondrial disease: Implications for pathogenesis and treatment", J. Inherit. Metab. Dis. 28 (2005), pp. 81-88.

Kasper et al., "Harrison's Principles of Internal Medicine", Sixteenth Edition, 2005, ISBN 007-1391404 (set)—ISBN 0-07-139141-X (v. 1)—ISBN 0-07-139142-8 (v. 2)—ISBN 0-07-140235-7 (combo); 6 pages.

Patel, "Mitochondrial Dysfunction and Oxidative Stress: Cause and Consequence of Epileptic Seizures", Free Radical Biology & Medicine, doi:10.1016/j.freeradbiomed.2004.08.021, 2004, pp. 1951-1962.

Napolitano et al., "Long-term treatment with idebenone and riboflavin in a patient with MELAS", Neurol Sci, 2000, vol. 21, pp. S981-S982.

Rötig et al., "Molecular insights into Friedreich's ataxia and antioxidant-based therapies", Trends in Molecular Medicine, vol. 8, No. 5, May 2002, pp. 221-224.

Taylor et al., "Mitochondrial DNA Mutations in Human Disease", Nature Reviews/Genetics, vol. 6, May 2005, pp. 389-402.

Viscomi et al., "Emerging concepts in the therapy of mitochondrial disease". Biochimica et Biophysica Acta. 1847, 2015, pp. 544-557.

\* cited by examiner

FLUOROALKYL, FLUOROALKOXY, PHENOXY, HETEROARYLOXY, ALKOXY, AND AMINE 1,4-BENZOQUINONE DERIVATIVES FOR TREATMENT OF OXIDATIVE STRESS DISORDERS

This application is a national phase entry of PCT International Application No. PCT/US2016/67404, filed on Dec. 17, 2016, which claims priority to U.S. Provisional Application No. 62/269,016 filed on Dec. 17, 2015, which are incorporated herein by reference in their entirety.

This application claims priority to, and the benefit of, U.S. Provisional Patent Application No. 62/269,016, entitled FLOUROALKYL, FLOUROALKOXY, AND METHOXY 1,4-BENZOQUINONE DERIVATIVES FOR TREATMENT OF OXIDATIVE STRESS DISORDERS, which was filed Dec. 17, 2015. The content of this provisional patent application is herein incorporated by reference in its entirety for all purposes.

TECHNICAL FIELD

The application discloses compositions and methods useful for treatment or suppression of diseases, developmental delays and symptoms related to oxidative stress disorders. Examples of such disorders include mitochondrial disorders, impaired energy processing disorders, neurodegenerative diseases and diseases of aging. The application further discloses compositions and methods useful for prophylactically protecting organisms against and/or treating organisms for damage caused by exposure to radiation.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide (NADH+H+) from oxidized nicotinamide adenine dinucleotide (NAD+), and oxidative phosphorylation, during which NADH+H+ is oxidized back to NAD+. (The citric acid cycle also reduces flavin adenine dinucleotide, or FAD, to FADH2; FADH2 also participates in oxidative phosphorylation.)

The electrons released by oxidation of NADH+H+ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues results in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, encephalomyopathy, lactacidosis, and stroke (MELAS), Myoclonus Epilepsy Associated with Ragged-Red Fibers (MERRF) syndrome, Leigh's Syndrome, Leigh-like Syndrome, and respiratory chain disorders. Most mitochondrial diseases involve children who manifest the signs and symptoms of accelerated aging, including neurodegenerative diseases, stroke, blindness, hearing impairment, vision impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh Disease or Leigh Syndrome is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) Neuromusc. Disord., 15:311-315), childhood-onset cerebellar ataxia and cerebellar atrophy (Masumeci et al., (2001) Neurology 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) Brain, 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hypotonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, where patients typically are normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

Maternally inherited diabetes and deafness (MIDD) is a mitochondrial disorder characterized by maternally transmitted diabetes and sensorineural deafness. In most cases, MIDD is caused by a point mutation in the mitochondrial gene MT-TL1, encoding the mitochondrial tRNA for leucine, and in rare cases in MT-TE and MT-TK genes, encoding the mitochondrial tRNAs for glutamic acid, and lysine, respectively.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic, neuronal injury, such as that associated with cerebrovascular accidents, seizures and ischemia.

Some of the diseases disclosed herein, including the above diseases, appear to be caused by defects in Complex I of the respiratory chain. Electron transfer from Complex I to the remainder of the respiratory chain is mediated by the compound coenzyme Q (also known as Ubiquinone). Oxidized coenzyme Q (CoQox or Ubiquinone) is reduced by Complex I to reduced coenzyme Q (CoQred or Ubiquinol). The reduced coenzyme Q then transfers its electrons to Complex III of the respiratory chain, where it is re-oxidized to CoQox (Ubiquinone). CoQox can then participate in further iterations of electron transfer.

Very few treatments are available for patients suffering from these mitochondrial diseases. Recently, the compound Idebenone has been proposed for treatment of Friedreich's Ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), Aging—A theory based on free-radical and radiation chemistry J. Gerontol. 11, 298-300.

According to the free radical theory of aging, the process of aging begins with oxygen metabolism (Valko et al, (2004) Role of oxygen radicals in DNA damage and cancer incidence, Mol. Cell. Biochem., 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, Free Radic. Res, 28, 601-609). The cell repairs much of the damage done to nuclear DNA (nDNA) but mtDNA repair seems to be less efficient. Therefore, extensive mtDNA damage accumulates over time and shuts down mitochondria causing cells to die and the organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described herein. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. In some embodiments, if an individual is undergoing an extremely strenuous undertaking, it can be desirable to raise the level of ATP in that individual.

Exposure to radiation is a well-known cause of damage to cells, tissues, and organisms. Ionizing radiation such as high-frequency ultraviolet radiation, X-rays, gamma rays, alpha radiation, and beta radiation can break chemical bonds, leading to damage to biological molecules in cells. Damage to DNA is particularly deleterious, and is known to cause cancer and other pathologies. Further discussion of these effects can be found in, for example, International Patent Publication WO 2010/045220.

Exposure to ionizing radiation may occur during medical procedures, such as radiography, fluoroscopy, dental X-rays, and CT scans. People who routinely work with radiation or radioactive materials, such as X-ray technicians or nuclear medicine specialists, may also be inadvertently exposed to radiation. Exposure to radiation may also occur due to accidental release of radioactive materials into the environment, such as the 2011 Fukushima disaster or the 1979 Three Mile Island accident, or deliberate release of radioactive materials such as a "dirty bomb."

There is thus a need for radioprotective agents that can mitigate the adverse effects of exposure to radiation.

BRIEF SUMMARY OF THE INVENTION

In one aspect is a compound of the formula I:

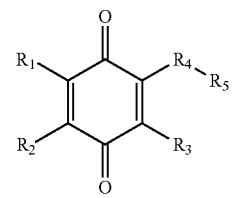

(I)
or the hydroquinone form thereof; wherein: $R_1$ and $R_2$ are independently $C_1$-$C_{10}$ alkyl; $R_3$ is $C_1$-$C_6$ alkyl; $R_4$ is $C_6$-$C_{12}$ alkyl and $R_5$ is —$CF_3$, wherein $R_5$ is attached to $R_4$ at any chemically possible location on the $C_6$-$C_{12}$ alkyl group; or $R_4$ is $C_1$-$C_{12}$ n-alkyl and $R_5$ is —$OCH_3$, —$OCF_3$, or —$OCH_2CF_3$, wherein $R_5$ is attached to $R_4$ at any chemically possible location on the $C_1$-$C_{12}$ n-alkyl group; or a salt, a stereoisomer, or mixture of stereoisomers thereof; with the proviso that the compound is not

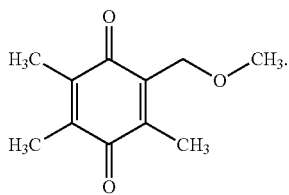

In some embodiments, the compound is a quinone. In some embodiments, the compound is a hydroquinone. In some embodiments, including any of the foregoing embodiments, $R_1$ and $R_2$ are independently $C_1$-$C_6$ alkyl. In some embodiments, including any of the foregoing embodiments, $R_1$ and $R_2$ are independently $C_1$-$C_4$ alkyl. In some embodiments, including any of the foregoing embodiments, $R_1$ and $R_2$ are independently $C_1$-$C_2$ alkyl. In some embodiments, including any of the foregoing embodiments, $R_1$ and $R_2$ are methyl. In some embodiments, including any of the foregoing embodiments, one of $R_1$ and $R_2$ is a n-alkyl. In some embodiments, including any of the foregoing embodiments, $R_1$ and $R_2$ are both n-alkyl. In some embodiments, including any of the foregoing embodiments, one of $R_1$ and $R_2$ is a branched alkyl. In some embodiments, including any of the foregoing embodiments, $R_1$ and $R_2$ are both branched alkyl. In some embodiments, including any of the foregoing embodiments, one of $R_1$ and $R_2$ comprises a cycloalkyl group. In some embodiments, including any of the foregoing embodiments, $R_1$ and $R_2$ each comprise a cycloalkyl group. In some embodiments, including any of the foregoing embodiments, $R_3$ is $C_1$-$C_4$ alkyl. In some embodiments, including any of the foregoing embodiments, $R_3$ is $C_1$-$C_3$ alkyl. In some embodiments, including any of the foregoing embodiments, $R_3$ is $C_1$-$C_2$ alkyl. In some embodiments, including any of the foregoing embodiments, $R_3$ is methyl. In some embodiments, including any of the foregoing embodiments, $R_3$ is isopropyl. In some embodiments, including any of the foregoing embodiments, $R_3$ is an n-alkyl. In some embodiments, including any of the foregoing embodiments, $R_3$ is a branched alkyl. In some embodiments, including any of the foregoing embodiments, $R_3$ comprises a cycloalkyl group. In some embodiments, including any of the foregoing embodiments, $R_5$ is —$CF_3$. In some embodiments, including any of the foregoing embodiments, $R_5$ is —$OCH_3$. In some embodiments, including any of the foregoing embodiments, $R_5$ is —$OCF_3$. In some embodiments, including any of the foregoing embodiments, $R_5$ is —$OCH_2CF_3$. In some embodiments, including any of the foregoing embodiments, $R_4$ is $C_6$-$C_{12}$ alkyl for all values of $R_5$. In some embodiments, including any of the foregoing embodiments, $R_4$ is $C_6$-$C_{10}$ alkyl for all values of $R_5$. In some embodiments, including any of the foregoing embodiments, $R_4$ is $C_8$-$C_{10}$ alkyl for all values of $R_5$. In some embodiments, including any of the foregoing embodiments, $R_4$ is a n-alkyl for all values of $R_5$. In some embodiments, including any of the foregoing embodiments, $R_4$ is a branched alkyl. In some embodiments, including any of the foregoing embodiments, $R_4$ comprises a cycloalkyl group. In some embodiments, including any of the foregoing embodiments, $R_4$ is $C_6$ alkyl. In some embodiments, including any of the foregoing embodiments, $R_4$ is $C_7$ alkyl. In some embodiments, including any of the foregoing embodiments, $R_4$ is $C_8$ alkyl. In some embodiments, including any of the foregoing embodiments, $R_4$ is $C_9$ alkyl. In some embodiments, including any of the foregoing embodiments, $R_4$ is $C_{10}$ alkyl. In some embodiments, including any of the foregoing embodiments, $R_4$ is $C_{11}$ alkyl. In some embodiments, including any of the foregoing embodiments, $R_4$ is $C_{12}$ alkyl. In some embodiments, including any of the foregoing embodiments, $R_4$ is $C_6$ n-alkyl. In some embodiments, including any of the foregoing embodiments, $R_4$ is $C_7$ n-alkyl. In some embodiments, including any of the foregoing embodiments, $R_4$ is $C_8$ n-alkyl. In some embodiments, including any of the foregoing embodiments, $R_4$ is $C_9$ n-alkyl. In some embodiments, including any of the foregoing embodiments, $R_4$ is $C_{10}$ n-alkyl. In some embodiments, including any of the foregoing embodiments, $R_4$ is $C_{11}$ n-alkyl. In some embodiments, including any of the foregoing embodiments, $R_4$ is $C_{12}$ n-alkyl. In some embodiments, including any of the foregoing embodiments when $R_4$ is $C_1$-$C_{12}$ n-alkyl, $R_4$ is $C_1$ alkyl. In some embodiments, including any of the foregoing embodiments when $R_4$ is $C_1$-$C_{12}$ n-alkyl, $R_4$ is $C_2$ alkyl. In some embodiments, including any of the foregoing embodiments when $R_4$ is $C_1$-$C_{12}$ n-alkyl, $R_4$ is $C_3$ alkyl. In some embodiments, including any of the foregoing embodiments when $R_4$ is $C_1$-$C_{12}$ n-alkyl, $R_4$ is $C_4$ alkyl. In some embodiments, including any of the foregoing embodiments when $R_4$ is $C_1$-$C_{12}$ n-alkyl, $R_4$ is $C_5$ alkyl. In some embodiments, the compound is:

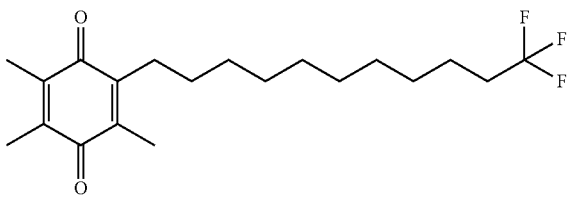

or the hydroquinone form thereof. In some embodiments, the compound is:

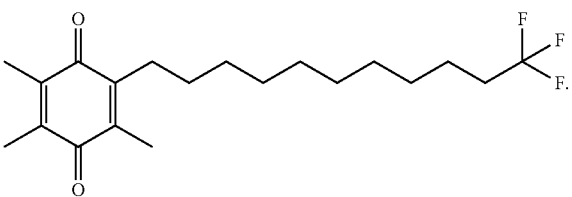 [SMILES: CC1=C(C)C(=O)C(CCCCCCCCCCC(F)(F)F)=C(C)C1=O]

In some embodiments, the compound is:

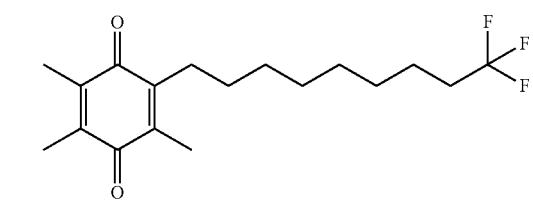 [SMILES: CC1=C(C)C(=O)C(CCCCCCCCC(F)(F)F)=C(C)C1=O]

or the hydroquinone form thereof. In some embodiments, the compound is:

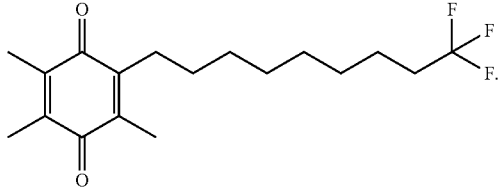 [SMILES: CC1=C(C)C(=O)C(CCCCCCCCC(F)(F)F)=C(C)C1=O]

In some embodiments, the compound is:

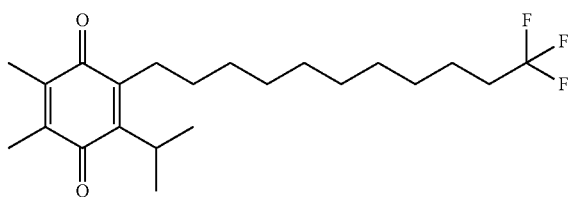 [SMILES: CC1=C(C)C(=O)C(C(C)C)=C(CCCCCCCCCCC(F)(F)F)C1=O]

or the hydroquinone form thereof. In some embodiments, the compound is:

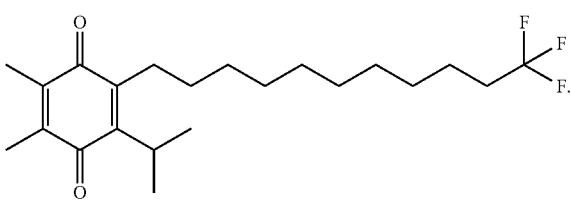 [SMILES: CC1=C(C)C(=O)C(C(C)C)=C(CCCCCCCCCCC(F)(F)F)C1=O]

In some embodiments, the compound is:

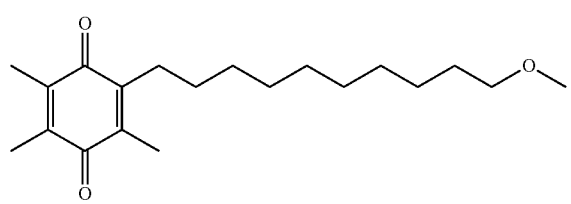

or the hydroquinone form thereof. In some embodiments, the compound is:

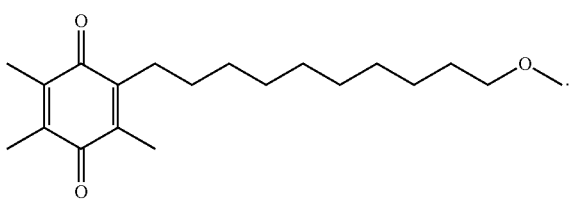

In some embodiments, the compound is:

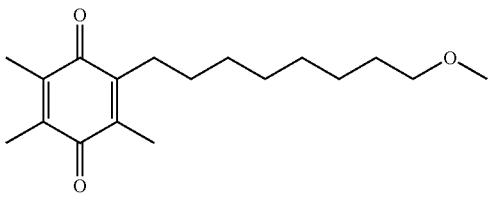

or the hydroquinone form thereof. In some embodiments, the compound is:

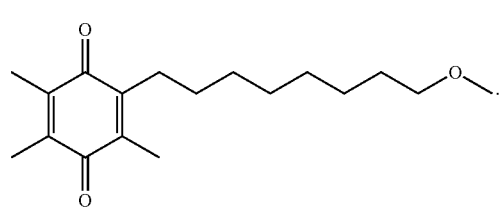

In some embodiments, the compound is:

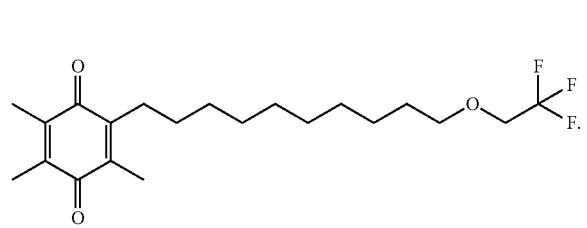

or the hydroquinone form thereof. In some embodiments, the compound is:

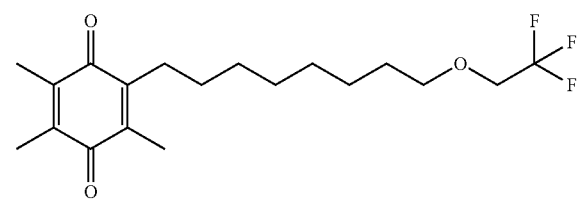 [SMILES: CC1=C(C)C(=O)C(CCCCCCCCOCC(F)(F)F)=C(C)C1=O]

or the hydroquinone form thereof. In some embodiments, the compound is:

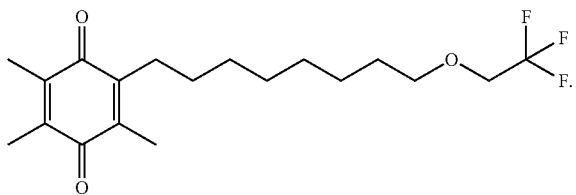 [SMILES: CC1=C(C)C(=O)C(CCCCCCCCOCC(F)(F)F)=C(C)C1=O]

In some embodiments, the compound is:

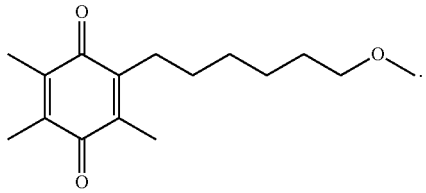

In some embodiments, including any of the foregoing embodiments, $R_1$ and $R_2$ are independently $C_1$-$C_4$ alkyl; and $R_3$ is $C_1$-$C_4$ alkyl. In some embodiments, including any of the foregoing embodiments, $R_1$, $R_2$ and $R_3$ are methyl. In some embodiments, including any of the foregoing embodiments, $R_1$ and $R_2$ are methyl; and $R_3$ is $C_1$-$C_4$ alkyl. In some embodiments, including any of the foregoing embodiments, $R_1$ and $R_2$ are methyl; and $R_3$ is isopropyl. In some embodiments, including any of the foregoing embodiments, $R_1$ and $R_2$ are independently $C_1$-$C_4$ alkyl; $R_3$ is $C_1$-$C_4$ alkyl; $R_4$ is $C_8$-$C_{10}$ alkyl and $R_5$ is —$CF_3$, wherein $R_5$ is attached to $R_4$ at any chemically possible location on the $C_8$-$C_{10}$ alkyl group; or $R_4$ is $C_8$-$C_{10}$ n-alkyl and $R_5$ is —$OCH_3$, —$OCF_3$, or —$OCH_2CF_3$, wherein $R_5$ is attached to $R_4$ at any chemically possible location on the $C_8$-$C_{10}$ n-alkyl group; or a salt, a stereoisomer, or mixture of stereoisomers thereof. In some embodiments, including any of the foregoing embodiments, $R_1$ and $R_2$ are independently $C_1$-$C_4$ alkyl; $R_3$ is $C_1$-$C_4$ alkyl; $R_4$ is $C_8$-$C_{10}$ alkyl and $R_5$ is —$CF_3$, wherein $R_5$ is attached to $R_4$ at the $R_4$ carbon furthest from the quinone or hydroquinone ring; or $R_4$ is $C_8$-$C_{10}$ n-alkyl and $R_5$ is —$OCH_3$, —$OCF_3$, or —$OCH_2CF_3$, wherein $R_5$ is attached to $R_4$ at the $R_4$ carbon furthest from the quinone or hydroquinone ring; or a salt, a stereoisomer, or mixture of stereoisomers thereof. In some embodiments, including any of the foregoing embodiments, $R_4$ is $C_6$-$C_{12}$ alkyl and $R_5$ is —$CF_3$, wherein $R_5$ is attached to $R_4$ at the $R_4$ carbon furthest from the quinone or hydroquinone ring; or $R_4$ is $C_7$-$C_{12}$ n-alkyl and $R_5$ is —$OCH_3$, —$OCF_3$, or —$OCH_2CF_3$, wherein $R_5$ is attached to $R_4$ at the $R_4$ carbon furthest from the quinone or hydroquinone ring. In some embodiments, including any of the foregoing embodiments, the compound is not

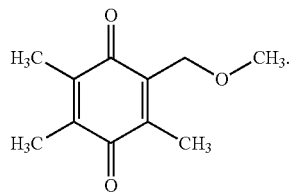

In some embodiments, including any of the foregoing embodiments, the compound is not a salt. In some embodiments, including any of the foregoing embodiments, the compound is a salt. In some embodiments, including any of the foregoing embodiments, the compound is a pharmaceutically acceptable salt. Compositions comprising combinations of compounds disclosed herein are also contemplated.

In another aspect is a compound of the formula II:

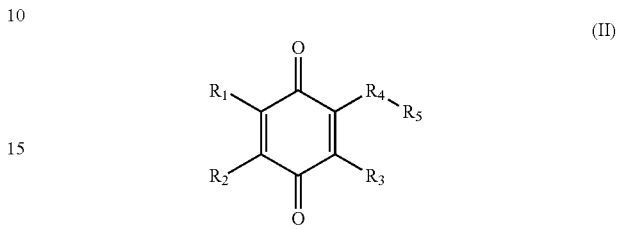

or the hydroquinone form thereof; wherein: $R_1$ and $R_2$ are independently $C_1$-$C_{10}$ alkyl; $R_3$ is $C_1$-$C_6$ alkyl or —NHS$(O)_2CH_3$; $R_4$ is $C_8$-$C_{12}$ n-alkyl and $R_5$ is $C_1$ haloalkyl, —O—$C_1$-$C_6$ alkyl, —O—$C_1$-$C_6$ haloalkyl, —O-phenyl, —O-heteroaryl, or —$NR_6R_7$, wherein $R_5$ is attached to $R_4$ at any chemically possible location on the $C_8$-$C_{12}$ n-alkyl group; or $R_4$ is $C_8$-$C_{12}$ alkyl and $R_5$ is $C_1$ haloalkyl, —O—$C_2$-$C_6$ alkyl, —O—$C_3$-$C_6$ haloalkyl, —O-phenyl, —O-heteroaryl, or —$NR_6R_7$, wherein $R_5$ is attached to $R_4$ at any chemically possible location on the $C_8$-$C_{12}$ alkyl group; $R_6$ and $R_7$ are independently selected from the group consisting of H and $C_1$-$C_6$ alkyl; or $R_6$ and $R_7$ together with the nitrogen atom to which they are attached form a 3-7 membered saturated heterocyclic ring; and phenyl and heteroaryl are optionally independently substituted with 1-4 $C_1$-$C_4$ alkyl substituents; or a salt, a stereoisomer, or mixture of stereoisomers thereof; wherein: when $R_4$ is $C_8$ n-alkyl, then $R_5$ is not $CF_3$; when $R_4$ is $C_9$ n-alkyl, then $R_5$ is not $CH_2Br$; and when $R_4$ is $C_{10}$ n-alkyl, then $R_5$ is not O—$CH_3$ or O—$CH_2$—$CF_3$. In some embodiments, the compound is a quinone. In some embodiments, the compound is a hydroquinone. In some embodiments, including any of the foregoing embodiments, $R_1$ and $R_2$ are independently $C_1$-$C_6$ alkyl. In some embodiments, including any of the foregoing embodiments, $R_1$ and $R_2$ are independently $C_1$-$C_4$ alkyl. In some embodiments, including any of the foregoing embodiments, $R_1$ and $R_2$ are independently $C_1$-$C_2$ alkyl. In some embodiments, including any of the foregoing embodiments, $R_1$ and $R_2$ are methyl. In some embodiments, including any of the foregoing embodiments, one of $R_1$ and $R_2$ is a n-alkyl. In some embodiments, including any of the foregoing embodiments, $R_1$ and $R_2$ are both n-alkyl. In some embodiments, including any of the foregoing embodiments, one of $R_1$ and $R_2$ is a branched alkyl. In some embodiments, including any of the foregoing embodiments, $R_1$ and $R_2$ are both branched alkyl. In some embodiments, including any of the foregoing embodiments, one of $R_1$ and $R_2$ comprises a cycloalkyl group. In some embodiments, including any of the foregoing embodiments, $R_1$ and $R_2$ each comprise a cycloalkyl group. In some embodiments, including any of the foregoing embodiments, $R_3$ is —NHS$(O)_2CH_3$. In some embodiments, including any of the foregoing embodiments, $R_3$ is $C_1$-$C_4$ alkyl. In some embodiments, including any of the foregoing embodiments, $R_3$ is $C_1$-$C_3$ alkyl. In some embodiments, including any of the foregoing embodiments, $R_3$ is $C_1$-$C_2$ alkyl. In some embodiments, including any of the foregoing embodiments, $R_3$ is methyl. In some embodiments, including any of the foregoing embodiments, $R_3$ is isopropyl. In some embodiments, including any of the foregoing embodiments, $R_3$ is an n-alkyl. In some embodiments, including any of the foregoing embodiments, $R_3$ is a branched alkyl. In some embodiments, including any of the foregoing embodiments, $R_3$ comprises a cycloalkyl group. In some embodiments, including any of the foregoing embodiments, $R_5$ is —$CF_3$. In some embodiments, including any of the foregoing embodiments, $R_5$ is —$OCH_3$. In some embodiments, including any of the foregoing embodiments, $R_5$ is —$OCF_3$. In some embodiments, including any of the foregoing embodiments, $R_5$ is —$OCH_2CF_3$. In some embodiments, including any of the foregoing embodiments, $R_5$ is —O—$CH(CH_3)_2$. In some embodiments, including any of the foregoing embodiments, $R_5$ is —$OCH_2CH_3$. In some embodiments, including any of the foregoing embodiments, $R_5$ is —$OCH_2CH_2CH_3$. In some embodiments, including any of the foregoing embodiments, $R_5$ is —O—$CH_2CH(CH_3)_2$. In some embodiments, including any of the foregoing embodiments, $R_5$ is —O-phenyl. In some embodiments, including any of the foregoing embodiments, $R_5$ is —O-heteroaryl and heteroaryl is 2-methylpyridyl. In some embodiments, including any of the foregoing embodiments, $R_5$ is —$NR_6R_7$. In some embodiments, including any of the foregoing embodiments, $R_6$ and $R_7$ are independently selected from the group consisting of H and $C_1$-$C_6$ alkyl. In some embodiments, including any of the foregoing embodiments, $R_6$ and $R_7$ are independently selected from the group consisting of methyl, ethyl, n-propyl, iso-propyl, n-butyl, tert-butyl, sec-butyl, and iso-butyl. In some embodiments, including any of the foregoing embodiments, $R_6$ and $R_7$ are selected from methyl and iso-butyl. In some embodiments, including any of the foregoing embodiments, $R_6$ and $R_7$ together with the nitrogen atom to which they are attached form a 3-7 membered saturated heterocyclic ring. In some embodiments, including any of the foregoing embodiments, $R_6$ and $R_7$ together with the nitrogen atom to which they are attached form pyrrolidinyl. In some embodiments, including any of the foregoing embodiments, $R_5$ is $C_1$ haloalkyl. In some embodiments, including any of the foregoing embodiments, $R_5$ is —O—$C_2$-$C_6$ alkyl. In some embodiments, including any of the foregoing embodiments, $R_5$ is —O—$C_3$-$C_6$ haloalkyl. In some embodiments, including any of the foregoing embodiments, $R_5$ is —O-phenyl. In some embodiments, including any of the foregoing embodiments, $R_5$ is —O-phenyl substituted with 1-4 substituents selected from $C_1$-$C_4$ alkyl. In some embodiments, including any of the foregoing embodiments, $R_5$ is —O— heteroaryl. In some embodiments, including any of the foregoing embodiments, $R_5$ is —O— heteroaryl substituted with 1-4 substituents selected from $C_1$-$C_4$ alkyl. In some embodiments, including any of the foregoing embodiments, $R_5$ is —O—$C_1$-$C_6$ alkyl. In some embodiments, including any of the foregoing embodiments, $R_5$ is —O—$C_1$-$C_6$ haloalkyl. In some embodiments, including any of the foregoing embodiments, $R_4$ is $C_8$-$C_{10}$ alkyl for all values of $R_5$. In some embodiments, including any of the foregoing embodiments, $R_4$ is a n-alkyl for all values of $R_5$. In some embodiments, including any of the foregoing embodiments, $R_4$ is a branched alkyl. In some embodiments, including any of the foregoing embodiments, $R_4$ comprises a cycloalkyl group. In some embodiments, including any of the foregoing embodiments, $R_4$ is $C_8$ alkyl. In some embodiments, including any of the foregoing embodiments, $R_4$ is $C_9$ alkyl. In some embodiments, including any of the foregoing embodiments, $R_4$ is $C_{10}$ alkyl. In some embodiments, including any of the foregoing embodiments, $R_4$ is $C_{11}$ alkyl. In some embodiments, including any of the foregoing embodiments, $R_4$ is $C_{12}$ alkyl. In some embodiments, the compound is:

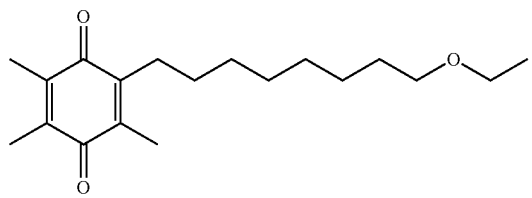 [SMILES: CCOCCCCCCCCC1=C(C)C(=O)C(C)=C(C)C1=O]

or the hydroquinone form thereof. In some embodiments, the compound is:

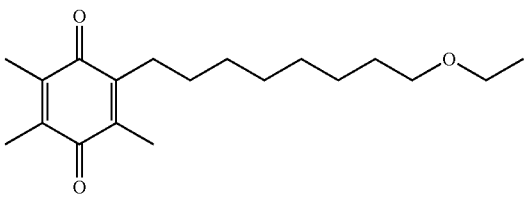

In some embodiments, the compound is:

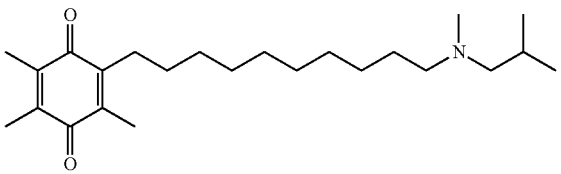 [SMILES: CC1=C(C)C(=O)C(CCCCCCCCCCN(C)CC(C)C)=C(C)C1=O]

or the hydroquinone form thereof; or a salt thereof. In some embodiments, the compound is:

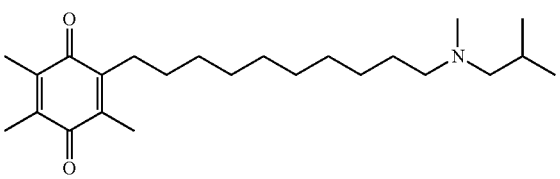

or a salt thereof. In some embodiments, the compound is:

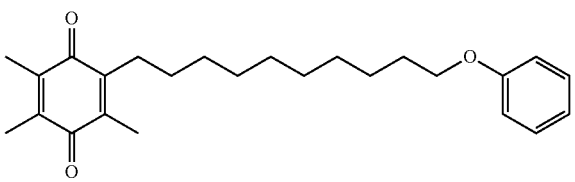 [SMILES: CC1=C(C)C(=O)C(CCCCCCCCCCOc2ccccc2)=C(C)C1=O]

or the hydroquinone form thereof. In some embodiments, the compound is:

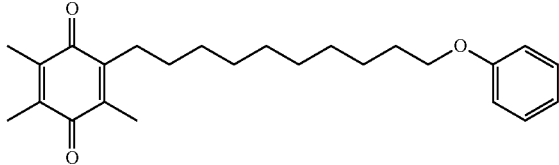

In some embodiments, the compound is:

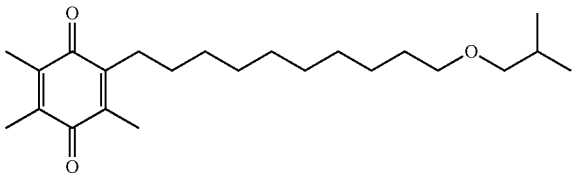 [SMILES: CC1=C(C)C(=O)C(CCCCCCCCCCOCC(C)C)=C(C)C1=O]

or the hydroquinone form thereof. In some embodiments, the compound is:

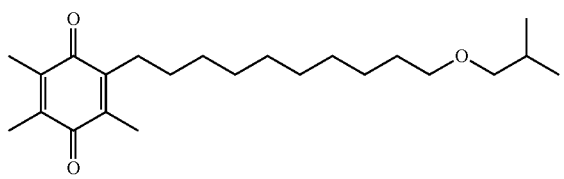

In some embodiments, the compound is:

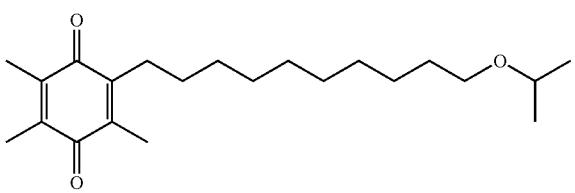 [SMILES: CC1=C(C)C(=O)C(CCCCCCCCCCOC(C)C)=C(C)C1=O]

or the hydroquinone form thereof. In some embodiments, the compound is:

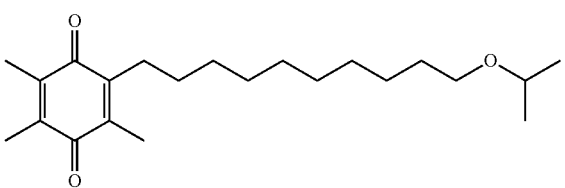

In some embodiments, the compound is:

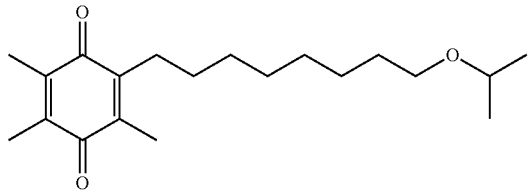

or the hydroquinone form thereof. In some embodiments, the compound is:

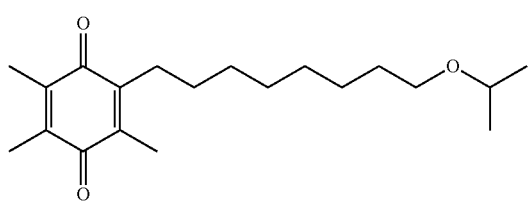 [SMILES: CC1=C(C)C(=O)C(CCCCCCCCOC(C)C)=C(C)C1=O]

In some embodiments, the compound is:

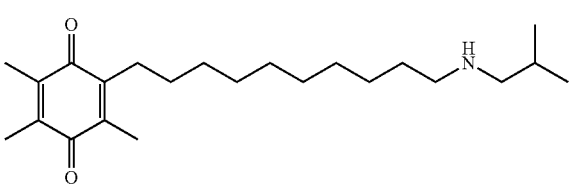

or the hydroquinone form thereof; or a salt thereof. In some embodiments, the compound is:

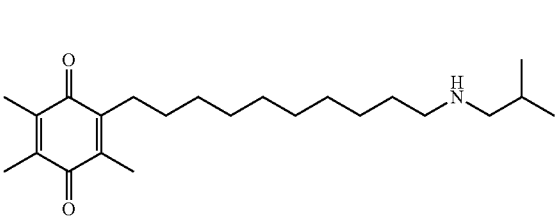 [SMILES: CC1=C(C)C(=O)C(CCCCCCCCCCNCC(C)C)=C(C)C1=O]

or a salt thereof. In some embodiments, the compound is:

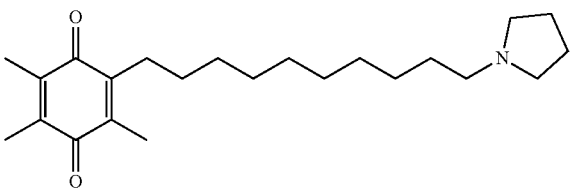 [SMILES: CC1=C(C)C(=O)C(CCCCCCCCCCN2CCCC2)=C(C)C1=O]

or the hydroquinone form thereof; or a salt thereof. In some embodiments, the compound is:

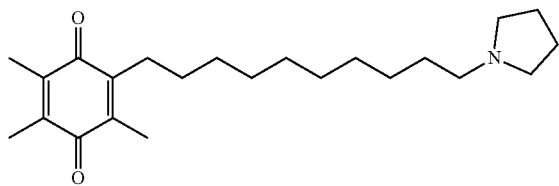

or a salt thereof. In some embodiments, the compound is:

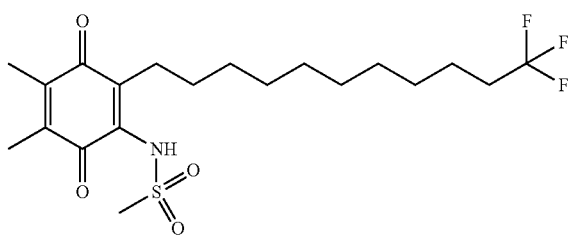 [SMILES: CC1=C(C)C(=O)C(NS(C)(=O)=O)=C(CCCCCCCCCCC(F)(F)F)C1=O]

or the hydroquinone form thereof; or a salt thereof. In some embodiments, the compound is:

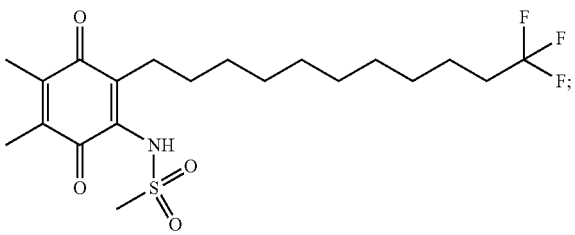 [SMILES: CC1=C(C)C(=O)C(NS(C)(=O)=O)=C(CCCCCCCCCCC(F)(F)F)C1=O]

or a salt thereof. In some embodiments, the compound is:

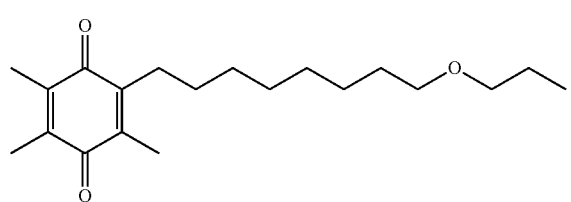 [SMILES: CCCOCCCCCCCCC1=C(C)C(=O)C(C)=C(C)C1=O]

or the hydroquinone form thereof. In some embodiments, the compound is:

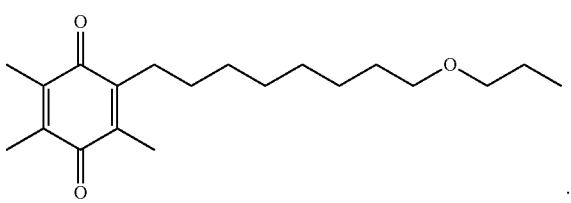 [SMILES: CCCOCCCCCCCCC1=C(C)C(=O)C(C)=C(C)C1=O]

In some embodiments, the compound is:

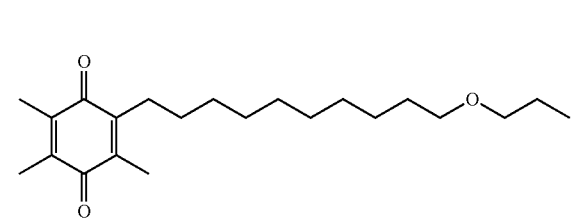 [SMILES: CCCOCCCCCCCCCCC1=C(C)C(=O)C(C)=C(C)C1=O]

or the hydroquinone form thereof. In some embodiments, the compound is:

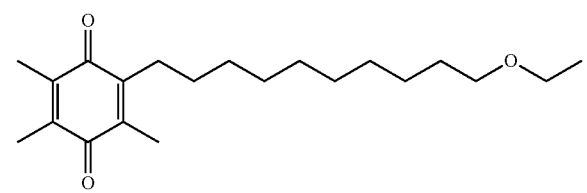 [SMILES: CCOCCCCCCCCCCC1=C(C)C(=O)C(C)=C(C)C1=O]

In some embodiments, the compound is:

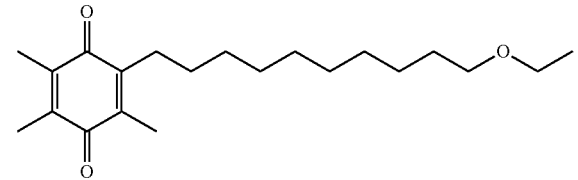

or the hydroquinone form thereof. In some embodiments, the compound is:

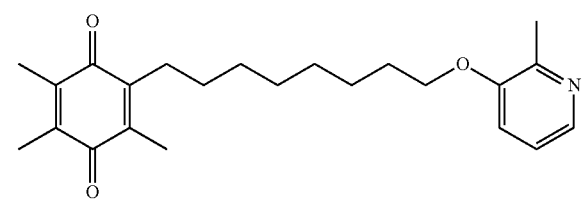 [SMILES: CC1=C(C)C(=O)C(CCCCCCCCOc2cccnc2C)=C(C)C1=O]

In some embodiments, the compound is:

or the hydroquinone form thereof; or a salt thereof. In some embodiments, the compound is:

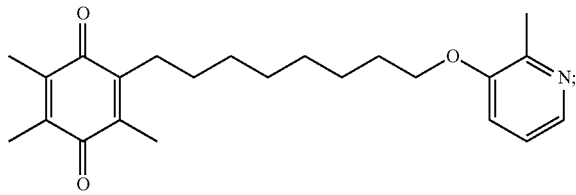 [SMILES: CC1=C(C)C(=O)C(CCCCCCCCOc2cccnc2C)=C(C)C1=O]

or a salt thereof.

In another aspect is a pharmaceutical composition comprising a compound as described herein (including but not limited to a compound described in the above paragraphs) and a pharmaceutically acceptable carrier. In another aspect is a pharmaceutical composition comprising an active agent and a pharmaceutically acceptable carrier, wherein the active agent consists of, or consists essentially of, a compound as described herein (including but not limited to a compound described in the above paragraphs). Any one or more of the compounds described herein, including all of the foregoing compounds, can be formulated into a unit dose formulation.

In another aspect is a method of treating or suppressing an oxidative stress disorder, modulating one or more energy biomarkers, normalizing one or more energy biomarkers, or enhancing one or more energy biomarkers, comprising administering to a subject in need thereof a therapeutically effective amount or effective amount of a compound or composition as described herein (including but not limited to a compound described in the above paragraphs). In some embodiments, the method of treating or suppressing an oxidative stress disorder, modulating one or more energy biomarkers, normalizing one or more energy biomarkers, or enhancing one or more energy biomarkers, comprises administering to a subject in need thereof a therapeutically effective amount or effective amount of a compound of the formula I:

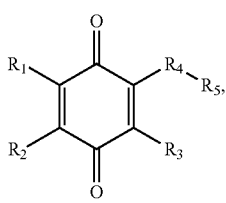

(I)

or the hydroquinone form thereof wherein: $R_1$ and $R_2$ are independently $C_1$-$C_{10}$ alkyl; $R_3$ is $C_1$-$C_6$ alkyl; $R_4$ is $C_6$-$C_{12}$ alkyl and $R_5$ is —$CF_3$, wherein $R_5$ is attached to $R_4$ at any chemically possible location on the $C_6$-$C_{12}$ alkyl group; or $R_4$ is $C_1$-$C_{12}$ n-alkyl and $R_5$ is —$OCH_3$, —$OCF_3$, or —$OCH_2CF_3$, wherein $R_5$ is attached to $R_4$ at any chemically possible location on the $C_1$-$C_{12}$ n-alkyl group; or a pharmaceutically acceptable salt, a stereoisomer, or mixture of stereoisomers thereof. In some embodiments, the method of treating or suppressing an oxidative stress disorder, modulating one or more energy biomarkers, normalizing one or more energy biomarkers, or enhancing one or more energy biomarkers, comprises administering to a subject in need thereof a therapeutically effective amount or effective amount of a compound of the formula II:

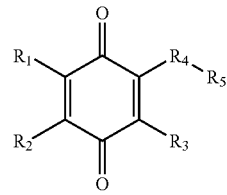

(II)

or the hydroquinone form thereof; wherein: $R_1$ and $R_2$ are independently $C_1$-$C_{10}$ alkyl; $R_3$ is $C_1$-$C_6$ alkyl or —NHS$(O)_2CH_3$; $R_4$ is $C_8$-$C_{12}$ alkyl and $R_5$ is $C_1$ haloalkyl, —O—$C_2$-$C_6$ alkyl, —O—$C_3$-$C_6$ haloalkyl, —O-phenyl, —O-heteroaryl, or —$NR_6R_7$, wherein $R_5$ is attached to $R_4$ at any chemically possible location on the $C_8$-$C_{12}$ alkyl group; or $R_4$ is $C_8$-$C_{12}$ n-alkyl and $R_5$ is $C_1$ haloalkyl, —O—$C_1$-$C_6$ alkyl, —O—$C_1$-$C_6$ haloalkyl, —O-phenyl, —O-heteroaryl, or —$NR_6R_7$, wherein $R_5$ is attached to $R_4$ at any chemically possible location on the $C_8$-$C_{12}$ n-alkyl group; $R_6$ and $R_7$ are independently selected from the group consisting of H and $C_1$-$C_6$ alkyl; or $R_6$ and $R_7$ together with the nitrogen atom to which they are attached form a 3-7 membered saturated heterocyclic ring; and phenyl and heteroaryl are optionally independently substituted with 1-4 $C_1$-$C_4$ alkyl substituents; or a pharmaceutically acceptable salt, a stereoisomer, or mixture of stereoisomers thereof; wherein when $R_4$ is $C_{8\ n}$-alkyl, then $R_5$ is not $CF_3$; and when $R_4$ is $C_{10}$ n-alkyl, then $R_5$ is not O—$CH_3$ or O—$CH_2$—$CF_3$. In some embodiments, including any of the foregoing embodiments, the compound is not a salt. In some embodiments, including any of the foregoing embodiments, the compound is a pharmaceutically acceptable salt. The method can use any individual compound as described herein, or a combination of compounds. In some embodiments, including any of the foregoing embodiments, the compound is administered as a pharmaceutical composition comprising the compound and a pharmaceutically acceptable carrier. In some embodiments, including any of the foregoing embodiments, the pharmaceutical composition comprises an active agent consisting essentially of the compound, and a pharmaceutically acceptable carrier. In some embodiments, the method is a method of treating or suppressing an oxidative stress disorder selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II deficiency; Friedreich's Ataxia (FA); Glutaric Aciduria Type II; Kearns-Sayre Syndrome (KSS); Lactic Acidosis; Long-Chain Acyl-CoA Dehydrongenase Deficiency (LOAD); LCHAD; Leigh Syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrongenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy; Mitochondrial DNA Depletion; Mitochondrial Encephalopathy; Mitochondrial Myopathy; Myoneurogastointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrongenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion related retinal injury; oxygen poisoning; a haemoglobionopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multisystem atrophy; Adrenoleukodystrophy; and Adrenomyeloneuropathy. In some embodiments, including any of the foregoing embodiments, the oxidative stress disorder is a mitochondrial disorder. In some embodiments, including any of the foregoing embodiments, the oxidative stress disorder is an inherited mitochondrial disease. In some embodiments, including any of the foregoing embodiments, the oxidative stress disorder is Friedreich's Ataxia (FA). In some embodiments, including any of the foregoing embodiments, the oxidative stress disorder is Kearns-Sayre Syndrome (KSS). In some embodiments, including any of the foregoing embodiments, the oxidative stress disorder is Leigh Syndrome, or Leigh-like Syndrome. In some embodiments, including any of the foregoing embodiments, the oxidative stress disorder is Leber's Hereditary Optic Neuropathy (LHON). In some embodiments, including any of the foregoing embodiments, the oxidative stress disorder is Mitochondrial Myopathy, Encephalopathy, Lactacidosis, Stroke (MELAS). In some embodiments, including any of the foregoing embodiments, the oxidative stress disorder is Myoclonic Epilepsy with Ragged Red Fibers (MERRF). In some embodiments, including any of the foregoing, the oxidative stress disorder is Parkinson's disease. In some embodiments, including any of the foregoing embodiments, the oxidative stress disorder is Alzheimer's disease. In some embodiments, including any of the foregoing embodiments, the oxidative stress disorder is amyotrophic lateral sclerosis (ALS). In some embodiments, including any of the foregoing embodiments, the oxidative stress disorder is epilepsy. In some embodiments, including any of the foregoing embodiments, the oxidative stress disorder is macular degeneration. In some embodiments, including any of the foregoing embodiments, the oxidative stress disorder is brain cancer. In some embodiments, including any of the foregoing embodiments, the oxidative stress disorder is Huntington's Disease. In some embodiments, including any of the foregoing embodiments, the oxidative stress disorder is autistic disorder. In some embodiments, including any of the foregoing embodiments, the oxidative stress disorder is Rett's disorder. In some embodiments, including any of the foregoing embodiments, the oxidative stress disorder is stroke. In some embodiments, including any of the foregoing embodiments, the oxidative stress disorder is Maternally inherited diabetes and deafness (MIDD). In some embodiments, including any of the foregoing embodiments, the oxidative stress disorder is chronic fatigue. In some embodiments, including any of the foregoing embodiments, the oxidative stress disorder is contrast-induced kidney damage. In some embodiments, including any of the foregoing embodiments, the oxidative stress disorder is contrast-induced retinopathy damage. In some embodiments, including any of the foregoing embodiments, the oxidative stress disorder is cobalamin c defect. In some embodiments, including any of the foregoing embodiments, the oxidative stress disorder is not an age-associated disease. In some embodiments, including any of the foregoing embodiments, the oxidative stress disorder is not a cerebrovascular accident, stroke, or ischemia. In some embodiments, including any of the foregoing embodiments, the oxidative stress disorder is not a cerebrovascular accident or stroke. In some embodiments, including any of the foregoing embodiments, the oxidative stress disorder is not ischemia. In some embodiments, including any of the foregoing embodiments, the method is for treating the oxidative stress disorder. In some embodiments, including any of the foregoing embodiments, the method is for suppressing the oxidative stress disorder. In some embodiments, the method is a method for modulating one or more energy biomarkers, normalizing one or more energy biomarkers, or enhancing one or more energy biomarkers, wherein the one or more energy biomarkers are selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) levels; NADPH (NADPH+H+) levels; NAD levels; NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, b-hydroxy butyrate levels, acetoacetate/b-hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold. In some embodiments, including any of the foregoing embodiments, the levels are modulated to a value within about 2 standard deviations of the value in a healthy subject. In some embodiments, including any of the foregoing embodiments, the levels are modulated to a value within about 1 standard deviation of the value in a healthy subject. In some embodiments, including any of the foregoing embodiments, the levels in a subject are changed by at least about 10% above or below the level in the subject prior to modulation. In some embodiments, including any of the foregoing embodiments, the levels are changed by at least about 20% above or below the level in the subject prior to modulation. In some embodiments, including any of the foregoing embodiments, the levels are changed by at least about 30% above or below the level in the subject prior to modulation. In some embodiments, including any of the foregoing embodiments, the levels are changed by at least about 40% above or below the level in the subject prior to modulation. In some embodiments, including any of the foregoing embodiments, the levels are changed by at least about 50% above or below the level in the subject prior to modulation. In some embodiments, including any of the foregoing embodiments, the levels are changed by at least about 75% above or below the level in the subject prior to modulation. In some embodiments, including any of the foregoing embodiments, the levels are changed by at least about 100% above or at least about 90% below the level in the subject prior to modulation. In some embodiments, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; subjects requiring organ visualization via contrast solution; or other subjects with acute, chronic, or ongoing energy demands who can benefit from enhancement of energy biomarkers.

In another aspect is a method of treating or prophylactically protecting against radiation exposure, comprising administering to a subject in need thereof a therapeutically or prophylactically effective amount of a compound or composition as described herein (including but not limited to a compound described herein). In some embodiments, the method of treating or prophylactically protecting against radiation exposure comprises administering to a subject in need thereof a therapeutically or prophylactically effective of a compound of the formula I:

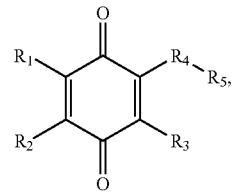

(I)

or the hydroquinone form thereof, wherein: $R_1$ and $R_2$ are independently $C_1$-$C_{10}$ alkyl; $R_3$ is $C_1$-$C_6$ alkyl; $R_4$ is $C_6$-$C_{12}$ alkyl and $R_5$ is —$CF_3$, wherein $R_5$ is attached to $R_4$ at any chemically possible location on the $C_6$-$C_{12}$ alkyl group; or $R_4$ is $C_1$-$C_{12}$ n-alkyl and $R_5$ is —$OCH_3$, —$OCF_3$, or —$OCH_2CF_3$, wherein $R_5$ is attached to $R_4$ at any chemically possible location on the $C_1$-$C_{12}$ n-alkyl group; or a pharmaceutically acceptable salt, a stereoisomer, or mixture of stereoisomers thereof. In some embodiments, the method of treating or prophylactically protecting against radiation exposure comprises administering to a subject in need thereof a therapeutically or prophylactically effective of a compound of the formula II:

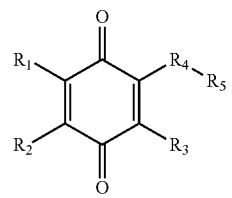

(II)

or the hydroquinone form thereof; wherein: $R_1$ and $R_2$ are independently $C_1$-$C_{10}$ alkyl; $R_3$ is $C_1$-$C_6$ alkyl or —NHS(O)$_2$CH$_3$; $R_4$ is $C_8$-$C_{12}$ alkyl and $R_5$ is $C_1$ haloalkyl, —O—$C_2$-$C_6$ alkyl, —O—$C_3$-$C_6$ haloalkyl, —O-phenyl, —O-heteroaryl, or —NR$_6$R$_7$, wherein $R_5$ is attached to $R_4$ at any chemically possible location on the $C_8$-$C_{12}$ alkyl group; or $R_4$ is $C_8$-$C_{12}$ n-alkyl and $R_5$ is $C_1$ haloalkyl, —O—$C_1$-$C_6$ alkyl, —O—$C_1$-$C_6$ haloalkyl, —O-phenyl, —O-heteroaryl, or —NR$_6$R$_7$, wherein $R_5$ is attached to $R_4$ at any chemically possible location on the $C_8$-$C_{12}$ n-alkyl group; $R_6$ and $R_7$ are independently selected from the group consisting of H and $C_1$-$C_6$ alkyl; or $R_6$ and $R_7$ together with the nitrogen atom to which they are attached form a 3-7 membered saturated heterocyclic ring; and phenyl and heteroaryl are optionally independently substituted with 1-4 alkyl substituents; or a pharmaceutically acceptable salt, a stereoisomer, or mixture of stereoisomers thereof; wherein: when $R_4$ is $C_8$ n-alkyl, then $R_5$ is not $CF_3$; and when $R_4$ is $C_{10}$ n-alkyl, then $R_5$ is not O—$CH_3$ or O—$CH_2$—$CF_3$. In some embodiments, including any of the foregoing embodiments, the method is for treating radiation exposure. In some embodiments directed to a method of treating radiation exposure, the method comprises administering the compound after exposure to radiation. In some embodiments directed to a method of treating radiation exposure, the method comprises administering the compound during exposure to radiation. In some embodiments, including any of the foregoing embodiments, the method is for prophylactically protecting against radiation exposure. In some embodiments, the method is a method of prophylactically protecting against radiation exposure, wherein the compound is administered prior to exposure to radiation. In some embodiments, including any of the foregoing embodiments, the compound is not a salt. In some embodiments, including any of the foregoing embodiments, the compound is a pharmaceutically acceptable salt. The method can use any individual compound as described herein, or a combination of compounds. In some embodiments, including any of the foregoing embodiments, the compound is administered as a pharmaceutical composition comprising the compound and a pharmaceutically acceptable carrier. In some embodiments, including any of the foregoing embodiments, the pharmaceutical composition comprises an active agent consisting essentially of the compound, and a pharmaceutically acceptable carrier. In some embodiments, including any of the foregoing embodiments, the compound is administered orally. In some embodiments, including any of the foregoing embodiments, the compound is administered by injection. In some embodiments, including any of the foregoing embodiments, the compound is administered topically. In some embodiments, including any of the foregoing embodiments, the radiation is selected from the group consisting of radiation exposure from diagnostic X-rays, dental X-rays, radiotherapy for cancer treatment, CT scans (CAT scans), fluoroscopy, mammograms, radionuclide scans, radiation from ingestion of contaminated food or water, radiation from inhalation of contaminated air or gases, and uncontrolled exposure to ionizing radiation from nuclear weapons, radioactive spills and/or cosmic radiation. In some embodiments, including any of the foregoing embodiments, the radiation is ultraviolet radiation, X-rays, gamma rays, alpha radiation, or beta radiation. In some embodiments, including any of the foregoing embodiments, the radiation is ultraviolet radiation. In some embodiments, including any of the foregoing embodiments, the radiation is X-rays. In some embodiments, including any of the foregoing embodiments, the radiation is gamma rays. In some embodiments, including any of the foregoing embodiments, the radiation is alpha radiation. In some embodiments, including any of the foregoing embodiments, the radiation is beta radiation. In some embodiments, including any of the foregoing embodiments, the subject is selected from the group consisting of: a patient undergoing diagnostic radiation exposure, a patient undergoing therapeutic radiation treatment, a patient undergoing radiography, a patient undergoing fluoroscopy, a patient receiving a dental X-ray, a patient undergoing a CT scan, a person who routinely works at high elevation, an aircraft flight crew member, a person who spends a prolonged period at high elevation, a mountain climber, a person who travels into outer space, an astronaut, a space tourist, a person who works at a site contaminated with radioactive waste, a person who works at a waste site containing a high amount of radioactivity, a person who works at a site contaminated with coal ash, and a miner who works in a site with elevated radioactivity. In some embodiments, including any of the foregoing embodiments, the subject is selected from the group consisting of: a person who routinely works with or near radiation or radioactive materials, an X-ray technician, a nuclear medicine specialist, a nuclear power plant worker, and a person who lives near a nuclear power plant. In some embodiments, uses of the methods disclosed herein include, but are not limited to: reducing the effect of ionizing radiation on normal cells in a subject exposed to or at risk of incurring exposure to ionizing radiation; reducing the effect of radiation in a subject exposed to an accidental or intentional release of radioactive materials; preventing death of radiation-damaged or radiation-injured non-cancerous cells; and improved radiotherapy methods for treatment of cancer, comprising administering to the subject a therapeutically or prophylactically effective amount of the compound in conjunction with an effective amount of radiation, such that radiation injury to normal cells is decreased or eliminated.

In another aspect is the use of a compound as described herein, including but not limited to any of the foregoing embodiments, for treating or suppressing an oxidative stress disorder. In another aspect is the use of a compound as described herein, including but not limited to any of the foregoing embodiments, in the manufacture of a medicament for use in treating or suppressing an oxidative stress disorder.

In another aspect is the use of a compound as described herein, including but not limited to any of the foregoing embodiments, for treating or prophylactically protecting against radiation exposure. In another aspect is the use of a compound as described herein, including but not limited to any of the foregoing embodiments, in the manufacture of a medicament for use in treating or prophylactically protecting against radiation exposure.

For all the compounds, compositions, formulations and methods described herein, any compound in the quinone form can also be used in its reduced form (hydroquinone) when desired. That is, the compounds recited herein as cyclohexadienedione compounds (oxidized quinone) form can also be used in their benzenediol (reduced hydroquinone) form as desired.

It is to be understood that the description of compounds, compositions, formulations, and methods of treatment described herein include "comprising", "consisting of", and "consisting essentially of" embodiments. In some embodiments, for all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

DETAILED DESCRIPTION

Provided herein are compounds useful in treating or suppressing diseases, developmental delays and symptoms related to oxidative stress such as mitochondrial disorders, impaired energy processing disorders, neurodegenerative diseases and diseases of aging, and methods of using such compounds for treating or suppressing an oxidative stress disorder, or for modulating, normalizing, or enhancing one or more (e.g. one, two, three, or more) energy biomarkers. Further provided herein are compounds and compositions for use in prophylactically protecting against and/or for treating radiation exposure, and methods of using such compounds and compositions for prophylactically protecting against and/or for treating radiation exposure.

The abbreviations used herein have their conventional meaning within the chemical and biological arts, unless otherwise specified.

Reference to "about" a value or parameter herein includes (and describes) variations that are directed to that value or parameter per se. For example, description referring to "about X" includes description of "X".

As used herein, and unless otherwise specified, the terms "about" and "approximately," when used in connection with temperatures, doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

The terms "a" or "an," as used in herein means one or more, unless context clearly dictates otherwise.

By "subject," "individual," or "patient" is meant an individual organism, preferably a vertebrate, more preferably a mammal, most preferably a human.

"Treating" a disorder with the compounds and methods discussed herein is defined as administering one or more of the compounds discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the compounds and methods discussed herein is defined as administering one or more of the compounds discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. In some embodiments, genetic screening can be used to identify patients at risk of the disorder. The compounds and methods disclosed herein can then be administered to asymptomatic patients at risk of developing the clinical symptoms of the disorder, in order to suppress the appearance of any adverse symptoms.

"Therapeutic use" of the compounds discussed herein is defined as using one or more of the compounds discussed herein to treat or suppress a disorder, as defined herein. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. In some embodiments, in a situation where significant energy demands are placed on a subject, it may be desirable to increase the level of ATP in that subject to a level above the normal level of ATP in that subject. Enhancement can also be of beneficial effect in a subject suffering from a disease or pathology such as e.g. a mitochondrial disorder, in that normalizing an energy biomarker may not achieve the optimum outcome for the subject; in such cases, enhancement of one or more energy biomarkers can be beneficial, in some embodiments, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. In some embodiments, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

By "radiation," as used herein, is meant radiation, including ionizing radiation, capable of causing molecular or cellular damage. In some embodiments, such forms of radiation include ultraviolet radiation, alpha radiation, beta radiation, x-rays, and gamma rays. In some embodiments, sources of radiation include radioactive isotopes, which may be naturally-occurring or man-made, and cosmic rays.

Radiation can be emitted due to the gradual decay of radioactive isotopes, or due to nuclear fission or fusion events (as in an atomic bomb or nuclear reactor). In some embodiments, the radiation is x-ray radiation. In some embodiments, the radiation is gamma radiation. In some embodiments, the radiation is beta radiation. In some embodiments, the radiation is alpha radiation. In some embodiments, the radiation is ultraviolet radiation. In some embodiments, the radiation is radiation due to radiation therapy. In some embodiments, the radiation is due to sun exposure. In some embodiments, the radiation is radiation due to radioactive fallout or contamination.

In the context of radiation, "treating" radiation exposure (or radiation damage or radiation injury) with the compounds, compositions, and methods discussed herein is defined as administering one or more of the compounds or compositions discussed herein, with or without additional therapeutic agents, in order to reduce or eliminate either the deleterious effects of radiation exposure or one or more symptoms of radiation exposure, or to retard the progression of the deleterious effects of radiation exposure or of one or more symptoms of radiation exposure, or to reduce the severity of the deleterious effects of radiation exposure or of one or more symptoms of radiation exposure, or to suppress the clinical manifestation of radiation exposure, or to suppress the manifestation of one or more adverse symptoms of radiation exposure. In some embodiments, treatment of radiation exposure (or radiation damage or injury) in a subject (or cell or tissue) involves decreasing damage to one or more nucleic acid molecules in a subject (or cell or tissue) which has received one or more compounds or compositions disclosed herein by at least about 10%, 20%, 30%, 40%, 50%, 80%, 90%, or 95%, compared to a subject (or cell or tissue) which has not received one or more compounds or compositions disclosed herein.

In the context of radiation, "therapeutic use" of the compounds discussed herein is defined as using one or more of the compounds or compositions discussed herein to treat radiation exposure (or radiation damage or injury).

In the context of radiation, a "therapeutically effective amount" of a compound is an amount of the compound, which, when administered to a subject, is sufficient to reduce or eliminate either the deleterious effects of radiation exposure or one or more symptoms of radiation exposure, or to retard the progression of the deleterious effects of radiation exposure or of one or more symptoms of radiation exposure, or to reduce the severity of the deleterious effects of radiation exposure or of one or more symptoms of radiation exposure, or to suppress the clinical manifestation of radiation exposure, or to suppress the manifestation of one or more adverse symptoms of radiation exposure. A therapeutically effective amount can be given in one or more administrations.

In the context of radiation, "prophylactically protecting a subject (or a cell or tissue) against radiation exposure (or radiation damage or injury)" with the compounds, compositions, and methods discussed herein is defined as administering one or more of the compounds or compositions discussed herein, with or without additional therapeutic agents, prior to exposure to radiation, in order to reduce or eliminate either the deleterious effects of radiation exposure or one or more symptoms of radiation exposure, or to retard the progression of the deleterious effects of radiation exposure or of one or more symptoms of radiation exposure, or to reduce the severity of the deleterious effects of radiation exposure or of one or more symptoms of radiation exposure, or to suppress the clinical manifestation of radiation exposure, or to suppress the manifestation of one or more adverse symptoms of radiation exposure. In some embodiments, prophylactic use of the compounds, compositions, and methods disclosed herein would include, in some embodiments, administering one or more of the compounds or compositions described herein to a patient undergoing radiotherapy at risk of radiation damage or injury, where the compound(s) or composition(s) are administered prior to radiotherapy, or to a worker in the nuclear industry at risk of exposure to radiation prior to the arrival of the worker at a site where they could be exposed to excessive radiation. In some embodiments, prophylactic protection against radiation exposure (or damage or injury) in a subject (or cell or tissue) involves decreasing damage to one or more nucleic acid molecules in a subject (or cell or tissue) which has received one or more compounds or compositions disclosed herein prior to radiation exposure by at least about 10%, 20%, 30%, 40%, 50%, 80%, 90%, or 95%, compared to a subject (or cell or tissue) which has not received one or more compounds or compositions disclosed herein prior to radiation exposure.

In the context of radiation, "prophylactic use" of the compounds or compositions discussed herein is defined as using one or more of the compounds or compositions discussed herein to prophylactically protect against radiation exposure (or damage or injury).

In the context of radiation, a "prophylactically effective amount" of a compound is an amount of the compound, which, when administered to a subject prior to radiation exposure, is sufficient to reduce or eliminate either the deleterious effects of radiation exposure or one or more symptoms of radiation exposure, or to retard the progression of the deleterious effects of radiation exposure or of one or more symptoms of radiation exposure, or to reduce the severity of the deleterious effects of radiation exposure or of one or more symptoms of radiation exposure, or to suppress the clinical manifestation of radiation exposure, or to suppress the manifestation of one or more adverse symptoms of radiation exposure. A prophylactically effective amount can be given in one or more administrations.

In the context of radiation, a subject in "potential need" of a compound or composition disclosed herein, or a method disclosed herein, is a subject who may be exposed to excessive radiation, in some embodiments, who has about a 0.001% chance, about a 0.01% chance, about a 0.1% chance, about a 1% chance, about a 5% chance, about a 10% chance, about a 25% chance, or about a 50% chance of being exposed to excessive radiation, or at least about a 0.001% chance, at least about a 0.01% chance, at least about a 0.1% chance, at least about a 1% chance, at least about a 5% chance, at least about a 10% chance, at least about a 25% chance, or at least about a 50% chance of being exposed to excessive radiation. In some embodiments, excessive radiation can be more than about 1 mSv in one year, more than about 2 mSv in one year, more than about 5 mSv in one year, more than about 10 mSv in one year, more than about 20 mSv in one year, or more than about 50 mSv in one year. In some embodiments, excessive radiation can be more than about 1 mGray in one year, more than about 2 mGray in one year, more than about 5 mGray in one year, more than about 10 mGray in one year, more than about 20 mGray in one year, or more than about 50 mGray in one year. A subject in need or potential need of a compound or composition disclosed herein, or a method disclosed herein, can also be a subject who desires protection against exposure to routine radiation, such as natural background radiation (e.g. ultraviolet light), in order to minimize the effects of routine or background exposure to radiation.

While the compounds described herein can occur and can be used as the neutral (non-salt) compound, the description is intended to embrace all salts of the compounds described herein, as well as methods of using such salts of the compounds. In some embodiments, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. In some embodiments, inorganic acids include, but are not limited to, hydrochloric acid, hydrobromic acid, sulfuric acid, nitric acid, and phosphoric acid. In some embodiments, organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. In some embodiments, inorganic salts of acid compounds include, but are not limited to, alkali metal and alkaline earth salts, such as sodium salts, potassium salts, magnesium salts, and calcium salts; ammonium salts; and aluminum salts. In some embodiments, organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

Included herein, if chemically possible, are all stereoisomers of the compounds, including diastereomers and enantiomers. Also included are mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The description of compounds herein also includes all isotopologues, in some embodiments, partially deuterated or perdeuterated analogs of all compounds herein.

"Hydroquinone form" indicates the form of the compound when a two electron reduction of the quinone ring is effected, providing a net conversion of the two oxo groups to two hydroxy groups. For example, the hydroquinone form of the compounds described herein indicates:

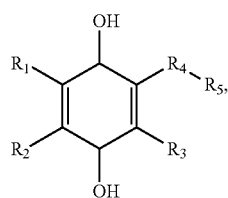

(II)

wherein $R_1$, $R_2$, $R_3$, $R_4$, and $R_5$ are defined herein.

The term "alkyl" is intended to embrace a saturated linear, branched, or cyclic hydrocarbon, or any combination thereof. The point of attachment of the alkyl group to the remainder of the molecule can be at any chemically possible location on the alkyl group. In some embodiments, an alkyl has from 1 to 12 carbon atoms ("$C_1$-$C_{12}$ alkyl"), from 6 to 12 carbon atoms ("$C_6$-$C_{12}$ alkyl"), from 1 to 10 carbon atoms ("$C_1$-$C_{10}$ alkyl"), from 1 to 8 carbon atoms ("$C_1$-$C_8$ alkyl"), from 1 to 6 carbon atoms ("$C_1$-$C_6$ alkyl"), from 1 to 4 carbon atoms ("$C_1$-$C_4$ alkyl"), from 1 to 3 carbon atoms ("$C_1$-$C_3$ alkyl"), or from 1 to 2 carbon atoms ("$C_1$-$C_2$ alkyl"). In some embodiments, non-limiting examples of "$C_1$-$C_6$ alkyl" include methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, cyclopentyl, hexyl, and cyclohexyl. "Cycloalkyl" is a cyclic alkyl group as defined herein.

As used herein, "haloalkyl" refers to alkyl, as defined above, wherein the alkyl includes at least one substituent selected from a halogen, e.g., F, Cl, Br, or I. In some examples haloalkyl includes, but is not limited to, —$CF_3$, —$CHF_2$, —$CH_2F$, —$CH_2$—$CF_3$, —$CH_2$—$CHF_2$, or —$CH_2$—$CH_2F$ When haloalkyl is a $C_1$ haloalkyl, then the $C_1$ haloalkyl is selected from —$CX_3$, —$CHX_2$, and —$CH_2X$, wherein X is independently in each instance selected from F, Cl, Br, and I.

As used herein, "heterocyclic ring," refers to a cycloalkyl in which one or more carbon atoms are replaced by at least one nitrogen atom up to two additional heteroatoms independently selected from N, O, and S. Examples of heterocyclic ring include, but are not limited to, morpholinyl, piperidinyl, piperazinyl and pyrrolidinyl.

As used herein, "heteroaryl" refers to a monovalent moiety that is a radical of an aromatic compound wherein the ring atoms contain carbon atoms and at least one oxygen, sulfur, or nitrogen atom. Examples of heteroaryl moieties include, but are not limited to those having 5 to 12 ring atoms. When more than one ring is present, the rings are fused.

By "respiratory chain disorder" is meant a disorder which results in the decreased utilization of oxygen by a mitochondrion, cell, tissue, or individual, due to a defect or disorder in a protein or other component contained in the mitochondrial respiratory chain. By "protein or other component contained in the mitochondrial respiratory chain" is meant the components (including, but not limited to, proteins, tetrapyrroles, and cytochromes) comprising mitochondrial complex I, II, III, IV, and/or V. "Respiratory chain protein" refers to the protein components of those complexes, and "respiratory chain protein disorder" is meant a disorder which results in the decreased utilization of oxygen by a mitochondrion, cell, tissue, or individual, due to a defect or disorder in a protein contained in the mitochondrial respiratory chain.

The terms "Parkinson's," (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "Friedreich's ataxia" is intended to embrace other related ataxias, and is also sometimes referred to as hereditary ataxia, familial ataxia, or Friedreich's tabes.

The term "ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; sensory ataxia; and vestibular ataxia. In some embodiments, the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplastic cerebellar atrophy associated with malignant tumor, toxic cerebellar atrophy caused by toxic substances, Vitamin E deficiency due to mutation of a Tocopherol transfer protein (aTTP) or lipid absorption disorder such as Abetalipoproteinemia, cerebellar atrophy associated with endocrine disturbance and the like.

In some embodiments, ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptoms (postural adjustment dysfunction, muscular rigidity, akinesia, tremors), dysphagia, lingual atrophy, posterior funiculus symptom, muscle atrophy, muscle weakness, deep hyperreflexia, sensory disturbance, scoliosis, kyphoscoliosis, foot deformities, anarthria, dementia, manic state, decreased motivation for rehabilitation and the like.

As used herein, "optionally substituted," when used to describe a radical moiety, e.g., phenyl and heteroaryl are optionally independently substituted with 1-4 substituents selected from the group consisting of alkyl, means that such moiety is optionally bonded to one, two, three, or four alkyl substituents. In certain embodiments, when a radical moiety is optionally substituted with an optional substituent(s), the optional substituent(s) is not further substituted, unless otherwise specified.

Diseases Amenable to Treatment or Suppression with Compounds and Methods Disclosed Herein A variety of disorders/diseases are believed to be caused or aggravated by oxidative stress affecting normal electron flow in the cells, such as mitochondrial disorders, impaired energy processing disorders, neurodegenerative diseases and diseases of aging, and can be treated or suppressed using the compounds and methods disclosed herein.

In some embodiments, including the foregoing embodiment, oxidative stress disorders include, in some embodiments, mitochondrial disorders (including inherited mitochondrial diseases) such as Alpers Disease, Barth syndrome, Beta-oxidation Defects, Carnitine-Acyl-Carnitine Deficiency, Carnitine Deficiency, Creatine Deficiency Syndromes, Co-Enzyme Q10 Deficiency, Complex I Deficiency, Complex II Deficiency, Complex III Deficiency, Complex IV Deficiency, Complex V Deficiency, COX Deficiency, chronic progressive external ophthalmoplegia (CPEO), CPT I Deficiency, CPT II Deficiency, Friedreich's Ataxia (FA), Glutaric Aciduria Type II, Kearns-Sayre Syndrome (KSS), Lactic Acidosis, Long-Chain Acyl-CoA Dehydrongenase Deficiency (LCAD), LCHAD, Leigh Syndrome, Leigh-like Syndrome, Leber's Hereditary Optic Neuropathy (LHON, also referred to as Leber's Disease, Leber's Optic Atrophy (LOA), or Leber's Optic Neuropathy (LON)), Lethal Infantile Cardiomyopathy (LIC), Luft Disease, Multiple Acyl-CoA Dehydrogenase Deficiency (MAD), Medium-Chain Acyl-CoA Dehydrongenase Deficiency (MCAD), Mitochondrial Myopathy, Encephalopathy, Lactacidosis, Stroke (MELAS), Myoclonic Epilepsy with Ragged Red Fibers (MERRF), Mitochondrial Recessive Ataxia Syndrome (MIRAS), Mitochondrial Cytopathy, Mitochondrial DNA Depletion, Mitochondrial Encephalopathy, Mitochondrial Myopathy, Myoneurogastointestinal Disorder and Encephalopathy (MNGIE), Neuropathy, Ataxia, and Retinitis Pigmentosa (NARP), Pearson Syndrome, Pyruvate Carboxylase Deficiency, Pyruvate Dehydrogenase Deficiency, POLG Mutations, Respiratory Chain Disorder, Short-Chain Acyl-CoA Dehydrogenase Deficiency (SCAD), SCHAD, Very Long-Chain Acyl-CoA Dehydrongenase Deficiency (VLCAD); myopathies such as cardiomyopathy and encephalomyopathy; neurodegenerative diseases such as Parkinson's disease, Alzheimer's disease, and amyotrophic lateral sclerosis (ALS, also known as Lou Gehrig's disease); motor neuron diseases; neurological diseases such as epilepsy; age-associated diseases, particularly diseases for which CoQ10 has been proposed for treatment, such as macular degeneration, diabetes (e.g. Type 2 diabetes mellitus), metabolic syndrome, and cancer (e.g. brain cancer); genetic diseases such as Huntington's Disease (which is also a neurological disease); mood disorders such as schizophrenia and bipolar disorder; pervasive developmental disorders such as autistic disorder, Asperger's syndrome, childhood disintegrative disorder (CDD), Rett's disorder, and PDD-not otherwise specified (PDD-NOS); cerebrovascular accidents such as stroke; vision impairments such as those caused by neurodegenerative diseases of the eye such as optic neuropathy, Leber's hereditary optic neuropathy, dominant inherited juvenile optic atrophy, optic neuropathy caused by toxic agents, glaucoma, age-related macular degeneration (both "dry" or non-exudative macular degeneration and "wet" or exudative macular degeneration), Stargardt's macular dystrophy, diabetic retinopathy, diabetic maculopathy, retinopathy of prematurity, or ischemic reperfusion-related retinal injury; disorders caused by energy impairment include diseases due to deprivation, poisoning or toxicity of oxygen, and qualitative or quantitative disruption in the transport of oxygen such as haemoglobinopathies, in some embodiments, thalassemia or sickle cell anemia; other diseases in which mitochondrial dysfunction is implicated such as excitoxic, neuronal injury, such as that associated with seizures, stroke and ischemia; and other disorders including renal tubular acidosis; attention deficit/hyperactivity disorder (ADHD); neurodegenerative disorders resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; muscular dystrophies; leukodystrophies; Progressive Supranuclear Palsy; spinal muscular atrophy; hearing loss (e.g. noise induced hearing loss); traumatic brain injury; Juvenile Huntington's Disease; Multiple Sclerosis; NGLY1; Multisystem atrophy; Adrenoleukodystrophy; and Adrenomyeloneuropathy. It is to be understood that certain specific diseases or disorders may fall within more than one category; in some embodiments, Huntington's Disease is a genetic disease as well as a neurological disease. Furthermore, certain oxidative stress diseases and disorders may also be considered mitochondrial disorders.

For some disorders amenable to treatment with compounds and methods disclosed herein, the primary cause of the disorder is due to a defect in the respiratory chain or another defect preventing normal utilization of energy in mitochondria, cells, or tissue(s). In some embodiments, disorders falling in this category include inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Syndrome, Leigh-like Syndrome, Kearns-Sayre Syndrome (KSS), and Friedreich's Ataxia (FA). For some disorders amenable to treatment with compounds and methods disclosed herein, the primary cause of the disorder is not due to respiratory chain defects or other defects preventing normal utilization of energy in mitochondria, cells, or tissue(s); in some embodiments, disorders falling in this category include stroke, cancer, and diabetes. However, these latter disorders are particularly aggravated by energy impairments, and are particularly amenable to treatment with compounds disclosed herein in order to ameliorate the condition. In some embodiments, such disorders include ischemic stroke and hemorrhagic stroke, where the primary cause of the disorder is due to impaired blood supply to the brain. While an ischemic episode caused by a thrombosis or embolism, or a hemorrhagic episode caused by a ruptured blood vessel, is not primarily caused by a defect in the respiratory chain or another metabolic defect preventing normal utilization of energy, oxidative stress plays a role in the ischemic cascade due to oxygen reperfusion injury following hypoxia (this cascade occurs in heart attacks as well as in strokes). Accordingly, treatment with compounds and methods disclosed herein will mitigate the effects of the disease, disorder or condition. Modulating one or more energy biomarkers, normalizing one or more energy biomarkers, or enhancing one or more energy biomarkers can also prove beneficial in such disorders both as a therapeutic measure and a prophylactic measure. In some embodiments, for a patient scheduled to undergo non-emergency repair of an aneurysm, enhancing energy biomarkers before and during the pre-operative can improve the patient's prognosis should the aneurysm rupture before successful repair.

The term "oxidative stress disorder" or "oxidative stress disease" encompass both diseases caused by oxidative stress and diseases aggravated by oxidative stress. The terms "oxidative stress disorder" or "oxidative stress disease" encompass both diseases and disorders where the primary cause of the disease is due to a defect in the respiratory chain or another defect preventing normal utilization of energy in mitochondria, cells, or tissue(s), and also diseases and disorders where the primary cause of the disease is not due to a defect in the respiratory chain or another defect preventing normal utilization of energy in mitochondria, cells, or tissue(s). The former set of diseases can be referred to as "primary oxidative stress disorders," while the latter can be referred to as "secondary oxidative stress disorders." It should be noted that the distinction between "diseases caused by oxidative stress" and "diseases aggravated by oxidative stress" is not absolute; a disease may be both a disease caused by oxidative stress and a disease aggravated by oxidative stress. The boundary between "primary oxidative stress disorder" and a "secondary oxidative stress disorder" is more distinct, provided that there is only one primary cause of a disease or disorder and that primary cause is known.

Bearing in mind the somewhat fluid boundary between diseases caused by oxidative stress and diseases aggravated by oxidative stress, mitochondrial diseases or disorders and impaired energy processing diseases and disorders tend to fall into the category of diseases caused by oxidative stress, while neurodegenerative disorders and diseases of aging tend to fall into the category of diseases aggravated by oxidative stress. Mitochondrial diseases or disorders and impaired energy processing diseases and disorders are generally primary oxidative stress disorders, while neurodegenerative disorders and diseases of aging may be primary or secondary oxidative stress disorders.

Clinical Assessment of Oxidative Stress and Efficacy of Therapy

Several readily measurable clinical markers are used to assess the metabolic state of patients with oxidative stress disorders. These markers can also be used as indicators of the efficacy of a given therapy, as the level of a marker is moved from the pathological value to the healthy value. These clinical markers include, but are not limited to, energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) or NADPH (NADPH+H+) levels; NAD or NADP levels; ATP levels; anaerobic threshold; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment, the level of one or more energy biomarkers in a patient suffering from an oxidative stress disorder, such as Friedreich's ataxia, Leber's hereditary optic neuropathy, MELAS, KSS or CoQ10 deficiency, is improved to within two standard deviations of the average level in a healthy subject. In another embodiment, the level of one or more of these energy biomarkers in a patient suffering from an oxidative stress disorder, such as Friedreich's ataxia, Leber's hereditary optic neuropathy, MELAS, KSS or CoQ10 deficiency is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods disclosed herein. Lactate, a product of the anaerobic metabolism of glucose, is removed by reduction to pyruvate in an aerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate:AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H+, NADPH+ H+, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H+) or NADPH (NADPH+H+) can be measured by a variety of fluorescent, enzymatic, or electrochemical techniques, e.g., the electrochemical assay described in US 2005/0067303.

GSH, GSSG, Cys, and CySS levels: Briefly, plasma levels of GSH, GSSG, Cys, and CySS are used to calculate the in vivo $E_h$ values. Samples are collected using the procedure of Jones et al (2009 Free Radical Biology & Medicine 47(10) pp. 1329-1338), and bromobimane is used to alkylate free thiols and HPLC and either electrochemical or MSMS to separate, detect, and quantify the molecules. As described in more detail in U.S. Provisional Patent Application No. 61/698,431 filed Sep. 7, 2012, and U.S. Provisional Patent Application No. 61/792,797 filed Mar. 15, 2013, we have developed a method for different experimental parameters to analyze the most common monothiols and disulfide (cystine, cysteine, reduced (GSH) and oxidized glutathione (GSSG)) present in human plasma, and using Bathophenanthroline disulfonic acid as the internal standard (IS). Complete separation of all the targets analytes and IS at 35.0 on a C18 RP column (250 mm×4.6 mm, 3 micron) was achieved using 0.2% TFA:Acetonitrile as a mobile phase pumped at the rate of 0.6 ml min-1 using electrochemical detector in DC mode at the detector potential of 1475 mV.

Oxygen consumption (vO2 or VO2), carbon dioxide output (vCO2 or VCO2), and respiratory quotient (VCO2/VO2): vO2 is usually measured either while resting (resting vO2) or at maximal exercise intensity (vO2 max). Optimally, both values will be measured. However, for severely disabled patients, measurement of vO2 max may be impractical. Measurement of both forms of vO2 is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C:Cytochrome C parameters, such as oxidized cytochrome C levels (Cyt Cox), reduced cytochrome C levels (Cyt Cred), and the ratio of oxidized cytochrome C/reduced cytochrome C ratio (Cyt Cox)/(Cyt Cred), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Pira et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods disclosed herein can result in about a 10% or greater improvement in exercise tolerance (in some embodiments, about a 10% or greater increase in time to exhaustion, in some embodiments, from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes disclosed herein, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q (CoQred) levels, oxidized coenzyme Q (CoQox) levels, total coenzyme Q (CoQtot) levels, oxidized cytochrome C levels, reduced cytochrome C levels, oxidized cytochrome C/reduced cytochrome C ratio, GSH and cysteine reduced, oxidized, total levels and ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods disclosed herein. (For the purposes disclosed herein, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods disclosed herein. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
| --- | --- | --- | --- |
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ H+ gradient | Δ ATP | Organ dependent dysfunction |
| Respiratory Chain | ↓ Electron flux | Δ VO2, RQ, BMR, ΔT, AT, pH | Metabolic dyscrasia & fatigue |
| Mitochondria & cytosol | ↓ ATP, ↓ VO2 | Δ Work, ΔHR (CO) | Exercise intolerance |
| Mitochondria & cytosol | ↓ ATP | Δ PCr | Exercise intolerance |
| Respiratory Chain | ↓ Cyt COx/Red | Δ λ ~700-900 nm (Near Infrared Spectroscopy) | Exercise intolerance |
| Intermediary metabolism | ↓ Catabolism | Δ C14-Labeled substrates | Metabolic dyscrasia & fatigue |
| Respiratory Chain | ↓ Electron flux | Δ Mixed Venous VO2 | Metabolic dyscrasia & fatigue |
| Mitochondria & cytosol | ↑ Oxidative stress | Δ Tocopherol & Tocotrienols, CoQ10, docosahexaenoic acid | Uncertain |
| Mitochondria & cytosol | ↑ Oxidative stress | Δ Glutathione$_{red}$ | Uncertain |
| Mitochondria & cytosol | Nucleic acid oxidation | Δ 8-hydroxy 2-deoxy guanosine | Uncertain |
| Mitochondria & cytosol | Lipid oxidation | Δ Isoprostane(s), eicosanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by an oxidative stress disorder in accordance with the methods disclosed herein may result in the inducement of a reduction or alleviation of symptoms in the subject, e.g., to halt the further progression of the disorder.

Partial or complete suppression of the oxidative stress disorder can result in a lessening of the severity of one or more of the symptoms that the subject would otherwise experience. In some embodiments, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of oxidative stress disorders, the compounds disclosed herein can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. In some embodiments, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. In some embodiments, a person undergoing strenuous effort or prolonged vigorous physical activity, such as mountain climbing, could benefit from increased ATP levels or decreased lactate levels. As described herein, normalization of energy biomarkers may not achieve the optimum state for a subject with an oxidative stress disease, and such subjects can also benefit from enhancement of energy biomarkers. In some embodiments, subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds disclosed herein can also be used in research applications. They can be used in in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds as described herein can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds disclosed herein.

Additionally, the compounds disclosed herein can be used in biochemical tests or assays. Such tests can include incubation of one or more compounds disclosed herein with a tissue or cell sample from a subject to evaluate a subject's potential response (or the response of a specific subset of subjects) to administration of said one or more compounds, or to determine which compound disclosed herein produces the optimum effect in a specific subject or subset of subjects. One such test or assay would involve 1) obtaining a cell sample or tissue sample from a subject in which modulation of one or more energy biomarkers can be assayed; 2) administering one or more compounds disclosed herein to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds disclosed herein to the cell sample or tissue sample; 3) determining the amount of modulation of the one or more energy biomarkers after administration of the at least two compounds, compared to the status of the energy biomarker prior to administration of the at least two compounds, and 4) selecting a compound or compounds for use in treatment, suppression, or modulation based on the amount of modulation determined in step 3.

Pharmaceutical Compositions

The terms "pharmaceutical formulation" and "pharmaceutical composition" are used interchangeably herein.

The compounds described herein can be formulated as pharmaceutical compositions by formulation with additives such as pharmaceutically acceptable excipients, pharmaceutically acceptable carriers, and pharmaceutically acceptable vehicles. The terms "pharmaceutically acceptable excipients," "pharmaceutically acceptable carriers," and "pharmaceutically acceptable vehicles" are used interchangeably herein. Suitable pharmaceutically acceptable excipients, carriers and vehicles include processing agents and drug delivery modifiers and enhancers, such as, in some embodiments, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic, prophylactic, or suppressive effect or an amount effective to modulate, normalize, or enhance an energy biomarker. The unit dose may be sufficient as a single dose to have a therapeutic, prophylactic, or suppressive effect or an amount effective to modulate, normalize, or enhance an energy biomarker. Alternatively, the unit dose may be a dose administered periodically in a course of treatment, prophylaxis, or suppression of a disorder, or to modulate, normalize, or enhance an energy biomarker.

Pharmaceutical compositions containing the compounds disclosed herein may be in any form suitable for the intended method of administration, including, in some embodiments, a solution, a suspension, or an emulsion. Liquid carriers are typically used in preparing solutions, suspensions, and emulsions. Liquid carriers contemplated for use in the practice include in some embodiments, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, in some embodiments, monohydric alcohols, such as ethanol, and polyhydric alcohols, such as glycols. Suitable oils include, in some embodiments, soybean oil, coconut oil, olive oil, safflower oil, cottonseed oil, and the like. For parenteral administration, the carrier can also be an oily ester such as ethyl oleate, isopropyl myristate, and the like. Compositions disclosed herein may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, in some embodiments, a biodegradable material that can degrade spontaneously in situ and in vivo, in some embodiments, by hydrolysis or enzymatic cleavage, e.g., by proteases. The delivery system may be, in some embodiments, a naturally occurring or synthetic polymer or copolymer, in some embodiments, in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds disclosed herein may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. In some embodiments, suitable modes of administration include oral, subcutaneous, transdermal, transmucosal, iontophoretic, intravenous, intra-arterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intra-sternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically or prophylactically effective. Additional methods of administration are known in the art.

In some embodiments, especially those embodiments where a formulation is used for injection or other parenteral administration including the routes listed herein, but also including embodiments used for oral, gastric, gastrointestinal, or enteric administration, the formulations and preparations used in the methods disclosed herein are sterile. Sterile pharmaceutical compositions are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Injectable preparations, in some embodiments, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, in some embodiments, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds disclosed herein can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound disclosed herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

Also provided are articles of manufacture and kits containing materials useful for treating or suppressing oxidative stress disorders. Also provided are kits comprising any one or more of the compounds as described herein. In some embodiments, the kit disclosed herein comprises the container described herein.

In other aspects, the kits may be used for any of the methods described herein, including, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or prophylactically effective amount or effective amount for a given situation can be readily determined by routine experimentation and is within the skill and judgment of the ordinary clinician.

In some embodiments, dosages which can be used are a therapeutically effective amount or prophylactically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds disclosed herein may be administered in a single daily dose, or the total daily dosage may be administered in divided dosage of two, three or four times daily.

While the compounds disclosed herein can be administered as the sole active pharmaceutical agent, they can also be used in combination with one or more other agents used in the treatment or suppression of disorders. Representative agents useful in combination with the compounds disclosed herein for the treatment or suppression of oxidative stress disorders include, but are not limited to, Coenzyme Q, vitamin E, idebenone, MitoQ, vitamins, NAC, and antioxidant compounds.

When additional active agents are used in combination with the compounds disclosed herein, the additional active agents may generally be employed in therapeutic amounts as indicated in the Physicians' Desk Reference (PDR) 53rd Edition (1999), or such therapeutically or prophylactically useful amounts as would be known to one of ordinary skill in the art.

The compounds disclosed herein and the other therapeutically active agents can be administered at the recommended maximum clinical dosage or at lower doses. Dosage levels of the active compounds in the compositions disclosed herein may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

Sources of Radiation

The compounds, compositions, and methods disclosed herein can be used in any situation where prophylactic protection against or treatment for radiation exposure is desired, whether exposure to such radiation is known to be certain to occur (in some embodiments, a patient undergoing a CT scan) or exposure to radiation is possible (in some embodiments, a worker in a nuclear power plant). The compounds, compositions, and methods disclosed herein can be used to prophylactically protect against or to treat radiation exposure from, in some embodiments, diagnostic X-rays, dental X-rays, radiotherapy for cancer treatment, CT scans (CAT scans), fluoroscopy, mammograms, radionuclide scans, radiation from ingestion of contaminated food or water, radiation from inhalation of contaminated air or gases, and uncontrolled exposure to ionizing radiation from nuclear weapons, radioactive spills and/or cosmic radiation. The compounds, compositions, and methods disclosed herein can be used to prophylactically protect against or to treat radiation exposure from ultraviolet light, such as from prolonged exposure to sunlight, or exposure to intense sunlight.

Subjects who are exposed to radiation include, in some embodiments, patients undergoing diagnostic or therapeutic radiation exposure, such as occurs during medical or dental procedures, such as radiography, fluoroscopy, dental X-rays, and CT scans, and therapeutic radiation treatment. Subjects who are exposed to radiation also include persons who routinely work at high elevation, such as aircraft flight crew members, or who spend a prolonged period at high elevation (greater than about 1 mile or about 1.6 kilometers above sea level), such as mountain climbers, or who travel into outer space, such as astronauts and space tourists. Subjects who are exposed to radiation also include persons who must decontaminate sites which are contaminated with radioactive waste, or with waste containing a high amount of radioactivity such as coal ash, or miners who work in sites with elevated radioactivity. Subjects who are at risk of being exposed to radiation include persons who routinely work with or near radiation or radioactive materials, such as X-ray technicians, nuclear medicine specialists, nuclear power plant workers, and persons who live near a nuclear power plant.

In some embodiments disclosed herein, the compounds, compositions, and methods are used to prophylactically protect against or to treat excess radiation; that is, radiation in excess of the natural background radiation. The 2007 recommendation of the International Commission on Radiological Protection (ICRP) for exposure of the general public to radiation is a limit of 1 milliSievert (1 mSv) per year (Wrixon, A. D., J. Radiol. Prot. 28:161-168 (2008)). Thus, in some embodiments, the compounds, compositions, and methods can be used for therapeutic or prophylactic use in subjects whose expected or actual dose of radiation exceeds about 1 mSv in one year. The recommended occupational exposure from the ICRP is 20 mSv per year, averaged over five years, with no more than 50 mSv exposure in any one year, and thus, the compounds, compositions, and methods can be used for therapeutic or prophylactic use in subjects whose expected or actual dose of radiation exceeds that level. In further embodiments, the compounds, compositions, and methods can be used for therapeutic or prophylactic use in subjects whose expected or actual dose of radiation exceeds about 2 mSv in one year, about 5 mSv in one year, about 10 mSv in one year, about 20 mSv in one year, or about 50 mSv in one year. In further embodiments, the compounds, compositions, and methods can be used for therapeutic or prophylactic use in subjects whose expected or actual dose of radiation exceeds about 2 mGray in one year, about 5 mGray in one year, about 10 mGray in one year, about 20 mGray in one year, or about 50 mGray in one year. In further embodiments, the compounds, compositions, and methods can be used for therapeutic or prophylactic use in subjects who wish to minimize the effects of exposure to routine or background radiation, such as, in some embodiments, routine or everyday exposure to ultraviolet light.

In some embodiments, the compounds, compositions, and methods are used to prophylactically protect against or to treat exposure to extreme amounts of radiation, in some embodiments, radiation at or greater than about the LD10, LD20, LD50, or LD80 dose for an organism. Exposure to such high amounts of radiation can occur, in some embodiments, due to accidents at nuclear power plants, or accidents in handling extremely radioactive substances such as enriched uranium-235 or plutonium, or by proximity to a nuclear explosion or a bomb designed to spread lethal amounts of radioactivity.

In some embodiments, the compounds, compositions, and methods are used to prophylactically protect against or to treat exposure to radiation which damages the skin. Such radiation includes, in some embodiments, ultraviolet radiation. Topical administration of the compounds and compositions as disclosed herein may be used for such prophylactic protection or treatment (in some embodiments, in a lotion, cream, salve, or spray), as well as other routes of administration described below.

In some embodiments, the compounds, compositions, and methods are used to prophylactically protect against or to treat exposure to radiation which damages the eyes. Such radiation includes, in some embodiments, ultraviolet radiation. Topical administration of the compounds and compositions as disclosed herein may be used for such prophylactic protection or treatment (in some embodiments, in eye drops), as well as other routes of administration described below.

Assessment and Efficacy of Therapy in Context of Radiation Exposure

The utility of the compounds, compositions, and methods disclosed herein for therapeutic or prophylactic use for radiation exposure may be demonstrated both in vitro and in vivo. In general, to evaluate prophylactic/protective use, the compound or composition is administered prior to radiation exposure, and to evaluate therapeutic use, the compound or composition is administered during or after radiation exposure.

In some embodiments, the ability of cultured cells to form clones (colonies) may be evaluated as a function of exposure to radiation, such as X-rays. For example, cells are either not treated or are treated with a compound or composition disclosed herein at a certain time (in some embodiments, 30 minutes) prior to exposure. The degree of retention of ability to form clones after exposure, in comparison to untreated cells, is directly related to the protective effect of the drug. A typical experiment of this type may be carried out essentially as described by Snyder and Lachmann Radiation Res. (1989) 120:121-128. To evaluate efficacy for therapeutic use, similar experiments may be run, wherein the compound or composition disclosed herein is administered during or after radiation exposure.

In another embodiment, the utility of the compounds, compositions, and methods disclosed herein for therapeutic or prophylactic use for radiation exposure can be evaluated by measuring the production of DNA strand breaks upon exposure to radiation, such as X-rays. For example, cells are either not treated or are treated with a compound or composition disclosed herein at a certain time (in some embodiments, 30 minutes) prior to exposure. The extent of DNA strand breakage after exposure, in comparison to that in untreated cells, is inversely related to the protective effect of the drug. A typical experiment of this type may be carried out essentially as described by Snyder Int. J. Radiat. Biol. (1989) 55:773. To evaluate efficacy for therapeutic use, similar experiments may be run, wherein the compound or composition disclosed herein is administered during or after radiation exposure.

In vivo, the utility of the compounds, compositions, and methods disclosed herein for therapeutic or prophylactic use for radiation exposure may be evaluated by the survivability of mice exposed to whole body irradiation. In some embodiments, animals, either pre-dosed with a compound or composition disclosed herein, or not dosed (i.e., control animals), are exposed to whole body irradiation (such as, in some embodiments, 1500 rads). Control animals are expected to survive about 12-15 days. The degree of survivability of the dosed animals, in comparison to the controls, is directly related to the protective effect of the compound or composition administered. A typical experiment of this type may be carried out essentially as described by Carroll et al. J. Med. Chem. (1990) 33:2501. To evaluate efficacy for therapeutic use, similar experiments may be run, wherein the compound or composition disclosed herein is administered during or after radiation exposure.

Additionally, the production of DNA strand breaks in lymphocytes taken from treated animals exposed to whole body irradiation may be evaluated in comparison to untreated control animals. Alternatively, the viability and clonogenicity of bone marrow cells taken from treated animals exposed to whole body irradiation may be evaluated in comparison to cells taken from untreated control animals as described by Pike and Robinson J. Cell Physiol. (1970) 76:77-84.

The disclosure will be further understood by the following non-limiting examples.

Preparation of Compounds

The compounds disclosed herein can be prepared from readily available starting materials; non-limiting exemplary methods are described in the Examples. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthetic Reaction Parameters

The terms "solvent", "inert organic solvent" or "inert solvent" mean a solvent inert under the conditions of the reaction being described in conjunction therewith. Solvents employed in synthesis of the compounds disclosed herein include, in some embodiments, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions disclosed herein are inert organic solvents.

The term "q.s." means adding a quantity sufficient to achieve a stated function, e.g., to bring a solution to the desired volume (i.e., 100%).

The term "eq" means an equivalent quantity of one reagent with respect to another reagent.

The term "o/n" means overnight.

The compounds herein are synthesized by an appropriate combination of generally well-known synthetic methods. Techniques useful in synthesizing the compounds herein are both readily apparent and accessible to those of skill in the relevant art in light of the teachings described herein. While the Examples illustrate certain of the diverse methods available for use in assembling the compounds herein, they are not intended to define the scope of reactions or reaction sequences that are useful in preparing the compounds herein. Synthetic methods for other compounds disclosed herein will be apparent to one skilled in the art in view of the illustrative examples.

For all of the compounds and methods described herein, the quinone form can also be used in its reduced (hydroquinone) form when desired. Likewise, the hydroquinone form can also be used in its oxidized (quinone) form when desired. The reduced (hydroxy) form may readily be converted to the oxidized (quinone) form using methods known in the art. See, e.g., air, silica Miller et al PCT Intl Appl 2006130775 7 Dec. 2006. The oxidized (quinone) form may readily be converted to the reduced hydroxy form using methods known in the art. See, e.g., Zn, AcOH Fuchs et al EJOC 6 (2009) 833-40.

Exemplary Synthetic Schemes for Preparation of Compounds Disclosed Herein

Compounds of Formula I or II can be generally prepared as described in Scheme A. A suitable carboxylic acid (A) is coupled with a trisubstituted quinone (B) via a Kochi-Anderson/Minisci reaction (Commandeur, C.; Chalumeau, C.; Dessolin, J.; Laguerre, M. *European Journal of Organic Chemistry*, 2007, 3045-3052) to produce I.

Scheme A

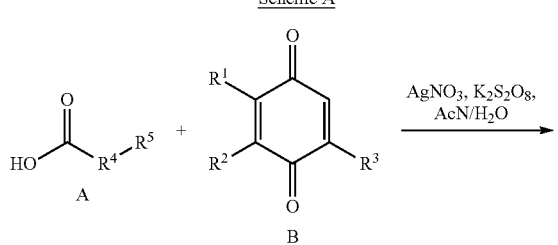

-continued

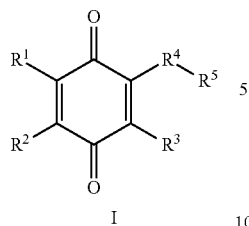

Certain carboxylic acids (A) and trisubstituted quinones (B) can be purchased commercially; others can be made by one skilled in the art.

Certain compounds of Formula I or II can also be generally prepared as described in Scheme B. A suitable carboxylic ester (A) is treated with Tongi reagent (Eisenberger, P.; Gischig, S.; Togni, A. *Chemistry A European Journal*, 2006, 12, 2579-2586) which effects the trifluoromethylation to provide ester B. Subsequent hydrogenation of the olefin furnishes ester C. Hydrolysis of C under standard conditions furnishes acid D. This acid is coupled with 2,3,5-trimethyl quinone via a Kochi-Anderson/Minisci reaction (Commandeur, C.; Chalumeau, C.; Dessolin, J.; Laguerre, M. *European Journal of Organic Chemistry*, 2007, 3045-3052) to produce E.

Scheme B

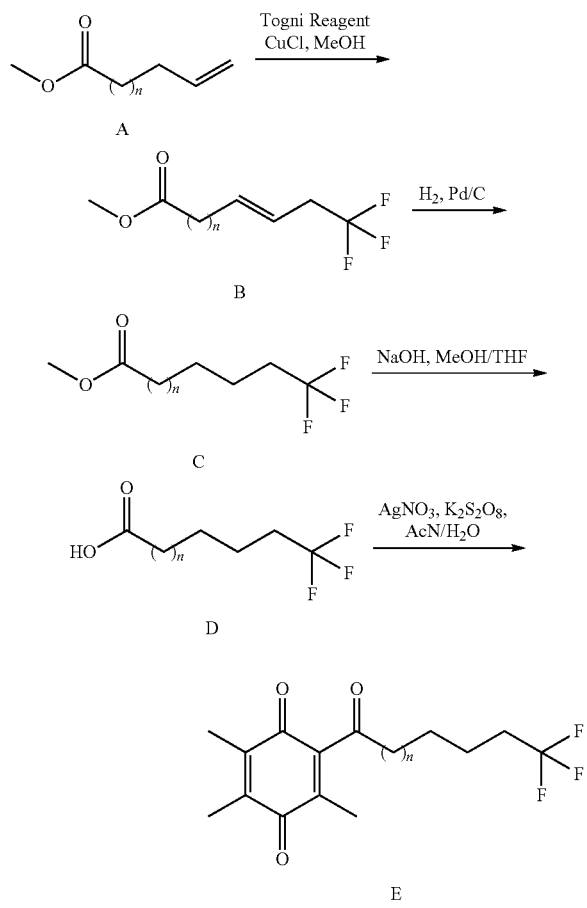

EXAMPLES

Example 1. 2,3,5-trimethyl-6-(8-(2,2,2-trifluoroethoxy)octyl)cyclohexa-2,5-diene-1,4-dione

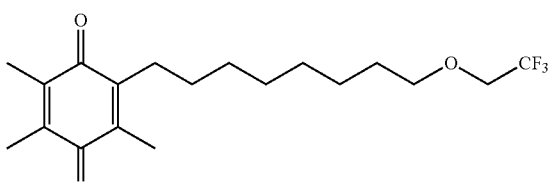

Step 1. 9-hydroxynonanoic acid (2)

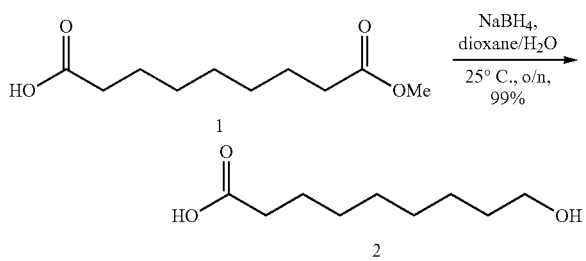

To a solution of 9-methoxy-9-oxononanoic acid (1) (2.0 g, 9.89 mmol, 1.0 eq) in dioxane/water (v/v, 25 mL/25 mL) was added $NaBH_4$ (2.6 g, 70.27 mmol, 7.0 eq) in portions. The reaction mixture was stirred at 25° C. for one night. Then the mixture was quenched by 1N aqueous solution of hydrochloric acid at 0° C. and extracted with dichloromethane (3×30 mL). The organic layers were dried over anhydrous $Na_2SO_4$ and concentrated to give 9-hydroxynonanoic acid (2) (2.0 g, 99%) which was used directly to next step without purification.

Step 2. Methyl 9-hydroxynonanoate (3)

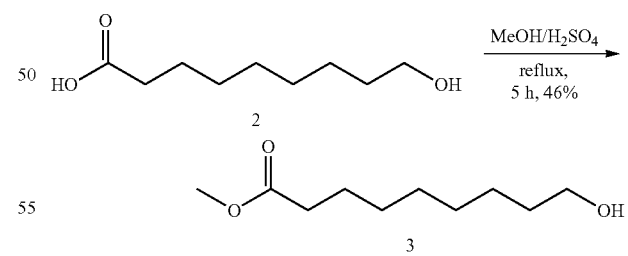

To a solution of 9-hydroxynonanoic acid (2) (1.0 g, 5.74 mmol, 1.0 eq) in methanol (30 mL) was added sulfuric acid (1 mL). The reaction mixture was heated to reflux for 5 h. Then the mixture was concentrated under reduced pressure and the residue was diluted with water (15 mL) and ethyl acetate (10 mL). The aqueous layer was back-extracted with additional ethyl acetate (2×10 mL). The combined organic layers were washed with brine and dried over anhydrous $Na_2SO_4$. The solvent was removed under reduced pressure and the crude was purified by column chromatography (PE/EA (petroleum ether/ethyl acetate)=10:1) to give methyl 9-hydroxynonanoate (3) (500 mg, 46%).

Step 3. Methyl 9-(2,2,2-trifluoroethoxy)nonanoate (4)

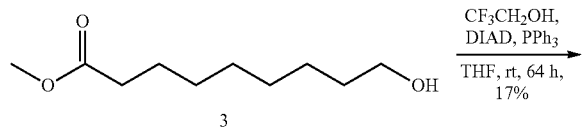

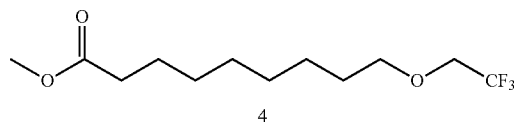

To a solution of methyl 9-hydroxynonanoate (3) (4.0 g, 21.24 mmol, 1.0 eq) in THF (tetrahydrofuran) (100 mL) were added CF$_3$CH$_2$OH (3.19 g, 31.89 mmol, 1.5 eq), DIAD (Diisopropyl azodicarboxylate) (6.45 g, 31.89 mmol, 1.5 eq) and PPh$_3$ (8.37 g, 31.91 mmol, 1.5 eq). The mixture was stirred at rt (room temperature) for 64 hours (h) under nitrogen atmosphere. Then the mixture was concentrated under reduced pressure and the residue was purified by column chromatography (PE/EA=20:1) to give methyl 9-(2,2,2-trifluoroethoxy)nonanoate (4) (1.0 g, 17%).

Step 4. 9-(2,2,2-trifluoroethoxy)nonanoic acid (5)

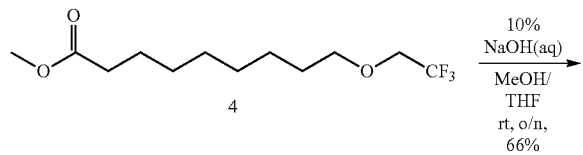

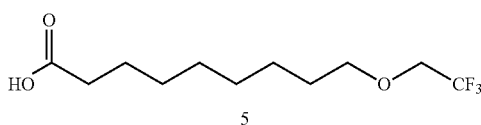

To a solution of methyl 9-(2,2,2-trifluoroethoxy)nonanoate (4) (1.0 g, 3.70 mmol, 1.0 eq) in methanol/THF (v/v, 20 mL/20 mL) was added 10% aqueous solution of sodium hydroxide (7.4 g, 18.5 mmol, 5.0 eq) at rt. The reaction mixture was stirred at rt overnight. The mixture was concentrated and adjusted pH to 3 with 1N aqueous solution of hydrochloric acid. Then the mixture was extracted with dichloromethane (2×10 mL). The organic layers were dried over anhydrous Na$_2$SO$_4$ and concentrated to give crude 9-(2,2,2-trifluoroethoxy)nonanoic acid (5) (626 mg, 66%) which was used directly to next step without purification.

Step 5. 2,3,5-trimethylcyclohexa-2,5-diene-1,4-dione (7)

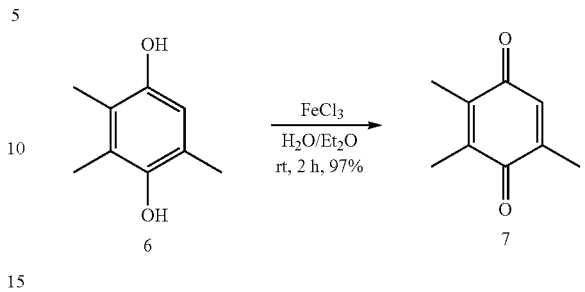

To a stirred solution of 2,3,5-trimethylbenzene-1,4-diol (6) (10 g, 65.71 mmol, 1.0 eq) in ether (100 mL) at 23° C. was mixed with ferric chloride (23.4 g, 144.27 mmol, 2.2 eq) in water (150 mL). The reaction mixture was stirred for about 2 hours. The organic phase was separated and the aqueous phase was extracted with ether (3×50 mL). The combined organic phases were dried over Na$_2$SO$_4$, and concentrated to give 2,3,5-trimethylcyclohexa-2,5-diene-1,4-dione (7) (9.6 g, 97%).

Step 6. 2,3,5-trimethyl-6-(8-(2,2,2-trifluoroethoxy)octyl)cyclohexa-2,5-diene-1,4-dione (Example 1)

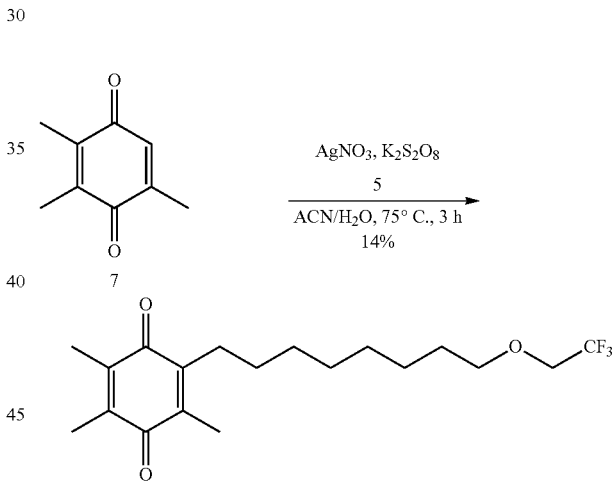

Example 1

To a solution of 2,3,5-trimethylcyclohexa-2,5-diene-1,4-dione (7) (184 mg, 1.22 mmol, 1.0 eq) and 9-(2,2,2-trifluoroethoxy)nonanoic acid (5) (313 mg, 1.22 mmol, 1.0 eq) in acetonitrile (30 mL) was added silver nitrate (212 mg, 1.25 mmol, 1.02 eq). To the mixture at 75° C. was slowly added a solution of K$_2$S$_2$O$_8$ (362 mg, 1.34 mmol, 1.1 eq) in water (60 mL) over 2 h. After the addition, the reaction mixture was stirred for another 3 h. The mixture was poured into water (15 mL). The aqueous layer was extracted with ethyl acetate (3×20 mL), the combined organic phases were dried over Na$_2$SO$_4$, concentrated and the residue was purified by prep-HPLC to give 2,3,5-trimethyl-6-(8-(2,2,2-trifluoroethoxy)octyl)cyclohexa-2,5-diene-1,4-dione (Example 1) (62.4 mg, 14%) as oil. $^1$H NMR (400 MHz, CDCl$_3$): δ 3.82-3.74 (m, 2H), 3.57 (t, J=6.8 Hz, 2H), 2.44 (t, J=7.2 Hz, 2H), 2.00 (s, 3H), 1.99 (s, 6H), 1.60-1.58 (m, 2H), 1.34-1.30 (m, 10H).

Example 2. 2,3,5-trimethyl-6-(9,9,9-trifluorononyl)cyclohexa-2,5-diene-1,4-dione

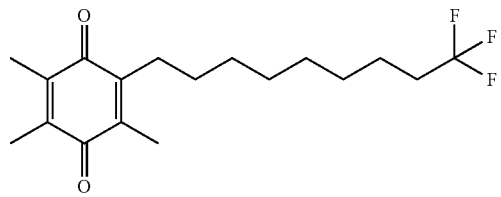 [SMILES: CC1=C(C)C(=O)C(CCCCCCCCC(F)(F)F)=C(C)C1=O]

Step 1. Non-8-enoic acid (9)

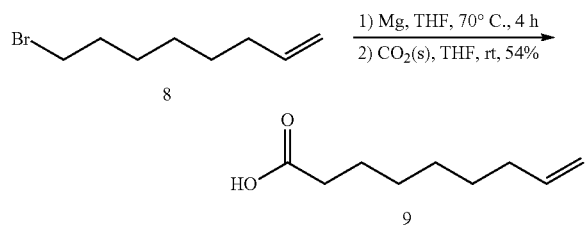

Magnesium (2.76 g, 0.114 mol, 1.1 eq) and a grain of iodine in three-neck flask was degassed with nitrogen. Then 25 percent volume of 8-bromooct-1-ene (8) (20 g, 0.105 mol, 1.0 eq) in THF (250 mL) was added into the mixture and the stirred mixture was heated to 70° C. until yellow brown disappeared. Then the remaining solution was added into the mixture dropwise and stirred at that temperature for additional 4 h. The solution was cooled to rt and CO$_2$(s) (46.2 g, 1.05 mol, 10.0 eq) in THF was added. After the addition, the mixture was warmed to rt and quenched by saturated solution of NH$_4$Cl. Then the mixture was extracted with ethyl acetate, separated and the organic phase was dried over Na$_2$SO$_4$, concentrated under reduced pressure. The residue was purified by column chromatography (PE/EA=100:1 to 50:1) to give non-8-enoic acid (9) (8.9 g, 54%).

Step 2. Methyl non-8-enoate (10)

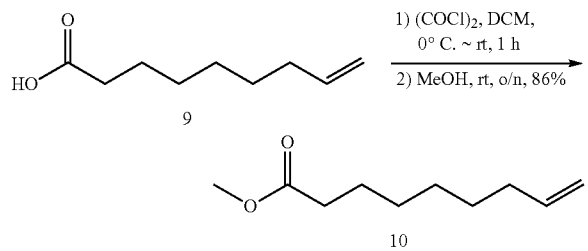

To a solution of non-8-enoic acid (9) (3.0 g, 0.019 mol, 1.0 eq) in dichloromethane (30 mL) at 0° C. was added oxalyl chloride (2.68 g, 0.021 mol, 1.1 eq) dropwise. The reaction mixture was warmed to rt and stirred 1 h. Then the mixture was concentrated under reduced pressure, and the residue was dissolved in methane (30 mL) and stirred at rt overnight. The mixture was concentrated and the crude was purified by column chromatography (PE/EA=100:1) to give methyl non-8-enoate (10) (2.83 g, 86%).

Step 3. Methyl (E)-10,10,10-trifluorodec-8-enoate (11)

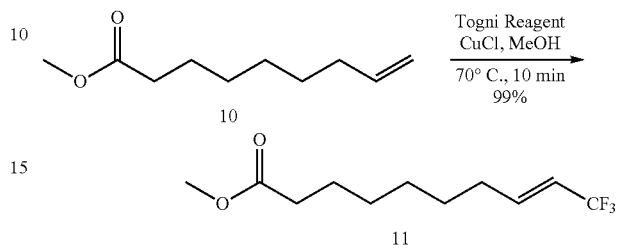

A flame-dried vial equipped with a magnetic stir bar was charged with Togni reagent II (1.70 g, 5.14 mmol, 1.75 eq) as well as copper (I) chloride (29.1 mg, 0.294 mmol, 0.1 eq), and then sealed with a septum. After three vacuum-nitrogen flush cycles, a solution of methyl non-8-enoate (10) (500 mg, 2.94 mmol, 1.0 eq) in methanol (5 mL) was then added via syringe. The vial was kept at 70° C. for 10 min. The reaction mixture was concentrated in vacuo and the residue was purified by column chromatography (PE/EA=100:1) to give methyl (E)-10,10,10-trifluorodec-8-enoate (11) (945 mg, 99%) as a colorless oil.

Step 4. Methyl 10,10,10-trifluorodecanoate (12)

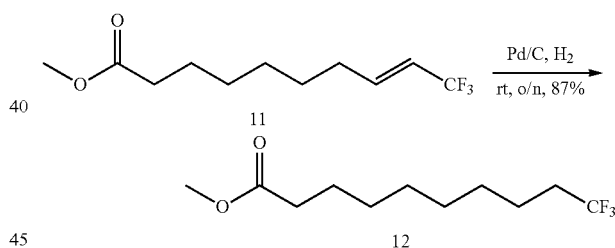

A mixture of (E)-10,10,10-trifluorodec-8-enoate (11) (0.95 g, 3.99 mmol, 1.0 eq) and Pd/C (100 mg) in methanol (10 mL) was added to a round bottom flask. The flask was purged and maintained with an atmosphere of hydrogen. And then the mixture was stirred at rt overnight. The mixture was filtered through Celite pad and the filtrate was concentrated to give methyl 10,10,10-trifluorodecanoate (12) (839 mg, 87%) which was used directly to next step without purification.

Step 5. 10,10,10-trifluorodecanoic acid (13)

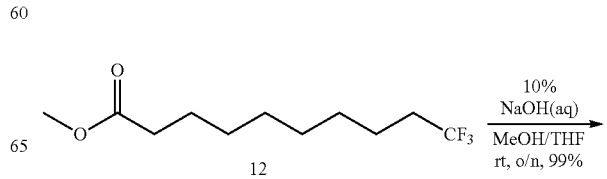

-continued

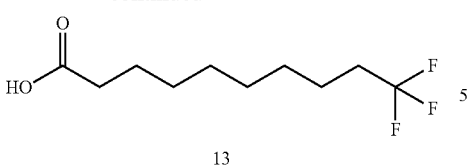

13

To a solution of methyl 10,10,10-trifluorodecanoate (12) (839 mg, 3.49 mmol, 1.0 eq) in methanol/THF (v/v, 10 mL/10 mL) was added 10 percent aqueous solution of sodium hydroxide (6.98 g, 17.45 mmol, 5.0 eq) at rt. The reaction mixture was stirred at rt overnight. The mixture was concentrated and adjusted pH to 3 with 1N aqueous solution of hydrochloric acid. Then the mixture was extracted with dichloromethane (2×20 mL). The organic layers were dried over anhydrous $Na_2SO_4$ and concentrated to give 10,10,10-trifluorodecanoic acid (13) (789 mg, 99%) which was used directly to next step without purification.

Step 6. 2,3,5-trimethyl-6-(9,9,9-trifluorononyl)cyclohexa-2,5-diene-1,4-dione (Example 2)

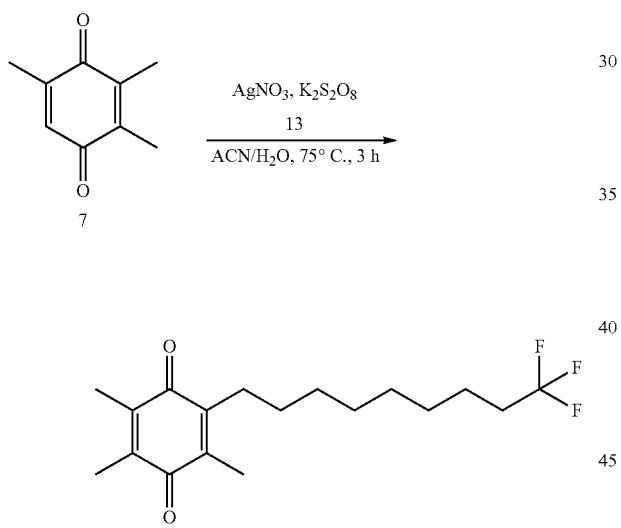

Example 2

To a solution of 2,3,5-trimethylcyclohexa-2,5-diene-1,4-dione (7) (261.3 mg, 1.74 mmol, 1.0 eq) and 10,10,10-trifluorodecanoic acid (13) (394 mg, 1.74 mmol, 1.0 eq) in acetonitrile (30 mL) was added silver nitrate (302.3 mg, 1.79 mmol, 1.02 eq). To the mixture at 75° C. was slowly added a solution of $K_2S_2O_8$ (516.3 mg, 1.91 mmol, 1.1 eq) in water (60 mL) over 2 h. After the addition, the reaction mixture was stirred for another 3 h. The mixture was poured into water (15 mL). The aqueous layer was extracted with ethyl acetate (3×20 mL), the combined organic phases were dried over $Na_2SO_4$, concentrated and the residue was purified by pre-HPLC to give 2,3,5-trimethyl-6-(9,9,9-trifluorononyl) cyclohexa-2,5-diene-1,4-dione (Example 2) (136.2 mg, 24%) as oil. $^1$H NMR (400 MHz, $CDCl_3$): δ 2.44 (t, J=6.8 Hz, 2H), 2.05-2.01 (m, 1H), 2.00 (s, 3H), 1.99 (s, 6H), 1.54-1.50 (m, 2H), 1.33-1.30 (m, 10H).

Example 3. 2-(8-methoxyoctyl)-3,5,6-trimethylcyclohexa-2,5-diene-1,4-dione

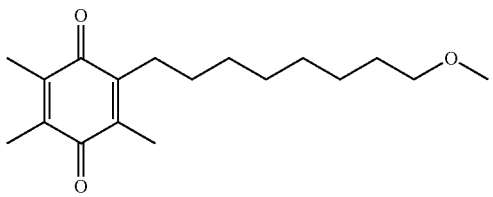

Step 1. Methyl 9-methoxynonanoate (14)

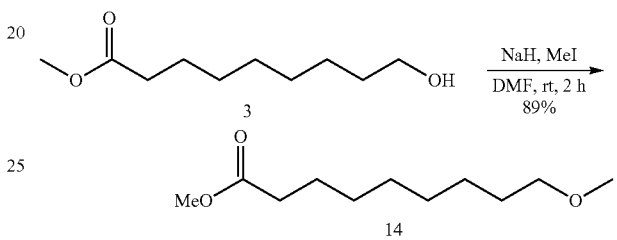

To a solution of methyl 9-hydroxynonanoate (3) (1.15 g, 6.11 mmol, 1.0 eq) in DMF (Dimethylformamide) (20 mL) was added NaH (60%, 337 mg, 9.17 mmol, 1.5 eq) at 0° C. After stirring 2 h at rt, iodomethane (1.3 g, 9.16 mmol, 1.5 eq) was added into the mixture and stirred at rt for 2 h. The mixture was quenched saturated aqueous solution of $NH_4Cl$ (20 mL) and extracted with ethyl acetate (3×20 mL). The organic layers were dried over $Na_2SO_4$ and concentrated. The residue was purified by column chromatography (PE/EA=20:1) to give methyl 9-methoxynonanoate (14) (1.1 g, 89%).

Step 2. 9-methoxynonanoic acid (15)

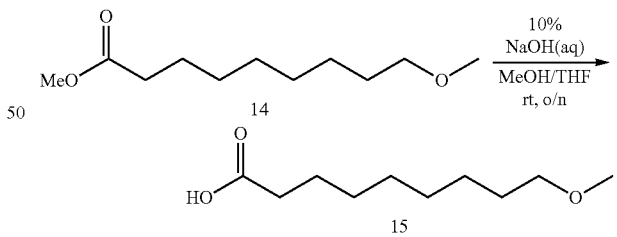

To a solution of methyl 9-methoxynonanoate (14) (1.1 g, 5.44 mmol, 1.0 eq) in methanol/THF (v/v, 20 mL/20 mL) was added 10% aqueous solution of sodium hydroxide (11 mL, 27.2 mmol, 5.0 eq) at rt. The reaction mixture was stirred at rt overnight. The mixture was concentrated and adjusted pH to 3 with 1N aqueous solution of hydrochloric acid. The mixture was extracted with dichloromethane (2×10 mL). Then the organic layers were dried over anhydrous $Na_2SO_4$ and concentrated to give crude 9-methoxynonanoic acid (15) (1.11 g) which was used directly to next step without purification.

Step 3. 2-(8-methoxyoctyl)-3,5,6-trimethylcyclohexa-2,5-diene-1,4-dione (Example 3)

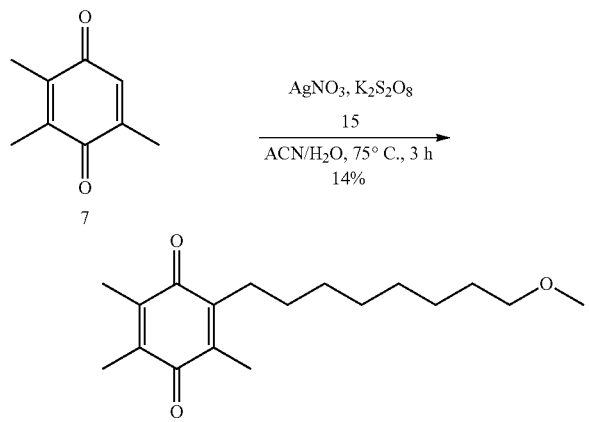

Example 3

To a solution of 2,3,5-trimethylcyclohexa-2,5-diene-1,4-dione (7) (0.44 g, 2.93 mmol, 1.0 eq) and 9-methoxynonanoic acid (15) (0.55 g, 2.92 mmol, 1.0 eq) in acetonitrile (30 mL) was added silver nitrate (0.51 g, 2.98 mmol, 1.02 eq). To the mixture at 75° C. was slowly added a solution of K$_2$S$_2$O$_8$ (0.87 g, 3.21 mmol, 1.1 eq) in water (60 mL) over 2 h. After the addition, the reaction mixture was stirred for another 3 h. The mixture was poured into water (15 mL). The aqueous layer was extracted with ethyl acetate (3×20 mL), the combined organic phases were dried over Na$_2$SO$_4$, concentrated and the residue was purified by preparative HPLC to give 2-(8-methoxyoctyl)-3,5,6-trimethylcyclohexa-2,5-diene-1,4-dione (Example 3) (119.9 mg, 14%) as oil. $^1$H NMR (400 MHz, CDCl$_3$): δ 3.35 (t, J=6.4 Hz, 2H), 3.31 (s, 3H), 2.44 (t, J=7.2 Hz, 2H), 2.03-2.01 (M, 1H), 2.00 (s, 3H), 1.99 (s, 6H), 1.97-1.94 (m, 1H), 1.63-1.52 (m, 2H), 1.33-1.27 (m, 8H).

Example 4. 2,3,5-trimethyl-6-(11,11,11-trifluoroundecyl)cyclohexa-2,5-diene-1,4-dione

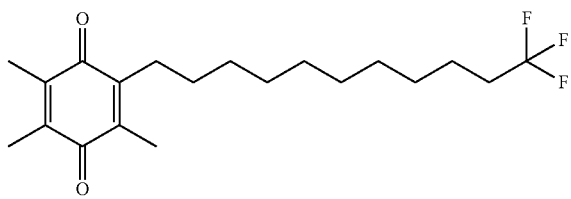 [SMILES: CC1=C(C)C(=O)C(CCCCCCCCCCC(F)(F)F)=C(C)C1=O]

Step 1. Methyl undec-10-enoate (17)

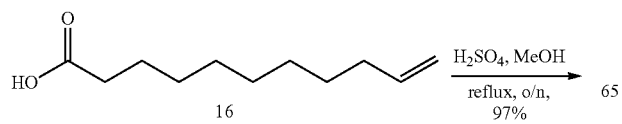

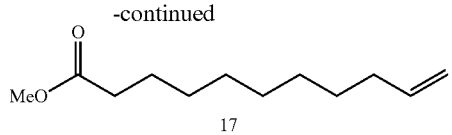

A stirred mixture of undec-10-enoic acid (16) (20 g, 108.53 mmol, 1.0 eq) and sulfuric acid (5 mL) in methanol (200 mL) was heated to reflux for one night. The resulting mixture was concentrated and the residue was diluted with ethyl acetate (200 mL) and aqueous solution of NaHCO$_3$ (100 mL). The aqueous layer was extracted with additional ethyl acetate (2×100 mL). The combined organic layer was dried over anhydrous sodium sulfate. The solvent was removed under reduced pressure to give methyl undec-10-enoate (17) (21 g, 97%). The compound was used without further purification.

Step 2. Methyl (E)-12,12,12-trifluorododec-9-enoate (18)

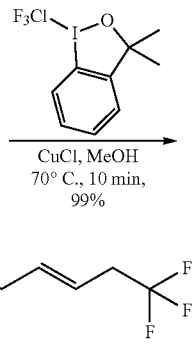

A flame-dried vial equipped with a magnetic stir bar was charged with Togni reagent II (1.456 g, 4.41 mmol, 1.75 eq) as well as copper (I) chloride (25 mg, 252.53 mmol, 0.1 eq), and then sealed with a septum. After three vacuum nitrogen flush cycles, a solution of methyl undec-10-enoate (17) (500 mg, 2.52 mmol, 1.0 eq) in methanol (5 mL) was then added via syringe. The vial was kept at 70° C. for 10 min. The reaction mixture was concentrated in vacuo and the residue was purified by column chromatography (PE/EA=100:1) to give methyl (E)-12,12,12-trifluorododec-9-enoate (18) (945 mg, 99%) as a colorless oil.

Step 3. Methyl 12,12,12-trifluorododecanoate (19)

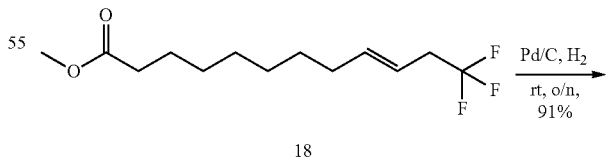

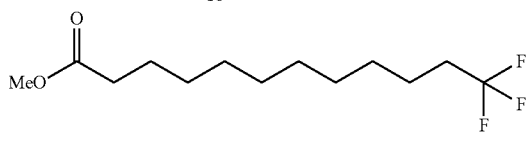

A mixture of methyl (E)-12,12,12-trifluorododec-9-enoate (18) (1.2 g, 4.51 mmol, 1.0 eq) and Pd/C (200 mg) in methanol (10 mL) was added to a round bottom flask. The flask was purged and maintained with an atmosphere of hydrogen. And then the mixture was stirred at rt overnight. The mixture was filtered through Celite and the filtrate was concentrated to give methyl 12,12,12-trifluorododecanoate (19) (1.1 g, 91%) which was used directly to next step without purification.

Step 4. 12,12,12-trifluorododecanoic acid (20)

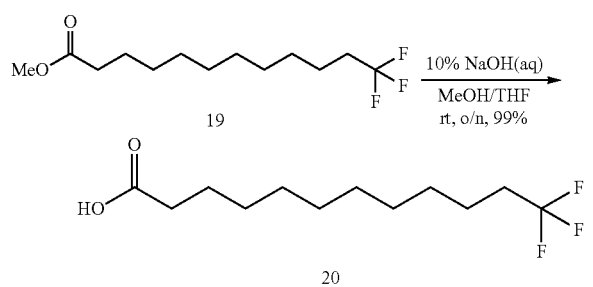

To a solution of methyl 12,12,12-trifluorododecanoate (19) (1.1 g, 4.1 mmol, 1.0 eq) in methanol (10 mL) and THF (10 mL) was added 10% aqueous solution of sodium hydroxide (3.28 g, 8.2 mmol, 2.0 eq) at rt. The reaction mixture was stirred at rt overnight. The mixture was concentrated and adjusted pH to 3 with 1N aqueous solution of hydrochloric acid. The mixture was extracted with dichloromethane (2×10 mL). Then the organic layers were dried over anhydrous $Na_2SO_4$ and concentrated to give 12,12,12-trifluorododecanoic acid (20) (1.09 g, 99%) which was used directly to next step without purification.

Step 5. 2,3,5-trimethyl-6-(11,11,11-trifluoroundecyl)cyclohexa-2,5-diene-1,4-dione (Example 4)

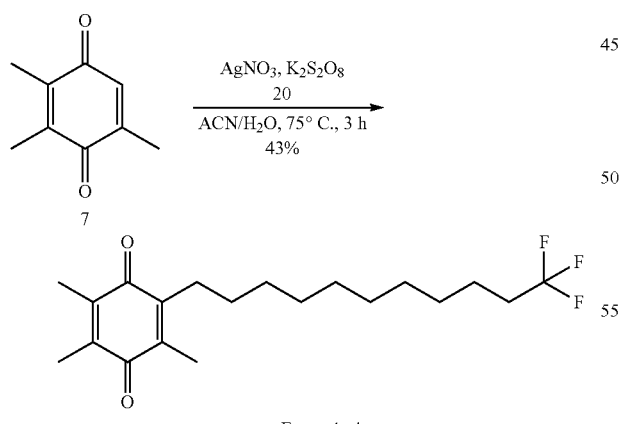

To a solution of 2,3,5-trimethylcyclohexa-2,5-diene-1,4-dione (7) (0.275 g, 1.83 mmol, 1.0 eq) and 12,12,12-trifluorododecanoic acid (20) (0.466 g, 1.83 mmol, 1.0 eq) in acetonitrile (30 mL) was added silver nitrate (0.317 g, 1.87 mmol, 1.02 eq). To the mixture at 75° C. was slowly added a solution of $K_2S_2O_8$ (0.545 g, 2.02 mmol, 1.1 eq) in water (60 mL) over 2 h. After the addition, the reaction mixture was stirred for another 3 h. The mixture was poured into water (15 mL). The aqueous layer was extracted with ethyl acetate (3×20 mL), the combined organic phases were dried over $Na_2SO_4$, concentrated and the residue was purified by preparative TLC (PE/EA=10:1) to give 2,3,5-trimethyl-6-(11,11,11-trifluoroundecyl)cyclohexa-2,5-diene-1,4-dione (Example 4) (280 mg, 43%) as an oil. $^1H$ NMR (400 MHz, $CDCl_3$): δ 2.45 (t, J=7.2 Hz, 2H), 2.08-2.02 (m, 2H), 2.01 (s, 3H), 2.00 (s, 6H), 1.58-1.51 (m, 2H), 1.34-1.27 (m, 14H). MS (m/z) for $C_{20}H_{29}F_3O_2$: found 358.05 (M−H).

Example 5. 2,3,5-trimethyl-6-(10-(2,2,2-trifluoroethoxy)decyl)cyclohexa-2,5-diene-1,4-dione

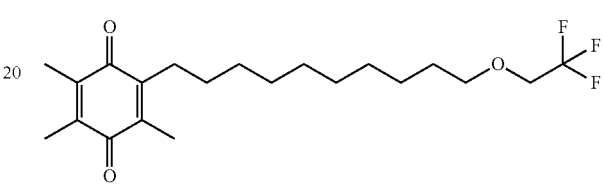

Step 1. 11-(2,2,2-trifluoroethoxy)undecanoic acid (22)

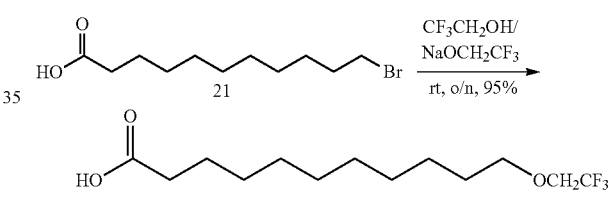

To a solution of 11-bromoundecanoic acid (21) (2.0 g, 7.54 mmol, 1.0 eq) in 2,2,2-trifluoroethanol (30 mL) was added sodium 2,2,2-trifluoroethanolate (10.58 g, 86.71 mmol, 11.5 eq). The mixture was stirred at rt overnight. The mixture was concentrated and the residue was diluted with water (20 mL) and ethyl acetate (20 mL). The aqueous layer was extracted with additional ethyl acetate (2×20 mL). The combined organic layer was dried over anhydrous $Na_2SO_4$ and concentrated to give 11-(2,2,2-trifluoroethoxy)undecanoic acid (22) (2.04 g, 95%) that was used without further purification.

Step 2. 2,3,5-trimethyl-6-(10-(2,2,2-trifluoroethoxy)decyl)cyclohexa-2,5-diene-1,4-dione (Example 5)

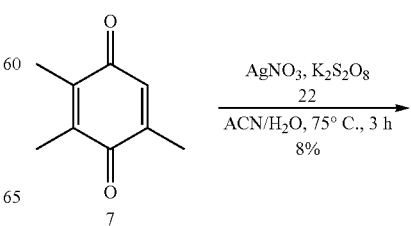

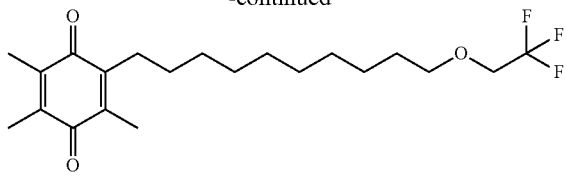

Example 5

To a solution of 2,3,5-trimethylcyclohexa-2,5-diene-1,4-dione (7) (0.528 g, 3.52 mmol, 1.0 eq) and 11-(2,2,2-trifluoroethoxy)undecanoic acid (22) (1.0 g, 3.52 mmol, 1.0 eq) in acetonitrile (30 mL) was added silver nitrate (0.610 g, 3.60 mmol, 1.02 eq). To the mixture at 75° C. was slowly added a solution of K$_2$S$_2$O$_8$ (1.046 g, 3.87 mmol, 1.1 eq) in water (60 mL) over 2 h. After the addition, the reaction mixture was stirred for another 3 h. The mixture was poured into water (15 mL). The aqueous layer was extracted with ethyl acetate (3×20 mL), the combined organic phases were dried over Na$_2$SO$_4$, concentrated and the residue was purified by preparative TLC (PE/EA=10:1) to give 2,3,5-trimethyl-6-(10-(2,2,2-trifluoroethoxy)decyl)cyclohexa-2,5-diene-1,4-dione (Example 5) (105.7 mg, 8%) as oil. $^1$H NMR (400 MHz, CDCl$_3$): δ 3.81-3.74 (m, 2H), 3.57 (t, J=6.8 Hz, 2H), 2.43 (t, J=7.2 Hz, 2H), 2.00 (s, 3H), 1.99 (s, 6H), 1.60-1.55 (m, 2H), 1.32-1.22 (m, 14H). MS (m/z) for: C$_{21}$H$_{31}$F$_3$O$_3$: found 388.15 (M–H).

Example 6. 2-(10-methoxydecyl)-3,5,6-trimethylcyclohexa-2,5-diene-1,4-dione

Step 1. 11-methoxyundecanoic acid (23)

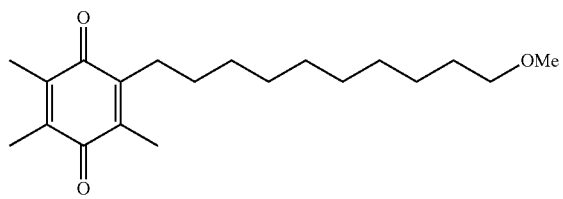 [SMILES: COCCCCCCCCCCC1=C(C)C(=O)C(C)=C(C)C1=O]

To a solution of 11-bromoundecanoic acid (21) (2.0 g, 7.54 mmol, 1.0 eq) in methanol (30 mL) was added sodium methylate (4.68 g, 86.67 mmol, 11.5 eq). The mixture was stirred at rt overnight. The mixture was concentrated and the residue was diluted with water (20 mL) and ethyl acetate (20 mL). The aqueous layer was extracted with additional ethyl acetate (2×20 mL). The combined organic layer was dried over anhydrous Na$_2$SO$_4$ and concentrated to give 11-methoxyundecanoic acid (23) (1.8 g, 99%). This compound was taken on without further purification.

Step 2. 2-(10-methoxydecyl)-3,5,6-trimethylcyclohexa-2,5-diene-1,4-dione (Example 6)

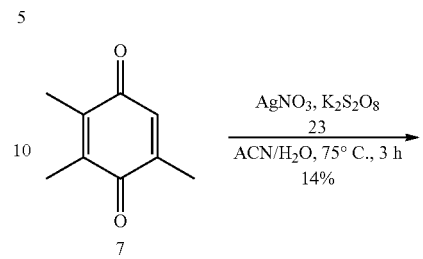

Example 6

To a solution of 2,3,5-trimethylcyclohexa-2,5-diene-1,4-dione (7) (500 mg, 3.33 mmol, 1.0 eq) and 11-methoxyundecanoic acid (23) (720 mg, 3.33 mmol, 1.0 eq) in acetonitrile (30 mL) was added silver nitrate (576.8 mg, 3.39 mmol, 1.02 eq). To the mixture at 75° C. was slowly added a solution of K$_2$S$_2$O$_8$ (990 mg, 3.66 mmol, 1.1 eq) in water (60 mL) over 2 h. After the addition, the reaction mixture was stirred for another 3 h. The mixture was poured into water (10 mL). The aqueous layer was extracted with ethyl acetate (3×15 mL), the combined organic phases were dried over Na$_2$SO$_4$, concentrated and the residue was purified by preparative TLC (PE/EA=10:1) to give 2-(10-methoxydecyl)-3,5,6-trimethylcyclohexa-2,5-diene-1,4-dione (Example 6) (144.6 mg, 14%) as oil. $^1$H NMR (400 MHz, CDCl$_3$): δ 3.35 (t, J=6.4 Hz, 2H), 3.32 (s, 3H), 2.44 (t, J=6.8 Hz, 2H), 2.00 (s, 3H), 1.99 (S, 6H), 1.56-1.52 (m, 2H), 1.35-1.26 (m, 14H). MS (m/z) for C$_{20}$H$_{32}$O$_3$: found 321.2 (M+H).

Example 7. 2-isopropyl-5,6-dimethyl-3-(11,11,11-trifluoroundecyl)cyclohexa-2,5-diene-1,4-dione

Step 1. 2,3-dimethylcyclohexa-2,5-diene-1,4-dione (25)

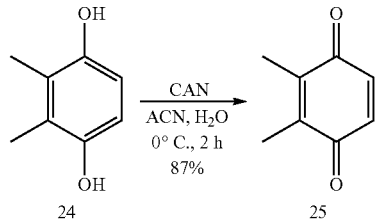

To a solution of 2,3-dimethylbenzene-1,4-diol (24) (3.0 g, 21.7 mmol, 1.0 eq) in acetonitrile (ACN) (30 mL) was added Ceric Ammonium Nitrate (CAN) (25.0 g, 45.7 mmol, 2.1 eq) in $H_2O$ at 0° C. over 2 h. The reaction was monitored by TLC. Upon completion, the mixture was diluted with water (30 mL), and extracted with ethyl acetate (EA) (2×30 mL). The organic layer was separated and dried ($MgSO_4$). The solvent was removed and the residue was purified by flash chromatography on silica (eluent petroleum ether:ethyl acetate (PE/EA)=50:1) to give 2,3-dimethylcyclohexa-2,5-diene-1,4-dione (25) (2.59 g, 87%) as a yellow oil.

Step 2. 5-isopropyl-2,3-dimethylcyclohexa-2,5-diene-1,4-dione (26)

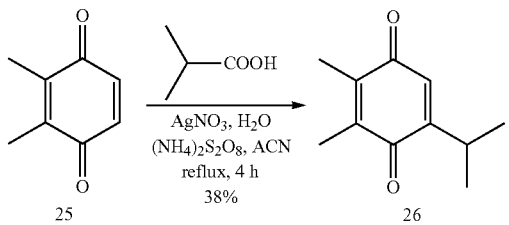

A mixture of 2,3-dimethylcyclohexa-2,5-diene-1,4-dione (25) (2.59 g, 19 mmol, 1.0 eq), 2-methylpropionic acid (1.67 g, 19 mmol, 1.0 eq) and $AgNO_3$ (17.8 mg, 105 mmol, 5.5 eq) in ACN (60 mL) and water (15 mL) was degassed with nitrogen. The mixture was stirred at 80° C. for 3 min, then $(NH_4)_2S_2O_8$ (3.47 g, 15.2 mmol, 0.8 eq) in $H_2O$ (10 mL) was added slowly at 80° C. and stirred for 4 h. The reaction was monitored by TLC. Upon completion, the mixture was diluted with water (30 mL), extracted with EA (2×60 mL), washed with brine and dried over $Na_2SO_4$ to obtain 5-isopropyl-2,3-dimethylcyclohexa-2,5-diene-1,4-dione (26) (1.3 g, 38%) as a yellow oil which was used directly for next step without further purification.

Step 3. 2-isopropyl-5,6-dimethyl-3-(11,11,11-trifluoroundecyl)cyclohexa-2,5-diene-1,4-dione (Example 7)

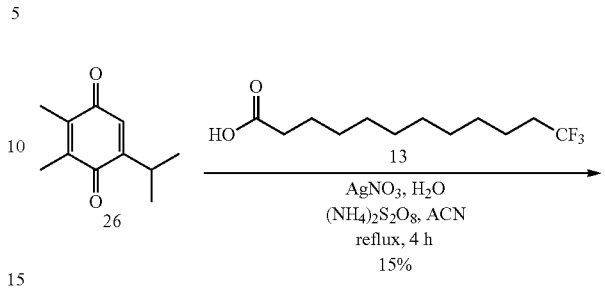

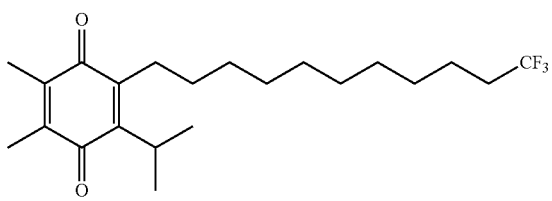

Example 7

A mixture of 5-isopropyl-2,3-dimethylcyclohexa-2,5-diene-1,4-dione (26) (500 mg, 2.8 mmol, 1.25 eq), 10,10,10-trifluorodecanoic acid (13) (525 mg, 2.25 mmol, 1.0 eq) and $AgNO_3$ (2.1 g, 12.4 mmol, 5.5 eq) in ACN (24 mL) and water (8 mL) was degassed with nitrogen. The mixture was stirred at 80° C. for 3 min, then $(NH_4)_2S_2O_8$ (409 mg, 1.79 mmol, 0.8 eq) in $H_2O$ (3 mL) was added slowly at 80° C. and stirred for 4 h. The reaction was monitored by TLC. Upon completion, the mixture was diluted with water (20 mL), extracted with EA (2×30 mL), washed with brine and dried over $Na_2SO_4$. The solvent was removed to give a residue. The residue was purified by flash chromatography on silica (PE/EA=300:1) and prep-HPLC to get 2-isopropyl-5,6-dimethyl-3-(11,11,11-trifluoroundecyl)cyclohexa-2,5-diene-1,4-dione (Example 7) (162 mg, 15%) as a yellow oil. $^1$H NMR (400 MHz, $CDCl_3$): δ 3.02-2.97 (m, 1H), 2.48 (t, J=6.8 Hz, 2H), 2.09-2.01 (m, 2H), 1.98-1.96 (m, 6H), 1.58-1.51 (m, 2H), 1.41-1.26 (m, 20H).

Example 8—N-(4,5-dimethyl-3,6-dioxo-2-(11,11,11-trifluoroundecyl)cyclohexa-1,4-dien-1-yl)methanesulfonamide

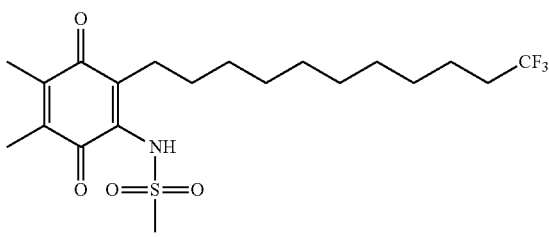 [SMILES: CC1=C(C)C(=O)C(NS(C)(=O)=O)=C(CCCCCCCCCCC(F)(F)F)C1=O]

Step 1. 2-bromo-5,6-dimethyl-3-(11,11,11-trifluoroundecyl)cyclohexa-2,5-diene-1,4-dione (28)

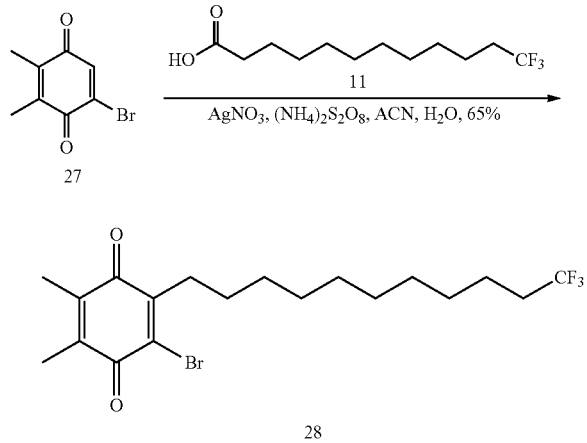 [SMILES: CC1=C(C)C(=O)C(Br)=CC1=O ; O=C(O)CCCCCCCCCCC(F)(F)F ; CC1=C(C)C(=O)C(CCCCCCCCCCC(F)(F)F)=C(Br)C1=O]

To a stirred solution of 5-bromo-2,3-dimethylcyclohexa-2,5-diene-1,4-dione (27) (400 mg, 1.86 mmol, 1.0 eq) and 12,12,12-trifluorododecanoic acid (11) (708.7 mg, 2.79 mmol, 1.5 eq) in MeCN (30 mL) was added AgNO$_3$ (94.8 mg, 0.558 mmol, 0.3 eq). The reaction was stirred at 80° C. for 30 min under nitrogen atmosphere. (NH$_4$)$_2$S$_2$O$_8$ (1.1 g, 4.84 mmol, 2.6 eq) in H$_2$O (20 mL) was added and the mixture was stirred at 80° C. for 3 h. The reaction was monitored by TLC. The resulting mixture was cooled to room temperature, extracted with EA (3×20 mL), and concentrated under reduced pressure. The residue was purified by flash chromatography on silica (PE/EA=50:1-20:1) to obtain 2-bromo-5,6-dimethyl-3-(11,11,11-trifluoroundecyl)cyclohexa-2,5-diene-1,4-dione (28) (515 mg, 65%) as a yellow solid.

Step 2. N-(4,5-dimethyl-3,6-dioxo-2-(11,11,11-trifluoroundecyl)cyclohexa-1,4-dien-1-yl)methanesulfonamide

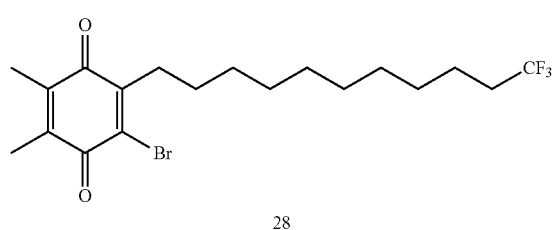

A mixture of 2-bromo-5,6-dimethyl-3-(11,11,11-trifluoroundecyl)cyclohexa-2,5-diene-1,4-dione (28) (315 mg, 0.745 mmol, 1.0 eq), methanesulfonamide (29) (78 mg, 0.82 mmol, 1.1 eq) and Cs$_2$CO$_3$ (365.8 mg, 1.12 mmol, 1.5 eq) in DMF (6 mL) was stirred at 80° C. for 2 h. The reaction was monitored by TLC. The resulting mixture was added HCl to adjust pH <7, extracted with EA (3×10 mL). The organic layer was washed by water, brine, dried over Na$_2$SO$_4$ and concentrated. The resultant residue was purified by flash chromatography on silica (PE:EA=5:1) to give N-(4,5-dimethyl-3,6-dioxo-2-(11,11,11-trifluoroundecyl)cyclohexa-1,4-dien-1-yl)methanesulfonamide (Example 8) (100 mg, 31%) as a yellow solid. $^1$H NMR (400 MHz, DMSO-d$_6$): δ 9.25 (s, 1H), 3.19 (s, 3H), 2.47-2.42 (m, 2H), 2.21-2.14 (m, 2H), 1.95 (s, 6H), 1.45-1.40 (m, 2H), 1.35-1.21 (m, 14H). MS (m/z) for C$_{20}$H$_{30}$F$_3$NO$_4$S: found 436 (M−H).

Example 9—2-(10-isopropoxydecyl)-3,5,6-trimethylcyclohexa-2,5-diene-1,4-dione

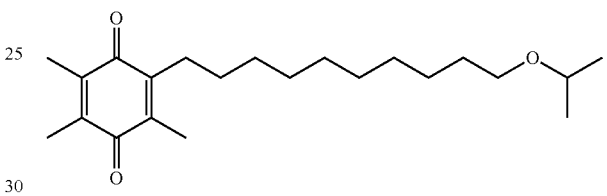

Step 1. 11-isopropoxyundecanoic acid (31)

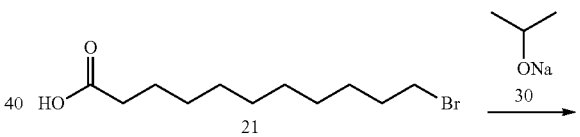 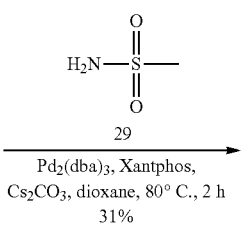

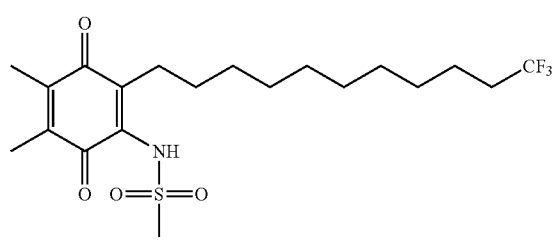

Example 8

-continued

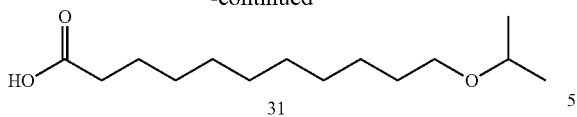

11-bromoundecanoic acid (21) (2.65 g, 10.0 mmol, 1.0 eq) was added to a solution of sodium propan-2-olate (8.2 g, 100.0 mmol, 10.0 eq) in isopropanol (100 mL) (in situ formed from Na and isopropanol). The mixture was stirred at 80° C. for 16 h. The mixture was concentrated and the residue was dissolved with water (20 mL) and extracted with DCM (20 mL). The aqueous layer was acidified to ~pH 3 with 6 M HCl and then extracted with DCM (20 mL×3). The combined organic layer dried over anhydrous $Na_2SO_4$ and concentrated to give 11-isopropoxyundecanoic acid (31) (1.0 g, 42%) which was used directly for the next step without further purification.

Step 2. 2-(10-isopropoxydecyl)-3,5,6-trimethylcyclohexa-2,5-diene-1,4-dione

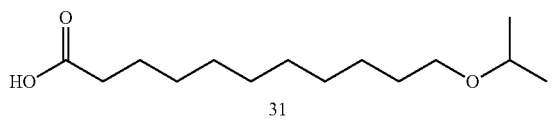

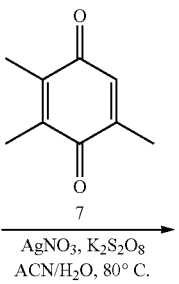

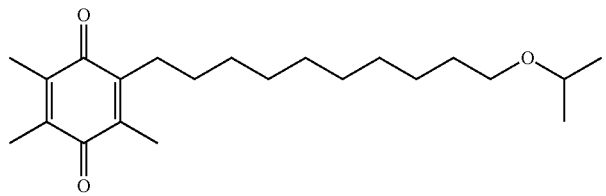 [SMILES: CC1=C(C)C(=O)C(CCCCCCCCCCOC(C)C)=C(C)C1=O]

Example 9

To a solution of 2,3,5-trimethylcyclohexa-2,5-diene-1,4-dione (7) (184 mg, 1.23 mmol, 1.0 eq) and 11-isopropoxyundecanoic acid (31) (300 mg, 1.23 mmol, 1.0 eq) in acetonitrile (5 mL) was added silver nitrate (230 mg, 1.35 mmol, 1.1 eq). To the mixture at 80° C. was slowly added a solution of $K_2S_2O_8$ (342 mg, 1.60 mmol, 1.3 eq) in water (10 mL). After the addition, the reaction mixture was stirred for another 2 h. The mixture was poured into water (15 mL). The aqueous layer was extracted with ethyl acetate (3×15 mL), the combined organic phases were dried over $Na_2SO_4$, concentrated and the residue was purified by column chromatography (PE/EA=40:1) to give 2-(10-isopropoxydecyl)-3,5,6-trimethylcyclohexa-2,5-diene-1,4-dione (Example 9) (125 mg, 29%) as a yellow oil. $^1$H NMR (400 MHz, DMSO-$d_6$) δ 3.49-3.43 (m, 1H), 3.29 (t, J=6.8 Hz, 2H), 2.38 (t, J=7.0 Hz, 2H), 1.93 (s, 3H), 1.92 (s, 6H), 1.43-1.39 (m, 2H), 1.26-1.22 (m, 14H), 1.03 (d, J=6.0 Hz, 6H). MS (m/z) for $C_{22}H_{36}O_3$: found 349 (M+H).

Example 10—2-(8-ethoxyoctyl)-3,5,6-trimethylcyclohexa-2,5-diene-1,4-dione

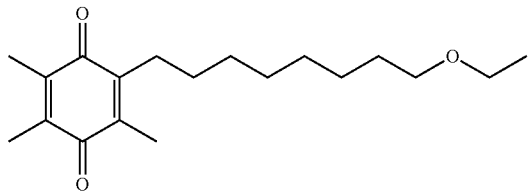 [SMILES: CCOCCCCCCCCC1=C(C)C(=O)C(C)=C(C)C1=O]

2-(8-ethoxyoctyl)-3,5,6-trimethylcyclohexa-2,5-diene-1,4-dione (Example 10) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 3.48-3.43 (q, J=5.3 Hz, 2H), 3.39 (t, J=6.6 Hz, 2H), 2.45 (t, J=7.4 Hz, 2H), 2.01-2.00 (m, 9H), 1.59-1.52 (m, 2H), 1.41-1.27 (m, 14H), 1.19 (t, J=7.0 Hz, 3H).

Example 11—2-(10-isobutoxydecyl)-3,5,6-trimethylcyclohexa-2,5-diene-1,4-dione

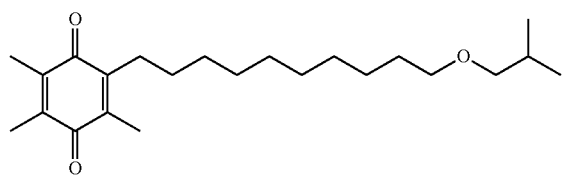 [SMILES: CC1=C(C)C(=O)C(CCCCCCCCCCOCC(C)C)=C(C)C1=O]

2-(10-isobutoxydecyl)-3,5,6-trimethylcyclohexa-2,5-diene-1,4-dione (Example 11) was prepared in a similar manner to 2-(10-isopropoxydecyl)-3,5,6-trimethylcyclohexa-2,5-diene-1,4-dione (Example 9). $^1$H NMR (400 MHz, CDCL3) δ 3.40-3.37 (t, J=6.8 Hz, 2H), 3.17-3.15 (d, J=6.8 Hz, 2H), 2.47-2.44 (m, 2H), 2.01-2.00 (d, J=4.0 Hz, 9H), 1.86-1.81 (m, 1H), 1.56 (s, 2H), 1.41-1.27 (m, 14H), 0.90-0.89 (d, J=6.8 Hz, 6H). MS (m/z) for $C_{23}H_{38}O_3$: found 363 (M+H).

Example 12—2,3,5-trimethyl-6-(10-propoxydecyl)
cyclohexa-2,5-diene-1,4-dione

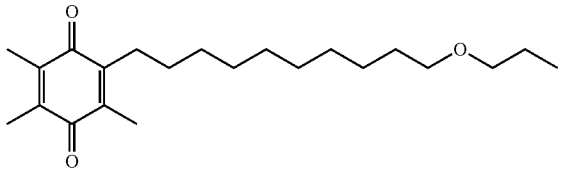 [SMILES: CCCOCCCCCCCCCCC1=C(C)C(=O)C(C)=C(C)C1=O]

2,3,5-trimethyl-6-(10-propoxydecyl)cyclohexa-2,5-diene-1,4-dione (Example 12) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 3.41-3.34 (m, 4H), 2.45 (t, J=7.2 Hz, 2H), 2.02-2.01 (m, 9H), 1.61-1.54 (m, 4H), 1.34-1.27 (m, 14H), 0.91 (t, J=7.2 Hz, 3H). MS (m/z) for C$_{22}$H$_{36}$O$_3$: found 349.35 (M+H).

Example 13—2,3,5-trimethyl-6-(10-phenoxydecyl)
cyclohexa-2,5-diene-1,4-dione

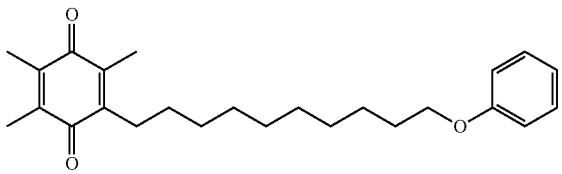 [SMILES: CC1=C(C)C(=O)C(CCCCCCCCCCOc2ccccc2)=C(C)C1=O]

2,3,5-trimethyl-6-(10-phenoxydecyl)cyclohexa-2,5-diene-1,4-dione (Example 13) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 7.29-7.25 (m, 2H), 6.94-6.88 (m, 3H), 3.95 (t, J=6.6 Hz, 2H), 2.46 (t, J=7.0 Hz, 2H), 2.02-2.01 (m, 9H), 1.79-1.74 (m, 2H), 1.46-1.41 (m, 2H), 1.35-1.30 (m, 12H).

Example 14—2-(8-isopropoxyoctyl)-3,5,6-trimethylcyclohexa-2,5-diene-1,4-dione

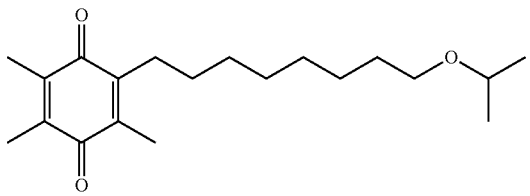 [SMILES: CC1=C(C)C(=O)C(CCCCCCCCOC(C)C)=C(C)C1=O]

2-(8-isopropoxyoctyl)-3,5,6-trimethylcyclohexa-2,5-diene-1,4-dione (Example 14) was prepared in a similar manner to 2-(10-isopropoxydecyl)-3,5,6-trimethylcyclohexa-2,5-diene-1,4-dione (Example 9). $^1$H NMR (400 MHz, DMSO-d$_6$) δ 3.48-3.42 (m, 1H), 3.28 (t, J=6.0 Hz, 2H), 2.38 (t, J=7.2 Hz, 2H), 1.93 (s, 3H), 1.91 (s, 6H), 1.41-1.39 (m, 2H), 1.23 (m, 14H), 1.02 (d, J=6.0 Hz, 6H). MS (m/z) for C$_{20}$H$_{32}$O$_3$: found 321.3 (M+H).

Example 15—2-(6-methoxyhexyl)-3,5,6-trimethyl-
cyclohexa-2,5-diene-1,4-dione

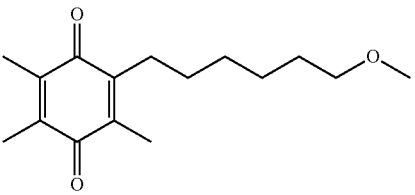

2-(6-methoxyhexyl)-3,5,6-trimethylcyclohexa-2,5-diene-1,4-dione (Example 15) was prepared in a similar manner to 2-(10-isopropoxydecyl)-3,5,6-trimethylcyclohexa-2,5-diene-1,4-dione (Example 9). $^1$H NMR (400 MHz, DMSO-d$_6$) δ 3.6 (t, J=6.4 Hz, 2H), 3.18 (s, 3H), 2.38 (t, J=7.2 Hz, 2H), 1.93 (s, 3H), 1.91 (s, 6H), 1.46-1.43 (m, 2H), 1.27 (m, 6H).

Example 16—2-(10-ethoxydecyl)-3,5,6-trimethylcyclohexa-2,5-diene-1,4-dione

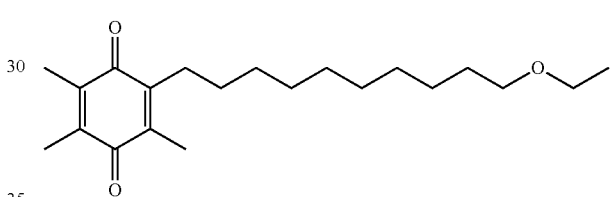

2-(10-ethoxydecyl)-3,5,6-trimethylcyclohexa-2,5-diene-1,4-dione (Example 16) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 3.48-3.43 (q, J=5.3 Hz, 2H), 3.39 (t, J=6.6 Hz, 2H), 2.45 (t, J=7.4 Hz, 2H), 2.01-2.00 (m, 9H), 1.59-1.52 (m, 2H), 1.41-1.27 (m, 14H), 1.19 (t, J=7.0 Hz, 3H).

Example 17—2,3,5-trimethyl-6-(8-propoxyoctyl)
cyclohexa-2,5-diene-1,4-dione

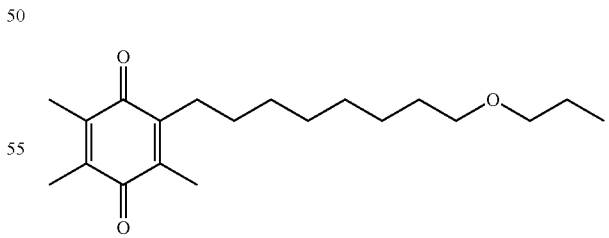

2,3,5-trimethyl-6-(8-propoxyoctyl)cyclohexa-2,5-diene-1,4-dione (Example 17) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 3.40-3.34 (m, 4H), 2.45 (t, J=6.8 Hz, 2H), 2.00 (s, 9H), 1.61-1.54 (m, 4H), 1.34-1.30 (m, 10H), 0.91 (t, J=7.2 Hz, 3H).

Example 18—2-(8-isobutoxyoctyl)-3,5,6-trimethyl-cyclohexa-2,5-diene-1,4-dione

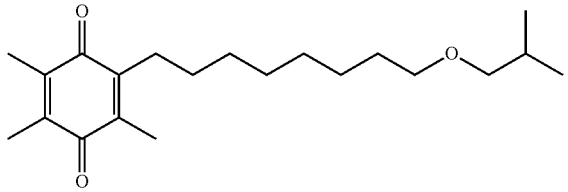 [SMILES: CC1=C(C)C(=O)C(CCCCCCCCOCC(C)C)=C(C)C1=O]

2-(8-isobutoxyoctyl)-3,5,6-trimethylcyclohexa-2,5-diene-1,4-dione (Example 18) was prepared in a similar manner to 2-(10-isopropoxydecyl)-3,5,6-trimethylcyclohexa-2,5-diene-1,4-dione (Example 9). $^1$H NMR (400 MHz, CDCL3) δ 3.39-3.36 (t, J=6.4 Hz, 2H), 3.16-3.14 (d, J=6.8 Hz, 2H), 2.44-2.43 (m, 2H), 2.00 (s, 9H), 1.85-1.82 (m, 1H), 1.59-1.53 (m, 2H), 1.34-1.30 (m, 10H), 0.89-0.88 (d, J=6.8 Hz, 6H).

Example 19—2,3,5-trimethyl-6-(8-((2-methylpyridin-3-yl)oxy)octyl)cyclohexa-2,5-diene-1,4-dione

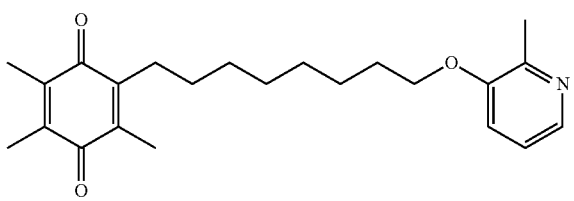 [SMILES: CC1=C(C)C(=O)C(CCCCCCCCOc2cccnc2C)=C(C)C1=O]

2,3,5-trimethyl-6-(8-((2-methylpyridin-3-yl)oxy)octyl) cyclohexa-2,5-diene-1,4-dione (Example 19) was prepared in a similar manner to 2-(10-isopropoxydecyl)-3,5,6-trimethylcyclohexa-2,5-diene-1,4-dione (Example 9). $^1$H NMR (400 MHz, CDCl$_3$) δ 8.04 (s, 1H), 7.04 (s, 2H), 3.93 (t, J=5.6 Hz, 2H), 2.45 (s, 5H), 1.99 (s, 9H), 1.79 (t, J=6.4 Hz, 2H), 1.46 (m, 2H), 1.35 (m, 8H). MS (m/z) for C$_{23}$H$_{31}$NO$_3$: found 370.3 (M+H).

Example 20—2-(10-(isobutyl(methyl)amino)decyl)-3,5,6-trimethylcyclohexa-2,5-diene-1,4-dione

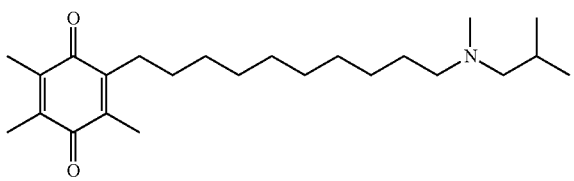 [SMILES: CC1=C(C)C(=O)C(CCCCCCCCCCN(C)CC(C)C)=C(C)C1=O]

Step 1. 2-(10-bromodecyl)-3,5,6-trimethylcyclohexa-2,5-diene-1,4-dione (32)

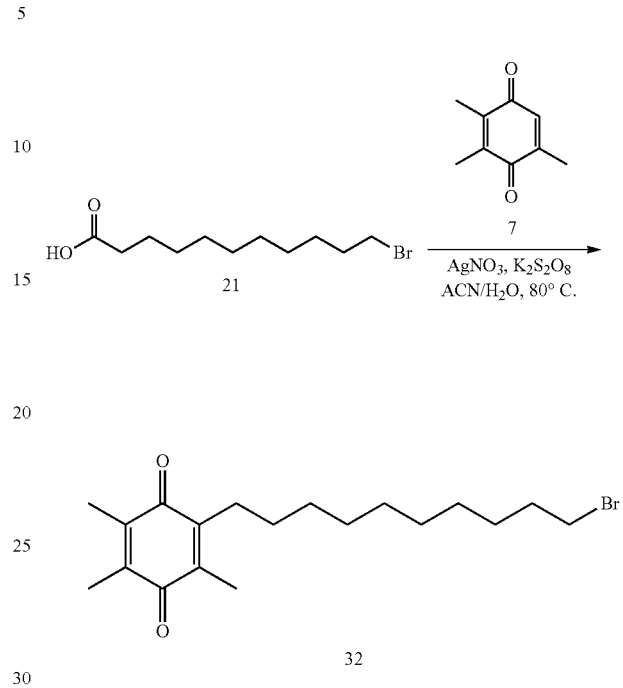

To a solution of 2,3,5-trimethylcyclohexa-2,5-diene-1,4-dione (7) (570 mg, 3.8 mmol, 1.0 eq) and 11-bromoundecanoic acid (21) (1.0 g, 3.8 mmol, 1.0 eq) in acetonitrile (10 mL) was added silver nitrate (714 mg, 4.2 mmol, 1.1 eq). The reaction solution was warmed to 80° C. To this was slowly added a solution of K$_2$S$_2$O$_8$ (1.3 g, 5.0 mmol, 1.3 eq) in water (20 mL). After the addition, the reaction mixture was stirred for another 2 h. The mixture was poured into water (20 mL). The aqueous layer was extracted with ethyl acetate (3×20 mL), the combined organic phases were dried over Na$_2$SO$_4$, concentrated and the residue was purified by column chromatography (PE/EA=40:1) to give 2-(10-bromodecyl)-3,5,6-trimethylcyclohexa-2,5-diene-1,4-dione (32) (400 mg, 29%) as a yellow oil.

Step 2. 2-(10-(isobutyl(methyl)amino)decyl)-3,5,6-trimethylcyclohexa-2,5-diene-1,4-dione (Example 20)

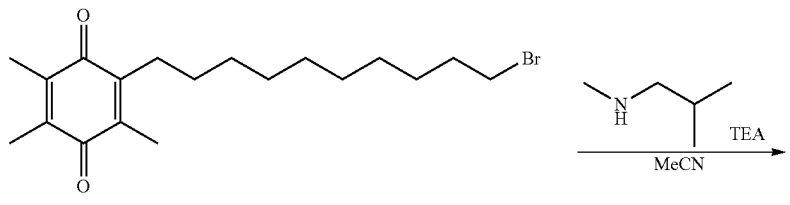

-continued

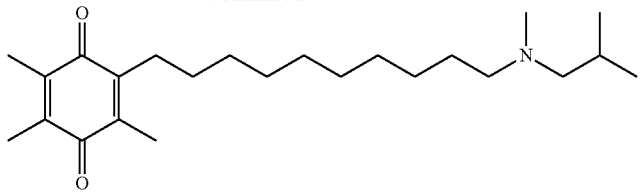

Example 26

A solution of 2-(10-bromodecyl)-3,5,6-trimethylcyclohexa-2,5-diene-1,4-dione (32) (1.0 g, 2.7 mmol, 1.0 eq), 1-propanamine (472 mg, 5.4 mmol, 2.0 eq), and trimethylamine (818 mg, 8.1 mmol, 3.0 eq) in MeCN (10 mL) was stirred at rt for 16 h. Solvents were removed to give a residue which was submitted to Prep-HPLC to give 2-(10-(isobutyl(methyl)amino)decyl)-3,5,6-trimethylcyclohexa-2,5-diene-1,4-dione (Example 20) (94 mg, 9.3%) as a yellow oil. $^1$H NMR (400 MHz, DMSO-$d_6$) δ 2.38 (t, J=7.0 Hz, 2H), 2.19 (t, J=7.2 Hz, 2H), 2.05 (s, 3H), 1.96-1.92 (m, 11H), 1.69-1.61 (m, 1H), 1.34-1.22 (m, 16H), 0.80 (d, J=6.8 Hz, 6H). MS (m/z) for $C_{24}H_{41}NO_2$: found 376.4 (M+H).

Example 21—2,3,5-trimethyl-6-(10-(pyrrolidin-1-yl)decyl)cyclohexa-2,5-diene-1,4-dione

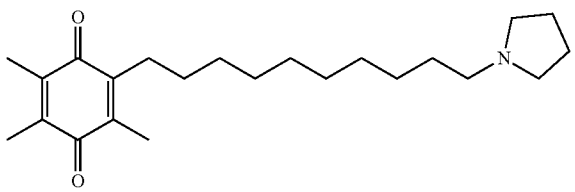 [SMILES: CC1=C(C)C(=O)C(CCCCCCCCCCN2CCCC2)=C(C)C1=O]

2,3,5-trimethyl-6-(10-(pyrrolidin-1-yl)decyl)cyclohexa-2,5-diene-1,4-dione (Example 21) was prepared in a similar manner to 2-(10-isopropoxydecyl)-3,5,6-trimethylcyclohexa-2,5-diene-1,4-dione (Example 20). $^1$H NMR (400 MHz, CD$_3$OD) δ 2.55 (m, 4H), 2.48-2.26 (m, 4H), 2.00 (s, 3H), 1.99 (s, 6H), 1.80 (m, 4H), 1.53 (m, 2H), 1.35-1.32 (m, 14H). MS (m/z) for $C_{23}H_{37}NO_2$: found 360.4 (M+H).

Example 22—2-(10-(isobutylamino)decyl)-3,5,6-trimethylcyclohexa-2,5-diene-1,4-dione

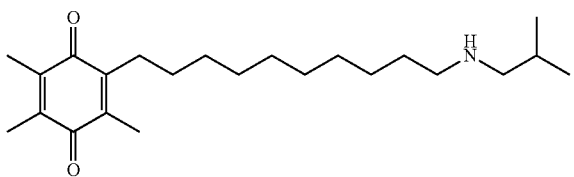

2-(10-(isobutylamino)decyl)-3,5,6-trimethylcyclohexa-2,5-diene-1,4-dione (Example 22) was prepared in a similar manner to 2-(10-isopropoxydecyl)-3,5,6-trimethylcyclohexa-2,5-diene-1,4-dione (Example 20). $^1$H NMR (400 MHz, DMSO-$d_6$) δ 2.84 (t, J=8.0 Hz, 2H), 2.71 (d, J=6.8 Hz, 2H), 2.38 (m, 2H), 1.93-1.92 (m, 10H), 1.56 (m, 2H), 1.24 (m, 14H), 0.91 (d, J=6.8 Hz, 6H). MS (m/z) for $C_{23}H_{39}NO_2$: found 362.3 (M+H).

Example 23. Biological Activity

In neuronal cells excess extracellular glutamate inhibits the cystine/glutamate antiporter leading to intracellular cysteine depletion, GSH depletion, ROS production and cell death, a phenomenon termed oxidative glutamate toxicity or oxytosis. Q7 cells (ST HDH Q7/7; immortalized mouse striatal cells) challenged with cystine-free media recapitulate this phenotype. An initial screen was performed to identify compounds effective in rescuing Q7 cells from death resulting from cystine deprivation. This method is further described in Yonezawa et al., J. Neurochem 67, 566-573 (1996), and Li et al., J Neurosci., 23, 5816-5826 (2003).

DMEM (Catalog no. 11995-040), DMEM without Cystine (Catalog no. 21013-024), Penicillin-streptomycin mix, L-Glutamine and Pyruvate were purchased from Gibco. Fetal Bovine Serum was obtained from Mediatech, Inc. Mouse striatum derived ST HDH Q7/7 (Q7) cells were obtained from Dr. M. MacDonald (Massachusetts General Hospital). Methionine and Vitamin K2 were purchased from Sigma Aldrich. Calcein AM was purchased from Anaspec. Geneticin (G418) Sulfate was purchased from Santa Cruz Biotechnology. Cell culture medium (Growth medium) was made by combining 50 mL Fetal Bovine Serum, 100 U/mL penicillin, 100 microgram/mL streptomycin and 400 microgram/mL Geneticin (G418) Sulfate; DMEM was added to make the volume up to 500 mL. Assay medium (without Cystine) was made by combining 50 mL Fetal Bovine Serum, 100 U/mL penicillin, 100 microgram/mL streptomycin, 4 mM L-Glutamine, 1 mM Pyruvate and 30 mg/L Methionine; DMEM without Cystine was added to make the volume up to 500 mL. During the course of the experiments, these solutions were stored at 4° C. The cells were grown in 10-cm diameter tissue culture-treated dishes. Every fourth day, the cells were subcultured by trypsinization and re-seeding at a cell density of 500,000 cells per dish.

Test samples were supplied in 1.5 mL glass vials. The compounds were diluted with an appropriate volume of DMSO to result in a 1 mM stock solution. Once dissolved, they were stored at −20° C.

Test samples were screened according to the following protocol:

Q7 cells were cultured routinely as described herein. For cell survival assays, cells were seeded in clear 96-well tissue culture-treated polystyrene plates by resuspending a cell suspension at a density of 100,000 cells/mL in growth medium, then dispensing 100 microliters of cell suspension per well using an electronic multichannel pipette, corresponding to 10,000 cells/well. The cell-containing plates were incubated 5 hours at 33° C. in an atmosphere with 95% humidity and 5% CO$_2$ to allow attachment of the cells to the culture plate.

Test compounds were thawed, and 2 microliters of a 1 mM stock solution was diluted in a microtiter plate well containing 98 microliters of 10% DMSO in $H_2O$, resulting in a 20 micromolar master solution. Serial dilutions from the master solution were made in 10% DMSO. The period between the single dilution steps was kept as short as possible (generally less than 30 seconds). 5 hours after cell seeding into the 96-well assay plate, the cell culture medium was removed by inverting the plates and gently patted onto paper towel. The plates were washed once with 100 microliters of PBS containing $Ca^{++}$ and $Mg^{++}$. PBS containing $Ca^{++}$ and $Mg^{++}$ were removed by inverting the plates and gently patted onto a paper towel. After washing the wells, 100 microliters of assay medium without Cystine was dispensed and then treated with 10 microliters of the various compound dilutions in triplicates. Final concentration of DMSO in the well was 1%.

After medium change to cystine-free medium and compound addition, cell plates were incubated at 33° C. in an atmosphere of 5% $CO_2$ and 95% humidity. 18 hours later, the medium from all plates was removed by inverting the plates and gently tapping the plate onto a paper towel. The plates were washed one time with 100 microliters of PBS containing $Ca^{++}$ and $Mg^{++}$ and removed by inverting the plates and patted onto a paper towel. 100 microliters of PBS (containing $Ca^{++}$ and $Mg^{++}$) containing 1 micromolar Calcein AM were then added to each well. The plates were incubated for 30 minutes at 33° C. Fluorescence (excitation/emission wavelengths of 488 nm and 525 nm, respectively) was read on a SpectraMax M2 fluorescence reader. Data was imported into Microsoft Excel. Prism and/or XLFit were then used to calculate the $EC_{50}$ values for each compound using standard four-parameter curve fitting algorithms.

The relative viability of test compound-treated cells were calculated relative to the average cystine-deprived, DMSO-treated cell viability (defined as 0% relative viability) and the average cystine-deprived, Vitamin K2 (1 micromolar) treated cell viability (defined as 100% relative viability). $EC_{50}$ was the concentration corresponding to 50% relative stability. Vitamin K2 treatment routinely completely rescued the cystine deprivation-induced reduction in cell viability, as defined by cell viability observed in parallel cell wells that were cultured in the presence of standard growth medium containing 200 micromolar cystine. The assay performance was gauged by Z-prime calculations on each assay plate, with observed Z-prime values of >0.5.

TABLE 2

Activity of representative compounds in oxidative stress model

| Compound | Synthesis Example # | $EC_{50}$* |
|---|---|---|
| [structure] | 1 | ++ |
| [structure] | 2 | ++ |
| [structure] | 3 | ++ |
| [structure] | 4 | +++ |

TABLE 2-continued

Activity of representative compounds in oxidative stress model

| Compound | Synthesis Example # | EC$_{50}$* |
|---|---|---|
| [structure: trimethylbenzoquinone with alkyl chain terminating in -O-CH$_2$-CF$_2$F] | 5 | +++ |
| [structure: trimethylbenzoquinone with alkyl chain terminating in OMe] | 6 | ++ |
| [structure: dimethyl-isopropyl benzoquinone with alkyl chain terminating in CF$_3$] | 7 | +++ |

*+++ is <0.5 µM;
++ is 0.5-1.0 µM;
+ is 1.0-2.0 µM

Example 24. Biological Activity—384-Well Cell Titer Glo (CTG) Q7 Cystine Deprivation Survival Assay Protocol In neuronal cells excess extracellular glutamate inhibits the cystine/glutamate antiporter leading to intracellular cysteine depletion, GSH depletion, ROS production and cell death, a phenomenon termed oxidative glutamate toxicity or oxytosis. Q7 cells (ST HDH Q7/7; immortalized mouse striatal cells) challenged with cystine-free media recapitulate this phenotype. An initial screen was performed to identify compounds effective in rescuing Q7 cells from death resulting from cystine deprivation. This method is further described in Yonezawa et al., J. Neurochem 67, 566-573 (1996), and Li et al., J Neurosci., 23, 5816-5826 (2003).

DMEM (Catalog no. 11995-040), DMEM without Cystine (Catalog no. 21013-024), PBS (Phosphate buffered saline), Penicillin-streptomycin mix, L-Glutamine and Pyruvate were purchased from Gibco. Fetal Bovine Serum was obtained from Mediatech, Inc. Mouse striatum derived ST HDH Q7/7 (Q7) cells were obtained from Dr. M. MacDonald (Massachusetts General Hospital). Methionine and Vitamin K2 were purchased from Sigma Aldrich. Cell Titer Glo 2.0 was purchased from Promega. Geneticin (G418) Sulfate was purchased from Santa Cruz Biotechnology. Cell culture medium (Growth medium) was made by combining 50 mL Fetal Bovine Serum, 100 U/mL penicillin, 100 microgram/mL streptomycin and 400 microgram/mL Geneticin (G418) Sulfate; DMEM was added to make the volume up to 500 mL. Assay medium (without Cystine) was made by combining 50 mL Fetal Bovine Serum, 100 U/mL penicillin, 100 microgram/mL streptomycin, 4 mM L-Glutamine, 1 mM Pyruvate and 30 mg/L Methionine; DMEM without Cystine was added to make the volume up to 500 mL. During the course of the experiments, these solutions were stored at 4° C. The cells were grown in 10-cm diameter tissue culture-treated dishes. Every fourth day, the cells were subcultured by trypsinization and re-seeding at a cell density of 500,000 cells per dish.

Test samples were supplied in 1.5 mL glass vials. The compounds were diluted with an appropriate volume of DMSO to result in a 1 mM stock solution. Once dissolved, they were stored at −20° C.

Test Samples were Screened According to the Following Protocol:

Q7 cells were cultured routinely as described herein. For 384-well cell survival assays, cells were seeded in clear bottom, black wall 384-well tissue culture-treated polystyrene plates by resuspending a cell suspension at a density of 50,000 cells/mL in growth medium, then dispensing 60 microliters of cell suspension per well using either an electronic multichannel pipette or a Multidrop™ Combi Reagent Dispenser (ThermoFisher Scientific), corresponding to 3,000 cells/well. The cell-containing plates were incubated 5 hours at 33° C. in an atmosphere with 95% humidity and 5% CO$_2$ to allow attachment of the cells to the culture plate.

5 hours after cell seeding into the 384-well assay plate, the cell culture medium was replaced by washing 2 times with 70 microliters/well PBS (without Ca$^{++}$ and Mg$^{++}$) using a BioTek ELx405 plate washer. After the final aspiration, 60 microliters/well of assay medium (without cystine) was added using the Multidrop Combi Reagent Dispenser. Within 45 minutes, test compounds were then added to varying final concentrations using the Tecan D300e Digital Dispenser, with subsequent back-filling with DMSO diluent to a final concentration of 0.3% (v/v).

After medium change to cystine-free medium and compound addition, cell plates were incubated at 33° C. in an atmosphere of 5% $CO_2$ and 95% humidity. 18 hours later, the plates were equilibrated to room temperature for 15 minutes. Then, 10 microliters/well of room temperature Cell Titer Glo 2.0 reagent was added using the Multidrop Combi Reagent Dispenser. After 15 minutes of incubation at room temperature, the luminescence (100 ms integration time) per well was determined using the BioTek Synergy plate reader. Data was imported into Microsoft Excel. ACAS Curve Curator (John McNeil and Company) was then used to calculate the $EC_{50}$ values for each compound using standard four-parameter curve fitting algorithms.

The relative viability of test compound-treated cells were calculated relative to the average cystine-deprived, DMSO-treated cell viability (defined as 0% relative viability) and the average cystine-deprived, Vitamin K2 (1 micromolar) treated cell viability (defined as 100% relative viability). $EC_{50}$ was the concentration corresponding to 50% relative viability. The assay performance was gauged by Z-prime calculations on each assay plate, with observed Z-prime values of >0.5.

TABLE 3

Activity of representative compounds in oxidative stress model

| Compound | Synthesis Example | Q7 Cystine Free CTG 384 CSA ($EC_{50}$) [μM] |
|---|---|---|
| 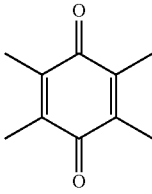 | 1 | +++ |
| 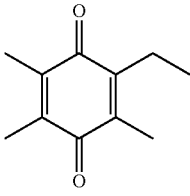 | 2 | +++ |
| 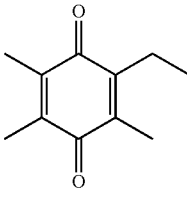 | 3 | +++ |
| 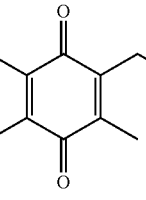 | 4 | ++++ |
| 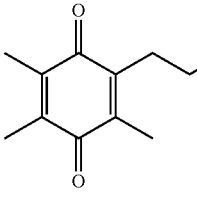 | 5 | ++++ |

TABLE 3-continued

Activity of representative compounds in oxidative stress model

| Compound | Synthesis Example | Q7 Cystine Free CTG 384 CSA (EC$_{50}$) [μM] |
|---|---|---|
| (trimethylbenzoquinone with -(CH$_2$)$_n$-OMe chain) | 6 | ++++ |
| (trimethylbenzoquinone with isopropyl and -(CH$_2$)$_n$-CF$_3$ chain) | 7 | +++ |
| (dimethylbenzoquinone with NHSO$_2$Me and -(CH$_2$)$_n$-CF$_3$ chain) | 8 | ++++ |
| (trimethylbenzoquinone with -(CH$_2$)$_n$-O-iPr chain) | 9 | ++++ |
| (trimethylbenzoquinone with -(CH$_2$)$_n$-OEt chain) | 10 | ++++ |
| (trimethylbenzoquinone with -(CH$_2$)$_n$-O-iBu chain) | 11 | ++++ |
| (trimethylbenzoquinone with -(CH$_2$)$_n$-O-nPr chain) | 12 | ++++ |

TABLE 3-continued
Activity of representative compounds in oxidative stress model
| Compound | Synthesis Example | Q7 Cystine Free CTG 384 CSA (EC$_{50}$) [μM] |
|---|---|---|
| 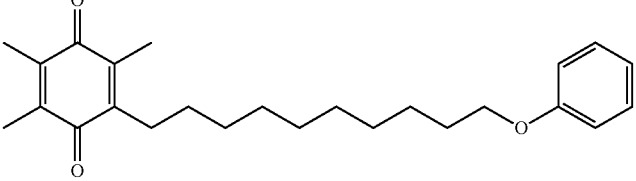 | 13 | ++++ |
| 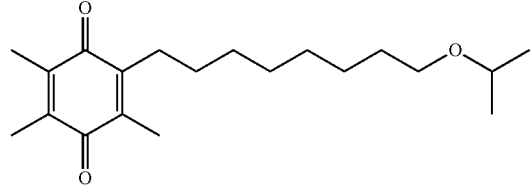 | 14 | ++++ |
| 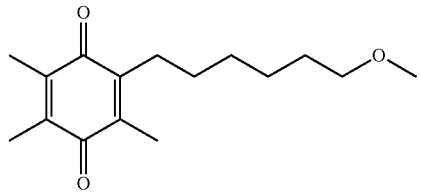 | 15 | +++ |
| 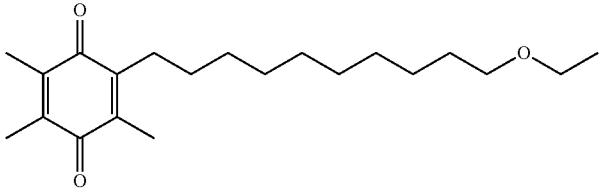 [SMILES: CCOCCCCCCCCCCC1=C(C)C(=O)C(C)=C(C)C1=O] | 16 | ++++ |
| 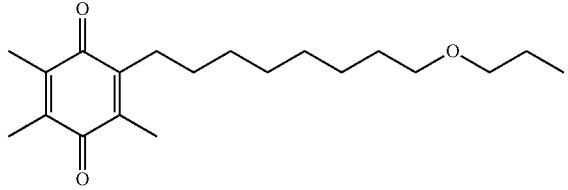 [SMILES: CCCOCCCCCCCCC1=C(C)C(=O)C(C)=C(C)C1=O] | 17 | ++++ |
| 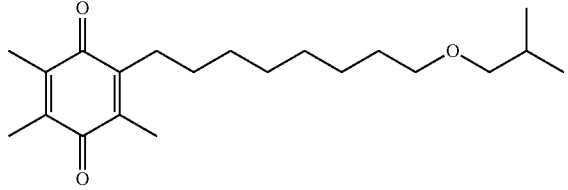 [SMILES: CC1=C(C)C(=O)C(CCCCCCCCOCC(C)C)=C(C)C1=O] | 18 | ++++ |
| 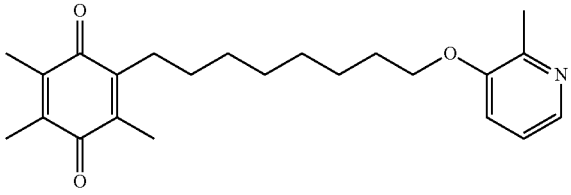 [SMILES: CC1=C(C)C(=O)C(CCCCCCCCOc2cccnc2C)=C(C)C1=O] | 19 | +++ |

TABLE 3-continued

Activity of representative compounds in oxidative stress model

| Compound | Synthesis Example | Q7 Cystine Free CTG 384 CSA (EC$_{50}$) [µM] |
|---|---|---|
| 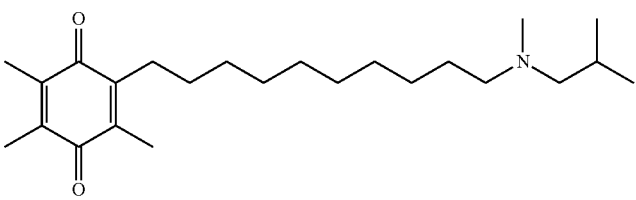 [SMILES: CC1=C(C)C(=O)C(CCCCCCCCCCN(C)CC(C)C)=C(C)C1=O] | 20 | ++++ |
| 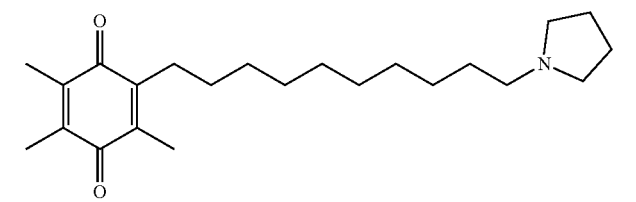 [SMILES: CC1=C(C)C(=O)C(CCCCCCCCCCN2CCCC2)=C(C)C1=O] | 21 | ++++ |
| 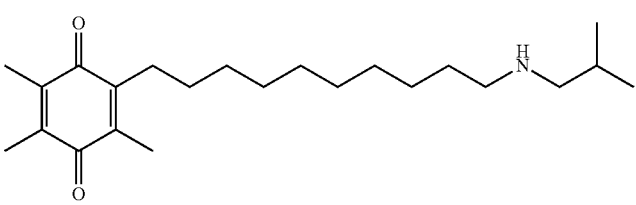 [SMILES: CC1=C(C)C(=O)C(CCCCCCCCCCNCC(C)C)=C(C)C1=O] | 22 | ++++ |

*++++ is <0.1 µM;
+++ is 0.1-0.5 µM;
++ is 0.5-1.0 µM;
+ is 1.0-2.0 µM

Example 25. Assessment of Radio-Protection Against Exposure to Total Body Irradiation (TBI)

Compounds described herein are tested to determine their effects on survival following total body irradiation (TBI).

Experimental Design: Male CD2F1 mice (Charles River Laboratories), aged 6-8 weeks, are randomly and prospectively assigned to receive treatment with either a test compound or vehicle only. On Day 0, the animals are placed in a pie cage and exposed to total body irradiation (TBI) with a dose of 8.75 Gy or 9.75 Gy to achieve an approximate LD50 or LD80 survival outcome, respectively. Treatments are administered at 24 hours and 4 hours prior to irradiation. Animals are monitored for survival twice daily for 30 days, and those that lose greater than 30% of their total starting body weight are euthanized and counted as having died on that day.

Animal Housing and Environment: The animals are housed in disposable cages with sterile wood chip bedding, food, and water. The mice are acclimated for at least 3 days and given food and tap water ad libitum. The animals are examined prior to initiation of the study to assure adequate health and suitability. Animals that are found to be diseased or unsuitable were not assigned to the study.

During the course of the study, 12-hour light/12-hour dark cycles are maintained. A nominal temperature range of 20-23° C. with a relative humidity between 30% and 70% are also maintained. LabDiet 5053-certified PicoLab Rodent Diet and sterile water are provided ad libitum. The animals are not fasted prior to dosing.

Total Body Irradiation (TBI): Mice are placed in a pie cage in groups of 9-11 at a time. Radiation is generated with a 160 kilovolt potential (18-ma) source at a focal distance of 25 cm, hardened with a 0.35 mm Al filtration system. The animals are subjected to TBI at a rate of <100 cGy. Dosimetry (Fluke 3504 dosimeter with farmer type 0.6 cm ion chamber probe) is used with each radiation to ensure that all animals receive the correct dose.

Animal Weights: All animals are weighed daily throughout this study and their survival is recorded in order to assess possible differences in animal weight among treatment groups as an indication for radiation-induced toxicity. Group weight change is expressed as a mean percent weight change and mean percent weight change area under the curve. Animals that lose greater than 30% of their total starting body weight are euthanized.

Animals Found Dead or Moribund: Animal deaths in this model generally occur as a consequence of radiation toxicity. Animals are monitored on a daily basis, and those exhibiting weight loss greater than 30%, are unable to ambulate, achieve food and water, and/or appear moribund are euthanized. Animals are not replaced during the course of the study.

Statistical Analysis: Statistical differences between treatment groups are determined using appropriate statistical techniques. A one-way ANOVA or ANOVA on ranks is used to evaluate the area-under the curve for weight gain. A Kaplan-Meier survival curve is provided to assess statistical differences in survival among treatment groups.

Test Article preparation: Test compound is dissolved in PEG-400/2% Tween 80 and mixed until visually homogeneous at a concentration of 90 mg/mL. All compound solutions are stored at room temperature, protected from light, and used within 24 hours of preparation. Test Article Administration: The animals are each administered with single or multiple subcutaneous (SC) doses of the test compound formulation or vehicle only formulation as described herein. All animals are dosed at approximately the same time on the dosing day (±1 hour). Subcutaneous doses are administered via bolus injection between the skin and underlying layers of tissue in the scapular region on the back of each animal. The hair is not clipped from the injection site prior to dosing. The injection site is monitored for necrosis and other changes to the skin and hair.

Animals receiving compounds disclosed herein show improved survival and body weight compared with animals administered vehicle only.

Example 26. Assessment of Radio-Protection Against Exposure to Gamma Radiation

Compounds described herein are tested to determine their effects on survival and other symptoms of radiation damage following exposure to gamma-radiation.

Mice are randomly and prospectively assigned to receive treatment with either a test compound or vehicle only. On Day 0, the animals are exposed to gamma-radiation with a dose sufficient to achieve survival outcome between LD20 to LD80. Treatments are administered at set time points between 48 hours and 1 hour prior to irradiation. Animals are monitored for survival twice daily, and those that lose greater than 30% of their total starting body weight are euthanized and counted as having died on that day. Animals are also monitored for various symptoms of radiation damage.

Statistical differences between treatment groups are determined using appropriate statistical techniques. A one-way ANOVA or ANOVA on ranks is used to evaluate the area-under the curve for weight gain. A Kaplan-Meier survival curve is provided to assess statistical differences in survival among treatment groups.

Test compound is dissolved in PEG-400/2% Tween 80 and mixed until visually homogeneous at a concentration of 90 mg/mL. All compound solutions are stored at room temperature, protected from light, and used within 24 hours of preparation.

The animals are each administered with single or multiple subcutaneous (SC) doses of the test compound formulation or vehicle only formulation as described herein. All animals are dosed at approximately the same time on the dosing day (±1 hour). Subcutaneous doses are administered via bolus injection between the skin and underlying layers of tissue in the scapular region on the back of each animal. The hair is not clipped from the injection site prior to dosing. The injection site is monitored for necrosis and other changes to the skin and hair.

Compounds are evaluated for their ability to increase survival rates and/or reduce or prevent symptoms of radiation damage. Animals receiving compounds disclosed herein show improved survival and/or other symptoms of radiation damage (e.g. body weight) compared with animals administered vehicle only.

Example 27: Assessment of Radio-Protection Against Exposure to Ultraviolet Radiation Compounds described herein are tested to determine their effects on survival and other symptoms of radiation damage following exposure to ultraviolet radiation.

Mice are randomly and prospectively assigned to receive treatment with either a test compound or vehicle only. On Day 0, the animals are exposed to ultraviolet radiation (UVA and/or UVB) with doses sufficient to achieve an LD20 to LD80 survival outcome. Treatments are administered at set time points between 48 hours and 1 hour prior to irradiation. Animals are monitored for survival twice daily, and those that lose greater than 30% of their total starting body weight are euthanized and counted as having died on that day. Animals are also monitored for various symptoms of radiation damage.

Statistical differences between treatment groups are determined using appropriate statistical techniques. A one-way ANOVA or ANOVA on ranks is used to evaluate the area-under the curve for weight gain. A Kaplan-Meier survival curve is provided to assess statistical differences in survival among treatment groups.

Test compound is dissolved in PEG-400/2% Tween 80 and mixed until visually homogeneous at a concentration of 90 mg/mL. All compound solutions are stored at room temperature, protected from light, and used within 24 hours of preparation.

The animals are each administered with single or multiple subcutaneous (SC) doses of the test compound formulation or vehicle only formulation as described herein. All animals are dosed at approximately the same time on the dosing day (±1 hour). Subcutaneous doses are administered via bolus injection between the skin and underlying layers of tissue in the scapular region on the back of each animal. The hair is not clipped from the injection site prior to dosing. The injection site is monitored for necrosis and other changes to the skin and hair.

Compounds are evaluated for their ability to increase survival rates and/or reduce or prevent symptoms of radiation damage. Animals receiving compounds disclosed herein show improved survival and/or other symptoms of radiation damage (e.g. body weight) compared with animals administered vehicle only.

Example 28. Administration of Compounds Disclosed Herein

A compound disclosed herein is presented in a capsule containing 300 mg of compound in a pharmaceutically acceptable carrier. A capsule is taken orally, once a day, preferably during breakfast or lunch. In case of very young children, the capsule is broken and its contents mixed with food.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of the formula I:

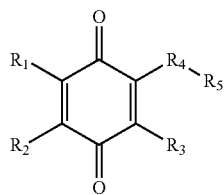

or the hydroquinone form thereof;

wherein:

$R_1$ and $R_2$ are independently $C_1$-$C_{10}$ alkyl;

$R_3$ is $C_1$-$C_6$ alkyl;

$R_4$ is $C_1$-$C_{12}$ n-alkyl and $R_5$ is —$OCH_3$, —$OCF_3$, or —$OCH_2CF_3$, wherein $R_5$ is attached to $R_4$ at any chemically possible location on the $C_1$-$C_{12}$ n-alkyl group; or $R_4$ is $C_6$-$C_{12}$ alkyl and $R_5$ is —$CF_3$, wherein $R_5$ is attached to $R_4$ at any chemically possible location on the $C_6$-$C_{12}$ alkyl group;

or a salt, a stereoisomer, or mixture of stereoisomers thereof;

with the proviso that the compound is not

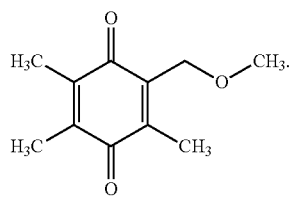

2. The compound of claim 1, wherein the compound is a quinone.

3. The compound of claim 1, wherein the compound is a hydroquinone.

4. The compound of claim 1, wherein $R_1$ and $R_2$ are methyl.

5. The compound of claim 1, wherein $R_3$ is $C_1$-$C_4$ alkyl.

6. The compound of claim 1, wherein $R_3$ is methyl.

7. The compound of claim 1, wherein $R_3$ is isopropyl.

8. The compound of claim 1, wherein $R_5$ is —$CF_3$.

9. The compound of claim 1, wherein $R_5$ is —$OCH_3$.

10. The compound of claim 1, wherein $R_5$ is —$OCF_3$.

11. The compound of claim 1, wherein $R_5$ is —$OCH_2CF_3$.

12. The compound of claim 1, wherein $R_4$ is $C_6$-$C_{12}$ alkyl for all values of $R_5$.

13. The compound of claim 1, wherein $R_4$ is a n-alkyl for all values of $R_5$.

14. The compound of claim 13, wherein $R_4$ is $C_6$ alkyl.

15. The compound of claim 13, wherein $R_4$ is $C_9$ alkyl.

16. The compound of claim 13, wherein $R_4$ is $C_{10}$ alkyl.

17. The compound of claim 13, wherein $R_4$ is $C_{11}$ alkyl.

18. The compound of claim 1, wherein the compound is selected from the group consisting of:

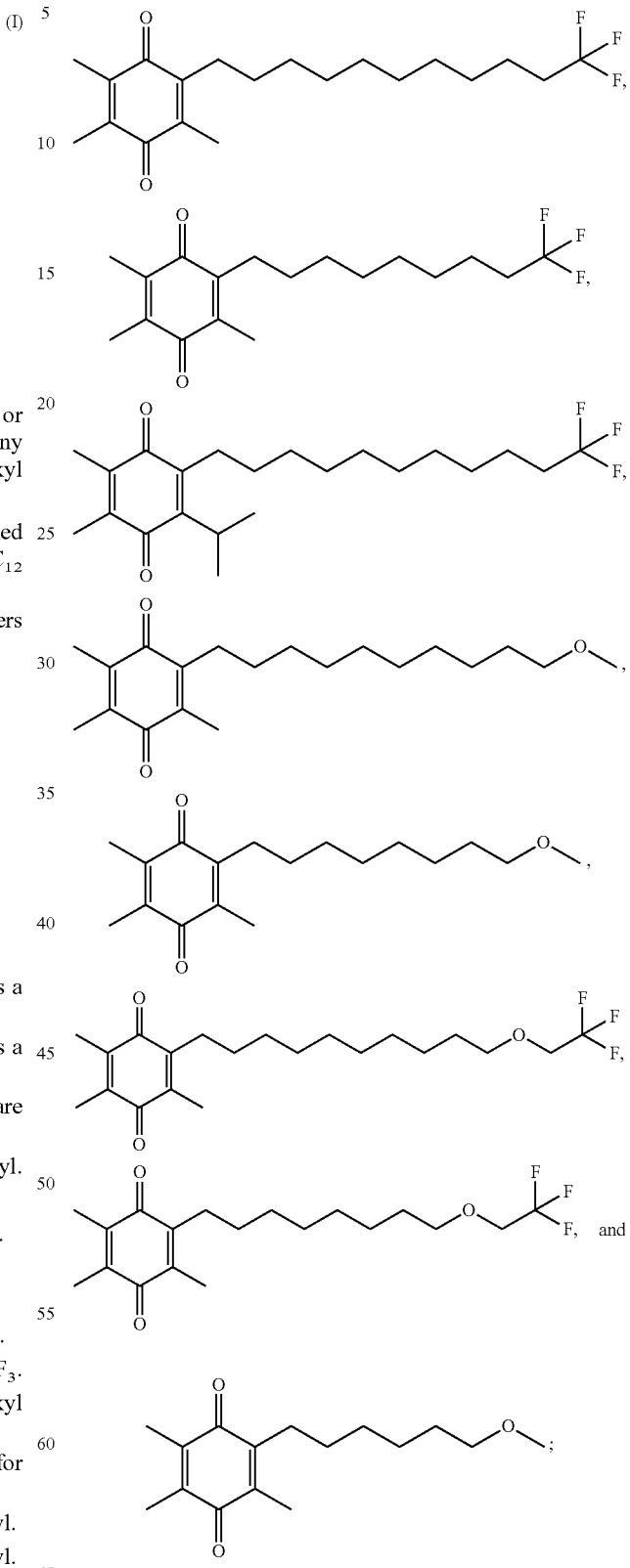

and the hydroquinone forms thereof.

19. The compound of claim 1, wherein the compound is:

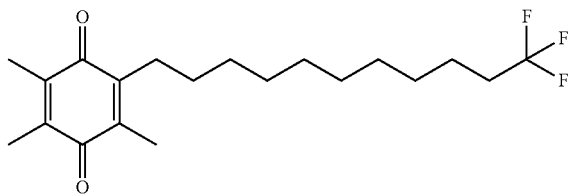

or the hydroquinone form thereof.

20. The compound of claim 1, wherein the compound is:

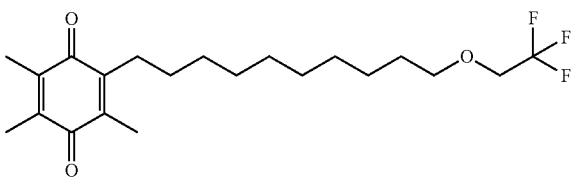 [SMILES: CC1=C(C)C(=O)C(CCCCCCCCCCOCC(F)(F)F)=C(C)C1=O]

or the hydroquinone form thereof.

21. The compound of claim 1, wherein the compound is:

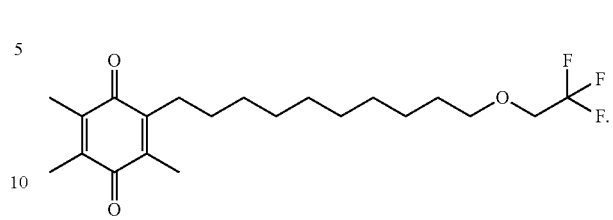

22. A pharmaceutical composition comprising a compound of claim 1 and a pharmaceutically acceptable carrier, wherein the compound is not a salt.

23. A pharmaceutical composition comprising a compound of claim 20 and a pharmaceutically acceptable carrier.

* * * * *